US009815825B2

(12) United States Patent
Schwiebert et al.

(10) Patent No.: US 9,815,825 B2
(45) Date of Patent: *Nov. 14, 2017

(54) COUMARIN DERIVATIVES AND METHODS OF USE IN TREATING CYSTIC FIBROSIS, CHRONIC OBSTRUCTIVE PULMONARY DISEASE, AND MISFOLDED PROTEIN DISORDERS

(71) Applicant: DISCOVERYBIOMED, INC., Birmingham, AL (US)

(72) Inventors: Erik Schwiebert, Birmingham, AL (US); John Streiff, Birmingham, AL (US); John Dixon, Leicestershire (GB); Hongwu Gao, Shanghai (CN)

(73) Assignee: DiscoveryBiomed, Inc., Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/775,010

(22) PCT Filed: Mar. 14, 2014

(86) PCT No.: PCT/US2014/027079
§ 371 (c)(1),
(2) Date: Sep. 11, 2015

(87) PCT Pub. No.: WO2014/152213
PCT Pub. Date: Sep. 25, 2014

(65) Prior Publication Data
US 2016/0024065 A1 Jan. 28, 2016

Related U.S. Application Data

(60) Provisional application No. 61/788,353, filed on Mar. 15, 2013.

(51) Int. Cl.
| | |
|---|---|
| *C07D 417/04* | (2006.01) |
| *C07D 405/04* | (2006.01) |
| *C07D 413/04* | (2006.01) |
| *C07D 417/14* | (2006.01) |
| *C07D 471/04* | (2006.01) |
| *C07D 491/052* | (2006.01) |
| *C07D 493/04* | (2006.01) |
| *C07D 498/04* | (2006.01) |

(52) U.S. Cl.
CPC ......... *C07D 417/04* (2013.01); *C07D 405/04* (2013.01); *C07D 413/04* (2013.01); *C07D 417/14* (2013.01); *C07D 471/04* (2013.01); *C07D 491/052* (2013.01); *C07D 493/04* (2013.01); *C07D 498/04* (2013.01)

(58) Field of Classification Search
CPC .......................... C07D 417/04; C07D 417/14; C07D 491/052; C07D 405/04; C07D 413/04; C07D 471/04; C07D 493/04; C07D 498/04
See application file for complete search history.

(56) References Cited

U.S. PATENT DOCUMENTS

| | | | |
|---|---|---|---|
| 2003/0055263 A1 | 3/2003 | Priepke et al. | |
| 2006/0079543 A1 | 4/2006 | Sum et al. | |
| 2007/0032518 A1 | 2/2007 | Norman et al. | |
| 2016/0038475 A1* | 2/2016 | Schwiebert | C07D 417/04 |
| | | | 514/312 |

FOREIGN PATENT DOCUMENTS

| | | |
|---|---|---|
| CN | 101039919 A | 9/2007 |
| CN | 101076703 A | 11/2007 |
| CN | 101351208 A | 1/2009 |
| CN | 105121437 | 12/2015 |
| CN | 105246887 | 1/2016 |
| EP | 2970248 | 1/2016 |
| IN | 7593DELNP2015 | 1/2016 |
| JP | 55066580 | 5/1980 |
| WO | 03006443 A2 | 1/2003 |
| WO | 03/066630 * | 8/2003 |
| WO | 03066630 | 8/2003 |
| WO | 03105842 A1 | 12/2003 |
| WO | 2006044456 A1 | 4/2006 |
| WO | 2007053847 A2 | 5/2007 |
| WO | 2009076665 A1 | 6/2009 |
| WO | 2010111713 A2 | 9/2010 |
| WO | 2012171954 | 12/2012 |

(Continued)

OTHER PUBLICATIONS

Mori, CHem Med Chem, vol. 8, 2013, 484-496.*
Ambre, Canadian J Chem, 2012, 90(8), 675-692.*
Mladenovic, E J Med Chem, 54, 144-158, 2012.*
Mohamed, Molecules, 17, 2012, 971-988.*
Raza, ISRN Pharmacology, 2012, 1-11.*
Matic, CA159:437927, abstract only of J BIochem &Mol Tox, 26(8), 322-330, 2012.*
Panigrahi, CA75:129705 abstract only of J Indian Chem SOc, 48(7), 665-668, 1971.*
Koti, Synthetic Comm, 37, 99-105, 2007.*
[Online] Registry via STN, RN 403721-73-3, Apr. 3, 2002.
[Online] Registry via STN, RN 403721-74-4, Apr. 3, 2002.

(Continued)

*Primary Examiner* — D M Seaman
(74) *Attorney, Agent, or Firm* — Kilpatrick Townsend & Stockton LLP

(57) ABSTRACT

Novel CFTR corrector compounds that are effective in rescuing halide efflux, delF508-CFTR protein processing, and apical functional chloride ion transport in a cell are provided. Also provided are methods for treating protein folding disorders (e.g., cystic fibrosis and chronic obstructive pulmonary diseases). The methods include administering a CFTR corrector compound or pharmaceutically acceptable salt or prodrug thereof. Methods of rescuing halide efflux in a cell, correcting a processing defect of a delF508-CFTR protein in a cell, and correcting functional delF508-CFTR chloride channels in a cell are also provided.

22 Claims, 17 Drawing Sheets

(56) References Cited

FOREIGN PATENT DOCUMENTS

| WO | 2014152213 | 9/2014 |
|---|---|---|
| WO | 2014152278 | 11/2014 |

OTHER PUBLICATIONS

[Online] Registry via STN, RN 724744-64-3, Aug. 10, 2004.
[Online] Registry via STN, RN 313954-55-1, Jan. 15, 2001.
[Online] Registry via STN, RN 313954-56-2, Jan. 15, 2001.
[Online] Registry via STN, RN 312703-21-2, Jan. 4, 2001.
[Online] Registry via STN, RN 325473-18-5, Mar. 4, 2001.
[Online] Registry via STN, RN 325804-06-6, Mar. 6, 2001.
[Online] Registry via STN, RN 325804-07-7, Mar. 6, 2001.
Abraham et al., Cystic fibrosis hetero- and homozygosity is associated with inhibition of breast cancer growth, Nature Medicine, vol. 2, No. 5, May 1996, pp. 593-596.
Chinese Application No. 201480009649.8, Office Action mailed on Dec. 31, 2015, 2 pages.
Desai et al., A convenient, rapid and eco-friendly synthesis of isoxazoline heterocyclic moiety containing bridge at 2°-amine as potential pharmacological agent, Journal of the Iranian Chemical Society, vol. 5, No. 1, 2008, pp. 67-73.
Ding et al., Methylation profile of the promoter CpG islands of 14 "drug-resistance" genes in hepatocellular carcinoma, World Journal of Gastroenterology, vol. 10, No. 23, Dec. 2004, pp. 3433-3440.
Eriksson et al., Specific in vivo phosphorylation sites determine the assembly dynamics of vimentin intermediate filaments, J. Cell Sci., vol. 117, Part 6, Feb. 29, 2004, pp. 919-932.
Goto et al., Phosphorylation and reorganization of vimentin by p21-activated kinase (PAK), Genes Cells, vol. 7, No. 2, Feb. 2002, pp. 91-97.
Hanmantgad et al., Biomimetic thiazolyl coumarins, National Academy Science Letters, vol. 7, No. 3, 1984, pp. 77-78.
Lahat et al., Vimentin is a Novel Anti-Cancer Therapeutic Target; Insights from in Vitro and in Vivo Mice Xenograft Studies, PLoS One, vol. 5, No. 4, Apr. 16, 2010, 19 pages.
Lee et al., Cdk5 mediates vimentin Ser56 phosphorylation during GTP-induced secretion by neutrophils, J Cell Physiol., vol. 227, No. 2, Feb. 2012, pp. 739-750.
Li et al., Critical role of vimentin phosphorylation at Ser-56 by p21-activated kinase in vimentin cytoskeleton signaling, J Biol Chem., vol. 281, No. 45, Nov. 10, 2006, pp. 34716-34724.
Li et al., Cystic fibrosis transmembrane conductance regulator gene mutation and lung cancer risk, Lung Cancer, vol. 70, No. 1, Oct. 2010, pp. 14-21.
McWilliams et al., Cystic fibrosis transmembrane conductance regulator (CFTR) gene mutations and risk for pancreatic adenocarcinoma, Cancer, vol. 116, No. 1, Jan. 1, 2010, pp. 203-209.
McWilliams et al., Risk of malignancy in first-degree relatives of patients with pancreatic carcinoma, Cancer, vol. 104, No. 2, Jul. 15, 2005, pp. 388-394.
Mishra et al., Global methylation pattern of genes in androgen-sensitive and androgen-independent prostate cancer cells, Molecular Cancer Therapeutics, vol. 9, No. 1, Jan. 2010, pp. 33-45.
Mori et al., A Combination Strategy to Inhibit Pim-1: Synergism between Noncompetitive and ATP-Competitive Inhibitors, ChemMedChem., vol. 8, No. 3, Feb. 22, 2013, pp. 484-496.
Moribe et al., Methylation of multiple genes as molecular markers for diagnosis of a small, well-differentiated hepatocellular carcinoma, International Journal of Cancer, vol. 125, No. 2, Jul. 15, 2009, pp. 388-397.
Neglia et al., The risk of cancer among patients with cystic fibrosis. Cystic Fibrosis and Cancer Study Group, The New England Journal of Medicine, vol. 332, No. 8, Feb. 23, 1995, pp. 494-499.
Oh et al., Association of CFTR gene polymorphisms with papillary thyroid cancer, Oncology Letters, vol. 3, No. 2, Feb. 2012, pp. 455-461.
Omary et al., "Heads and tails" of intermediate filament phosphorylation: multiple sites and functional insights, Trends Biochem Sci., vol. 31, No. 7, Jul. 2006, pp. 383-394.
Padua et al., The cystic fibrosis delta F508 gene mutation and cancer, Human Mutation, vol. 10, No. 1, 1997, pp. 45-48.
Panigrahi et al., 4-(3'-Coumarinyl)-2-arylaminothiazoles and some of their derivatives, Journal of the Indian Chemical Society, vol. 48, No. 7, 1971, pp. 665-668.
International Application No. PCT/US2014/027079, International Search Report and Written opinion dated Sep. 18, 2014, 13 pages.
Qiao et al., Cystic fibrosis transmembrane conductance regulator (CFTR) gene 5T allele may protect against prostate cancer: a case-control study in Chinese Han population, Journal of Cystic Fibrosis, vol. 7, No. 3, May 2008, pp. 210-214.
Son et al., Promoter hypermethylation of the CFTR gene and clinical/pathological features associated with non-small cell lung cancer, Respirology, vol. 16, No. 8, Nov. 2011, pp. 1203-1209.
Srimanth et al., Synthesis of some new types of thiazolyl coumarins, Indian Journal of Chemistry, vol. 388, No. 4, 1999, pp. 473-475.
Thaiparambil et al., Withaferin A inhibits breast cancer invasion and metastasis at sub-cytotoxic doses by inducing vimentin disassembly and serine 56 phosphorylation, Int J Cancer, vol. 129, No. 11, Dec. 2011, pp. 2744-2755.
Venugopala et al., Synthesis and evaluation of some substituted 2-arylamino coumarinyl thiazoles as potential NSAIDs, Asian Journal of Chemistry, vol. 16, No. 2, 2004, pp. 872-876.
Warren et al., Frequency of carriers of cystic fibrosis gene among patients with myeloid malignancy and melanoma, BMJ, vol. 302, No. 6779, Mar. 30, 1991, pp. 760-761.
Xie et al., CFTR suppresses tumor progression through miR-193b targeting urokinase plasminogen activator (uPA) in prostate cancer, Oncogene, vol. 32, No. 18, May 2, 2013, pp. 1-10.
Yang et al., Stimulation of Airway and Intestinal Mucosal Secretion by Natural Coumarin CFTR Activators, Frontiers in Pharmacology, vol. 2, No. 52, Sep. 27, 2011, 5 pages.
Yasui et al., Protein kinases required for segregation of vimentin filaments in mitotic process, Oncogene, vol. 20, No. 23, May 24, 2001, pp. 2868-2876.
EP14767955.9, "Office Action", dated Sep. 5, 2016, 10 pages.
Koti, et al., "Intramolecular Amidation: Synthesis of Novel Thiazole-Fused Diazepinones", Synthetic Communications, vol. 37, No. 1, Jan. 1, 2007, 8 pages.
Lin, et al., "Double Functional Group Transformations for Fluorescent Probe Construction: A Fluorescence Turn-on Probe for Thioureas", Chemistry—A European Journal, vol. 16, No. 22, Jun. 11, 2010, pp. 6454-6457, 4 pages.
U.S. Appl. No. 14/775,050, "Non-Final Office Action", dated Oct. 20, 2016, 12 pages.
Fayad, et al., "Identification of Agents that Induce Apoptosis of Multicellular Tumour Spheroids: Enrichment for Mitotic Inhibitors with Hydrophobic Properties", Chemical Biology & Drug Design, vol. 78, No. 4, Oct. 2011, pp. 547-557.
Solak, et al., "Colchicine treatment in autosomal dominant polycystic kidney disease: Many points in common", Medical Hypotheses, vol. 74, No. 2, Feb. 2010, pp. 314-317.
CN201480009649.8, "Office Action", dated Nov. 15, 2016, 29 pages.
EP14767955.9, "Extended European Search Report", dated Dec. 12, 2016, 13 pages.
EP14768111.8, "Partial Supplementary European Search Report", dated Nov. 2, 2016, 12 pages.
Rao, et al., "Microwave-assisted synthesis of some-chloro-3-[2-(substituted anilino)-1,3-thiazol-4-yl]-2H-1-benzopyran-2-ones as antibacterial agents", Indian Journal of Heterocyclic Chemistry, National Academy of Chemistry and Biology vol. 17, No. 4, Jan. 1, 2008, pp. 397-400.
Yusufzai, et al., "3-(2-Methylamino-1,3-thiazol-4-yl)-2 H-chromen-2-one", Acta Crystallographica Section E Structure Reports Online, vol. 68, No. 8, Jul. 10, 2012, pp. 2416-2417.
CN201480015013.4, Office Action dated Jan. 24, 2017, 30 pages.
EP14768111.8, Extended European Search Report dated Feb. 15, 2017, 20 pages.
Chinese Patent Application No. 201480009649.8, Office Action dated Aug. 1, 2017, 28 pages with English translation.

(56) References Cited

OTHER PUBLICATIONS

Deng, "Stimulation of airway and intestinal mucosal secretion by natural coumarin CFTR activators", J. Med. Chem., 49:5, pp. 1684-1692, Feb. 15, 2006.
Wang, et al., "CFTR and cystic fibrosis", Int. J. Pathol. Clin. Med., 26:2, pp. 142-145, Apr. 30, 2006, Abstract in English.

\* cited by examiner (IC50 of both E-308 data sets is 3 microM)

◇ Pre-Experiment Potential Difference for E-308
▣ Amiloride Sensitive Current for E-308
◇ Pre-Experiment Potential Difference for E-328
△ Amiloride Sensitive Current for E-328

COUMARIN DERIVATIVES AND METHODS OF USE IN TREATING CYSTIC FIBROSIS, CHRONIC OBSTRUCTIVE PULMONARY DISEASE, AND MISFOLDED PROTEIN DISORDERS

CROSS-REFERENCE TO PRIORITY APPLICATION

This application claims priority to U.S. Provisional Application No. 61/788,353, filed Mar. 15, 2013, which is incorporated herein by reference in its entirety.

STATEMENT REGARDING FEDERALLY FUNDED RESEARCH

This invention was made with government support under Grant No. NIDDK Phase II SBIR DK084658-03 awarded by the National Institutes of Health. The government has certain rights in the invention.

BACKGROUND

Cystic fibrosis is an example of a protein folding disorder. It is a hereditary disease caused by mutations in a gene encoding the cystic fibrosis transmembrane conductance regulator (CFTR). The CFTR gene encodes a chloride channel that is expressed in multiple epithelial cell types. A common CFTR mutation, delF508, causes the failure of CFTR to traffic correctly to the plasma membrane because of protein misfolding. The delF508 mutation is estimated to account for 90% of mutant alleles. Because of its high degree of incidence in the cystic fibrosis population, delF508-CFTR is a prime target for cystic fibrosis therapeutics. As such, delF508-CFTR has been extensively studied and is a model for the study of protein folding diseases.

SUMMARY

Coumarin derivative compounds and methods for the treatment of protein folding disorders, such as cystic fibrosis, chronic obstructive pulmonary diseases, and rare misfolded protein disorders, are provided. Cystic fibrosis (CF) is used throughout as an example of such a protein folding disorder. The methods include administering to a subject a CFTR corrector (i.e., a compound effective in rescuing halide efflux in a cell).

A class of CFTR correctors includes compounds of the following formula:

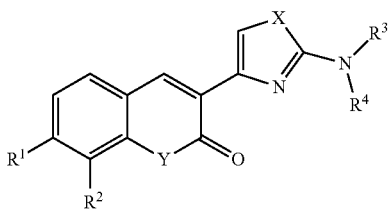

and pharmaceutically acceptable salts or prodrugs thereof. In this class of compounds, $R^1$ is hydrogen, halogen, hydroxyl, substituted or unsubstituted alkoxyl, substituted or unsubstituted amino, substituted or unsubstituted $C_{1-6}$ alkyl, or substituted or unsubstituted heterocycloalkyl; $R^2$ is hydrogen, halogen, hydroxyl, nitro, cyano, azido, thiocyanato, trifluoromethyl, substituted or unsubstituted alkoxyl, substituted or unsubstituted amino, substituted or unsubstituted carbonyl, or substituted or unsubstituted $C_{1-6}$ alkyl; $R^3$ is hydrogen or substituted or unsubstituted $C_{1-6}$ alkyl; $R^4$ is substituted or unsubstituted $C_{1-6}$ alkyl, substituted or unsubstituted aryl, or substituted or unsubstituted heteroaryl; X is S or O; and Y is O or $NCH_3$. Optionally, the compound is selected from the group consisting of:

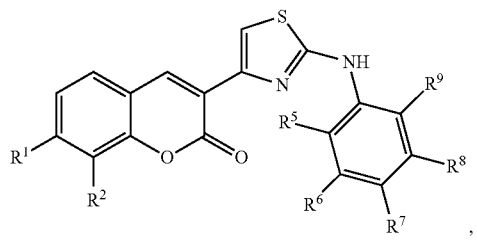

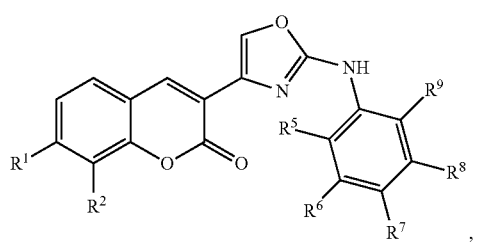

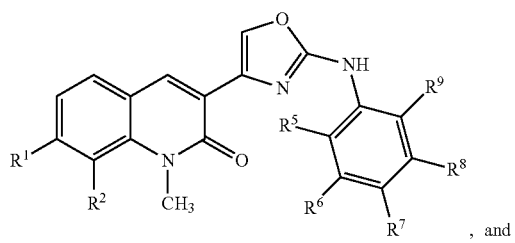

, and

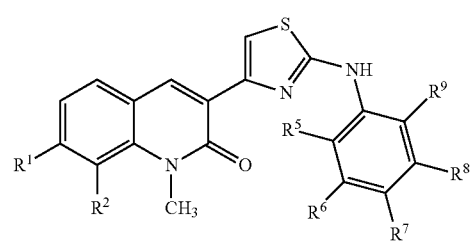

wherein $R^5$, $R^6$, $R^7$, $R^8$, and $R^9$ are each independently selected from hydrogen, halogen, hydroxyl, substituted or unsubstituted alkoxy, cyano, nitro, trifluoromethyl, substituted or unsubstituted carbonyl, substituted or unsubstituted amino, substituted or unsubstituted $C_{1-6}$ alkyl, substituted or unsubstituted $C_{2-6}$ alkenyl, substituted or unsubstituted aryl, substituted or unsubstituted sulfonamide, substituted or unsubstituted sulfonyl, or substituted or unsubstituted thio. Optionally, $R^1$ and $R^2$, $R^5$ and $R^6$, $R^6$ and $R^7$, $R^7$ and $R^8$, or $R^8$ and $R^9$ combine to form a substituted or unsubstituted aryl, substituted or unsubstituted cycloalkenyl, substituted or unsubstituted heteroaryl, or substituted or unsubstituted heterocycloalkyl.

A class of CFTR correctors includes compounds of the following formula:

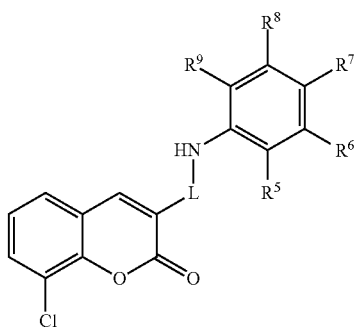

and pharmaceutically acceptable salts or prodrugs thereof. In this class of compounds, L is a heteroaryl; and $R^5$, $R^6$, $R^7$, $R^8$, and $R^9$ are each independently selected from hydrogen and methoxy.

A class of CFTR correctors includes compounds of the following formula:

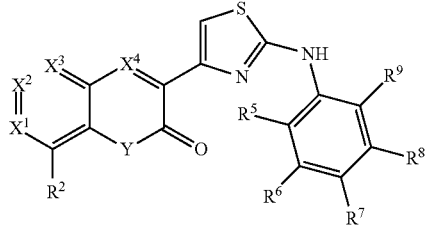

and pharmaceutically acceptable salts or prodrugs thereof. In this class of compounds, $X^1$, $X^2$, $X^3$ and $X^4$ are each independently selected from CH and N; Y is O or NR, where R is hydrogen or methyl; $R^2$ is hydrogen, $C_{1-6}$ alkyl, halogen, or trifluoroalkyl; and $R^5$, $R^6$, $R^7$, $R^8$, and $R^9$ are each independently selected from hydrogen and methoxy.

A class of CFTR correctors includes compounds of the following formula:

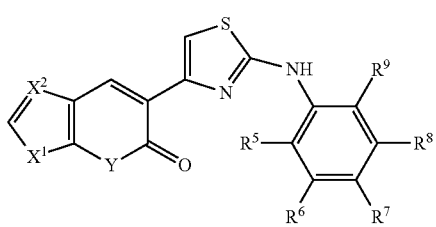

and pharmaceutically acceptable salts or prodrugs thereof. In this class of compounds, $X^1$ is O or $NCH_3$; $X^2$ is CH or N; Y is O, NH, or $NCH_3$; and $R^5$, $R^6$, $R^7$, $R^8$, and $R^9$ are each independently selected from hydrogen and methoxy.

A class of CFTR correctors includes compounds of the following formula:

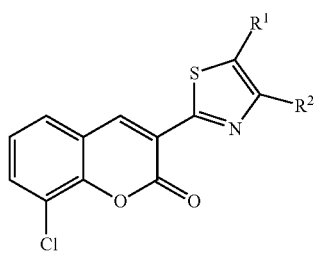

and pharmaceutically acceptable salts or prodrugs thereof. In this class of compounds, $R^1$ and $R^2$ are each independently selected from hydrogen, substituted or unsubstituted amino, and substituted or unsubstituted carbonyl.

A class of CFTR correctors includes compounds of the following formula:

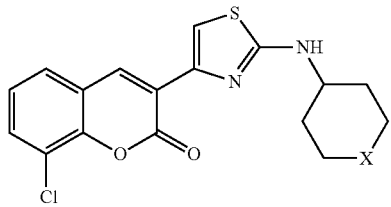

and pharmaceutically acceptable salts or prodrugs thereof. In this class of compounds, X is $CH_2$, NH, or O.

Also described herein is a composition comprising one or more of the compounds described herein and a pharmaceutically acceptable carrier.

A method for the treatment of a protein folding disorder in a subject is also described herein. The method for the treatment of a protein folding disorder in a subject comprises administering to the subject an effective amount of a compound as described herein. Optionally, the protein folding disorder is cystic fibrosis. Optionally, the protein folding disorder is a chronic obstructive pulmonary disease.

Also provided herein are methods of rescuing halide efflux in a cell, correcting a processing defect of a delF508-CFTR protein in a cell, and correcting functional delF508-CFTR chloride channels in a cell. The method of rescuing halide efflux in a cell comprises contacting a cell with a compound as described herein, wherein the cell endogenously expresses a CFTR mutation. Optionally, the CFTR mutation is delF508-CFTR. Optionally, the halide efflux is chloride efflux.

A method of correcting a processing defect of a delF508-CFTR protein in a cell comprises contacting a cell with a compound as described herein, wherein the cell expresses a delF508-CFTR mutation. Optionally, the cell is a CF human airway epithelial cell or a CF human lung cell.

A method of correcting functional delF508-CFTR chloride channels in a cell comprises contacting a cell with a compound as described herein, wherein the cell is a polarized epithelial cell. Optionally, the method is performed in vitro. Optionally, the method is performed in vivo.

The details of one or more embodiments are set forth in the drawings and the description below. Other features, objects, and advantages will be apparent from the description and drawings, and from the claims.

DETAILED DESCRIPTION

Figure 1:
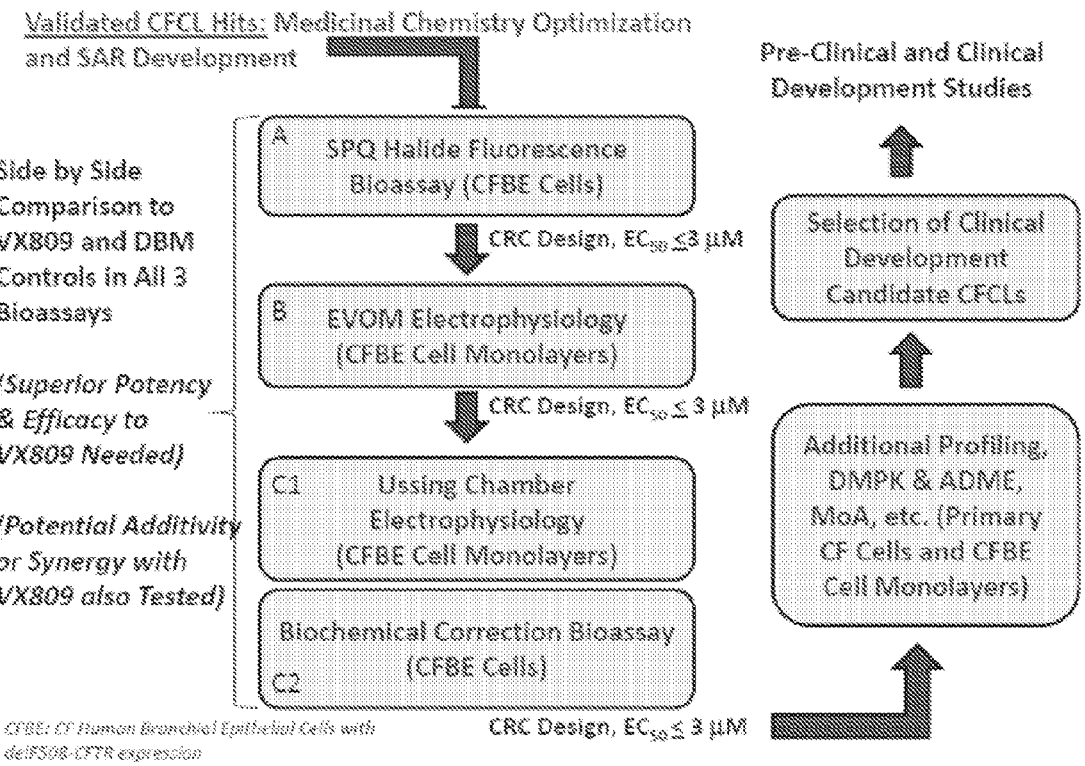
FIG. 1 is a schematic showing a general approach for identifying delF508-CFTR correctors.

The coumarin derivative compounds and methods described herein are useful in the treatment of protein folding disorders. The compounds and methods described herein can be useful, for example, in the treatment of cystic fibrosis, familial hypercholesterolemia, diabetes mellitus, alpha1 antitrypsin deficiency, Fabry's disease, Gaucher's disease, Pompe's disease, hypothyrosis, Alzheimer's disease, and chronic obstructive pulmonary diseases (COPD). These compounds are able to correct the misfolding or defective trafficking of delF508-CFTR; thus, the compounds are effective as CFTR correctors (i.e., the compounds are effective in rescuing halide efflux in a cell). Methods for screening for CFTR corrector compounds are also described herein.

I. Compounds

A class of coumarin derivatives described herein is represented by Formula I:

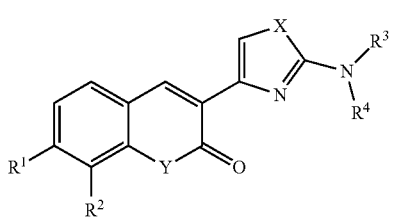

I and pharmaceutically acceptable salts or prodrugs thereof.

In Formula I, $R^1$ is hydrogen, halogen, hydroxyl, substituted or unsubstituted alkoxyl, substituted or unsubstituted amino, substituted or unsubstituted $C_{1-6}$ alkyl, or substituted or unsubstituted heterocycloalkyl.

Also, in Formula I, $R^2$ is hydrogen, halogen, hydroxyl, nitro, cyano, azido, thiocyanato, trifluoromethyl, substituted or unsubstituted alkoxyl, substituted or unsubstituted amino, substituted or unsubstituted carbonyl, or substituted or unsubstituted $C_{1-6}$ alkyl.

Additionally, in Formula I, $R^3$ is hydrogen or substituted or unsubstituted $C_{1-6}$ alkyl. Further, in Formula I, $R^4$ is substituted or unsubstituted $C_{1-6}$ alkyl, substituted or unsubstituted aryl, or substituted or unsubstituted heteroaryl.

Also, in Formula I, X is S or O.

Additionally, in Formula I, Y is O, NH, or $NCH_3$.

As used herein, the terms alkyl and alkenyl include straight- and branched-chain monovalent substituents. Examples include methyl, ethyl, isobutyl, and the like. Ranges of these groups useful with the compounds and methods described herein include $C_1$-$C_8$ alkyl and $C_3$-$C_8$ alkenyl.

Heteroalkyl and heteroalkenyl are defined similarly as alkyl and alkenyl, but can contain O, S, or N heteroatoms or combinations thereof within the backbone. Ranges of these groups useful with the compounds and methods described herein include $C_1$-$C_8$ heteroalkyl and $C_3$-$C_8$ heteroalkenyl.

The term cycloalkyl includes cyclic alkyl groups having a single cyclic ring or multiple condensed rings. Examples include cyclohexyl, cyclopentylethyl, and adamantanyl. A range of these groups useful with the compounds and methods described herein includes $C_3$-$C_9$ cycloalkyl.

The term heterocycloalkyl is defined similarly as cycloalkyl, but can contain O, S, or N heteroatoms or combinations thereof within the cyclic backbone. A range of these groups useful with the compounds and methods described herein includes $C_4$-$C_9$ heterocycloalkyl.

Aryl groups include, for example, phenyl and substituted phenyl. Heteroaryl groups contain O, N, or S heteroatoms, either alone or in combination in five or six membered rings. Examples of heteroaryl groups with one heteroatom include pyridyl, thienyl, and furyl substituted on or joined by any of the available carbon atoms. Examples of heteroaryl groups with more than one heteroatom include pyrimidinyl, oxazolyl, and thiazolyl substituted on or joined by any of the available carbon atoms. Aryl and heteroaryl groups can include additional fused rings. Examples of such groups include indanyl, naphthyl, benzothienyl, quinolinyl, and isomers thereof substituted on or joined by any of the available carbon atoms.

All groups mentioned above can be unsubstituted or substituted with one or more of the following which may the same or different. Examples of appropriate substituents include, but are not limited to, the following: alkoxy (e.g., methoxy), alkyl, aryl, carboxylate, carboxylate ester, cyano, halogen (e.g., chloro, bromo, fluoro, iodo), heteroaryl, nitro, amino, alkylsulfonyl, sulfonamide, reverse sulfonamide, and thio.

In some examples, Formula I is represented by Structure I-A:

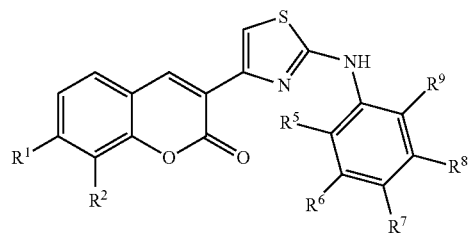

In Structure I-A, $R^1$ and $R^2$ are as defined above for Formula I.

Also in Structure I-A, $R^5$, $R^6$, $R^7$, $R^8$, and $R^9$ are each independently selected from hydrogen, halogen, hydroxyl, substituted or unsubstituted alkoxy, cyano, nitro, trifluoromethyl, substituted or unsubstituted carbonyl, substituted or unsubstituted amino, substituted or unsubstituted $C_{1-6}$ alkyl, substituted or unsubstituted $C_{2-6}$ alkenyl, substituted or unsubstituted aryl, substituted or unsubstituted sulfonamide, substituted or unsubstituted sulfonyl, or substituted or unsubstituted thio. The carbonyl can be a carboxylic acid or an acid derivative. As used herein, an acid derivative refers to a functional derivative of a carboxylic acid such as, for example, an ester or an amide.

In some examples, Formula I is represented by Structure I-B:

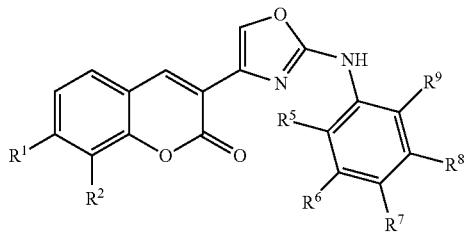

In Structure I-B, $R^1$ and $R^2$ are as defined above for Formula I.

Also in Structure I-B, $R^5$, $R^6$, $R^7$, $R^8$, and $R^9$ are as defined above for Structure I-A.

In some examples, Formula I is represented by Structure I-C:

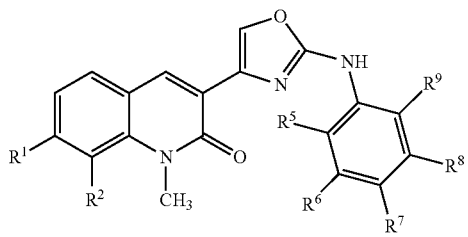

In Structure I-C, $R^1$ and $R^2$ are as defined above for Formula I.

Also in Structure I-C, $R^5$, $R^6$, $R^7$, $R^8$, and $R^9$ are as defined above for Structure I-A.

In some examples, Formula I is represented by Structure I-D:

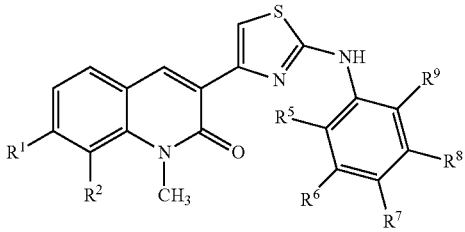

In Structure I-D, $R^1$ and $R^2$ are as defined above for Formula I.

Also in Structure I-D, $R^5$, $R^6$, $R^7$, $R^8$, and $R^9$ are as defined above for Structure I-A.

Optionally, adjacent R groups in Structures I-A, I-B, I-C, and I-D, e.g., $R^1$ and $R^2$, $R^5$ and $R^6$, $R^6$ and $R^7$, $R^7$ and $R^8$, or $R^8$ and $R^9$ can be combined to form a substituted or unsubstituted aryl, substituted or unsubstituted cycloalkenyl, substituted or unsubstituted heteroaryl, or substituted or unsubstituted heterocycloalkyl.

Examples of Formula I include the following compounds:

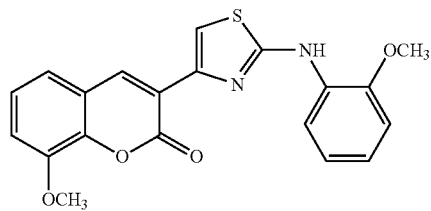

43H11 (DBM 101) (001_2)

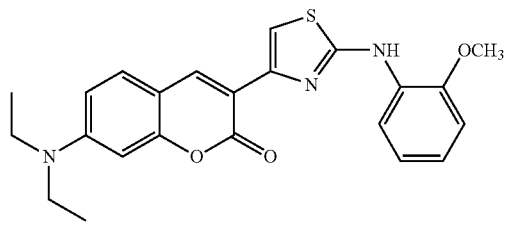

001_5

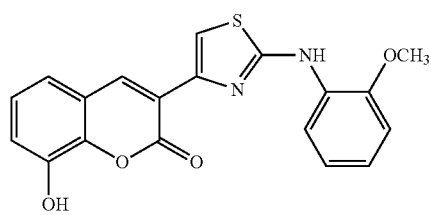

001_6

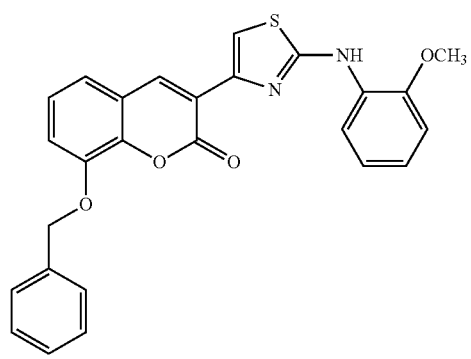

001_7

-continued
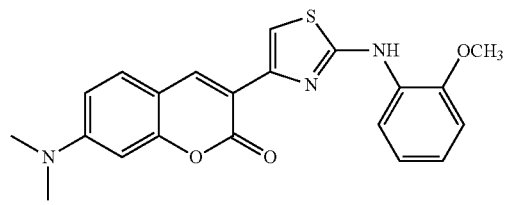
002_N7_11
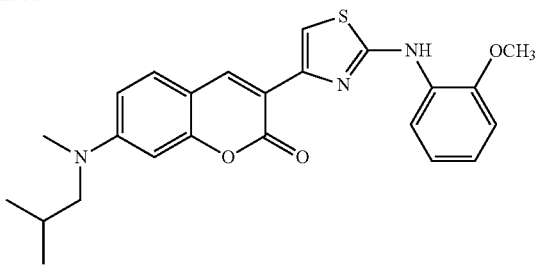
002_N7_13
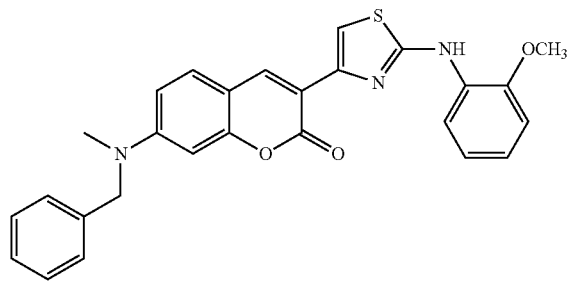
002_N7_14
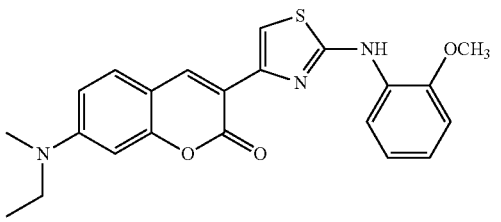
002_N7_21
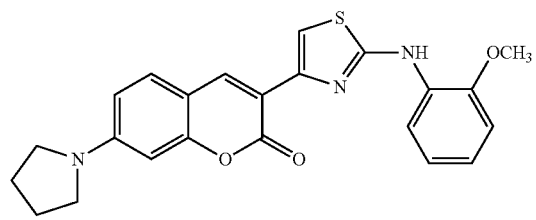
002_N7_22
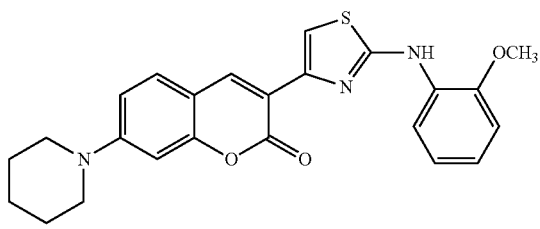
002_N7_23
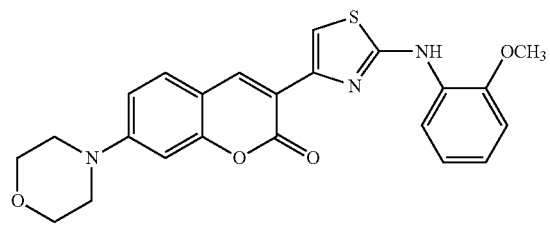
002_N7_26
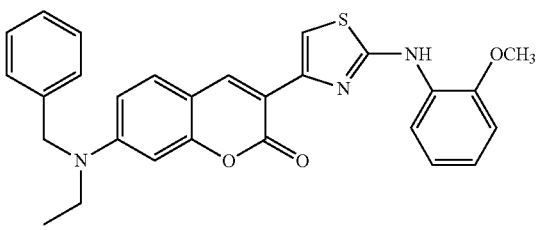
002_N7_29
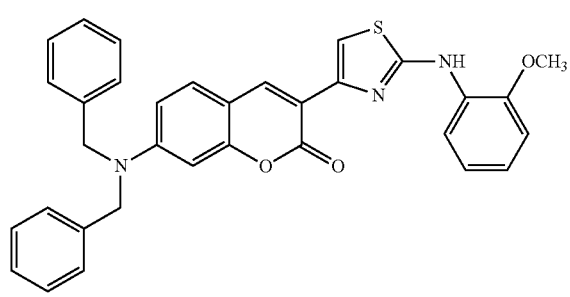
002_N7_31
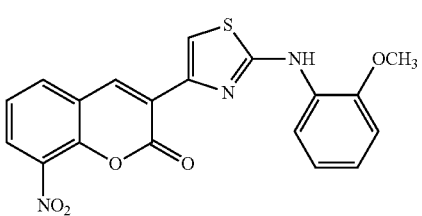
002_N8_27 (DBM227)
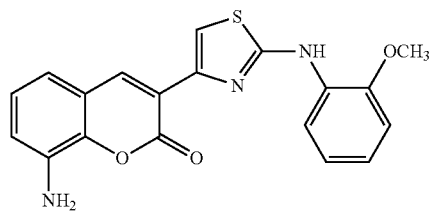
002_N8_28 (DBM228)
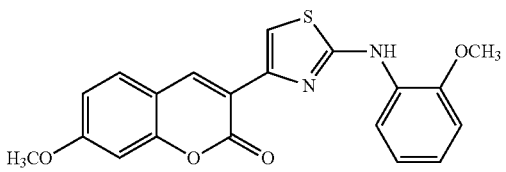
002_07_1

-continued
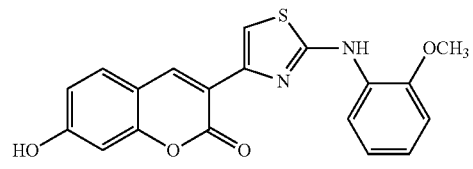
002_07_11
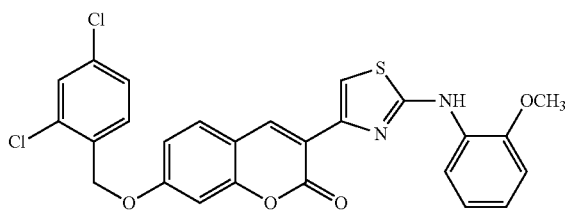
002_07_12
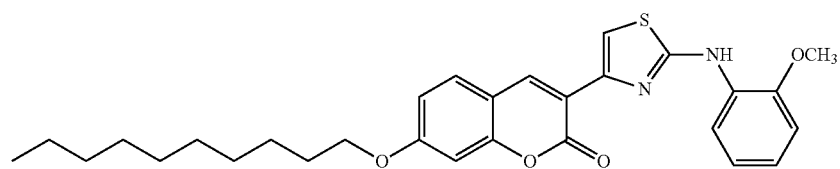
002_07_13
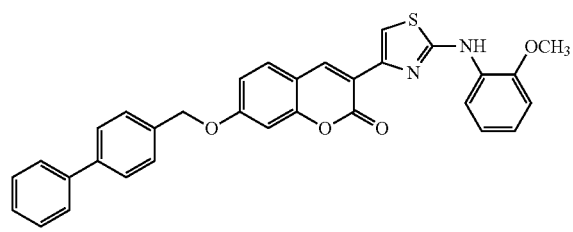
002_07_14
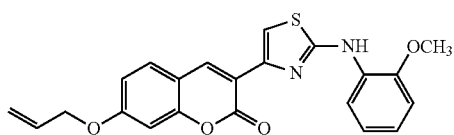
002_07_15
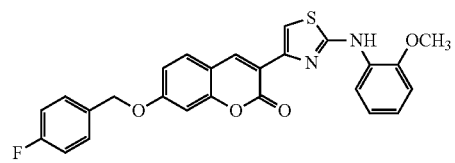
002_07_17
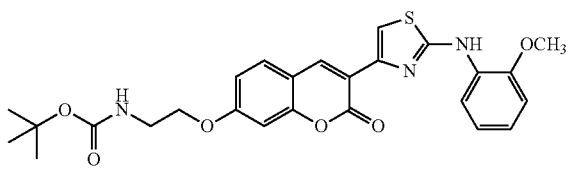
002_07_18
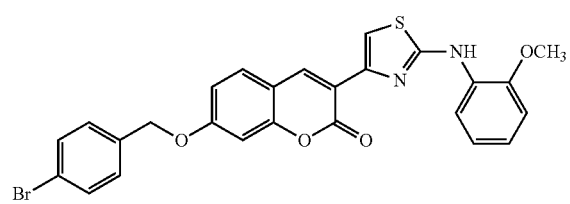
002_07_19
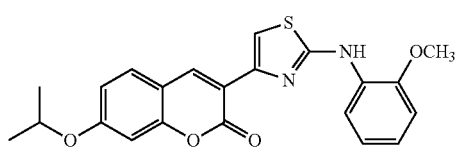
002_07_2
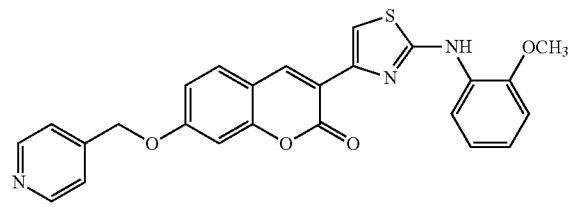
002_07_20
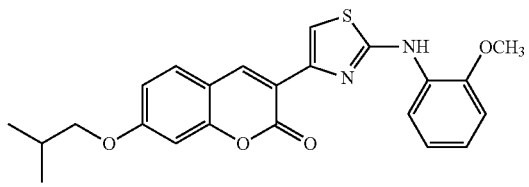
002_07_3
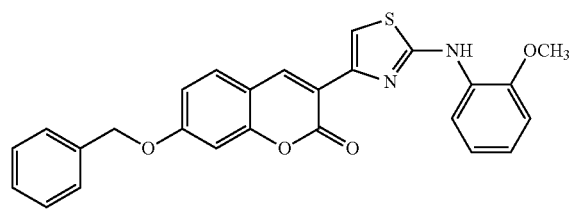
002_07_4
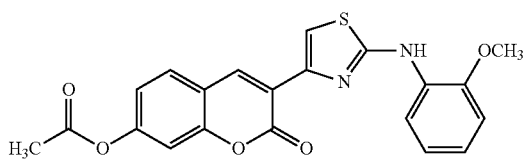
002_07_6

-continued
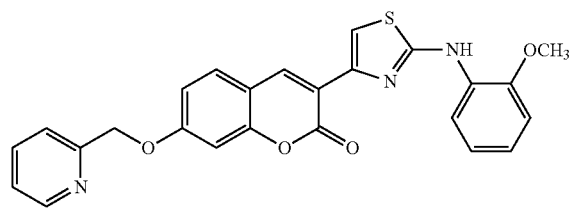
002_07_7
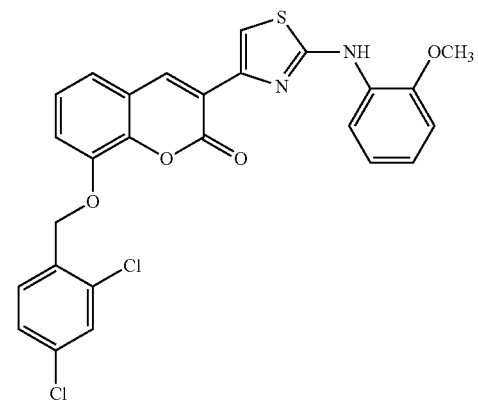
002_07_8
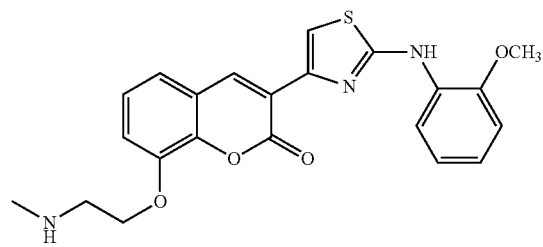
002_08_10
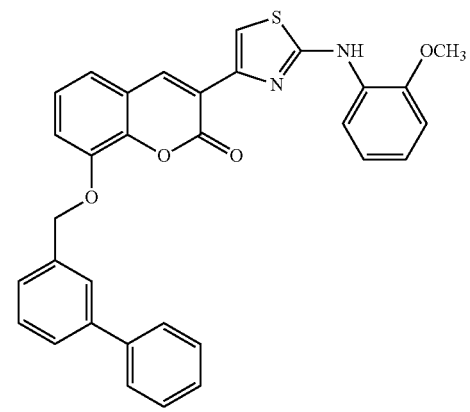
002_08_12
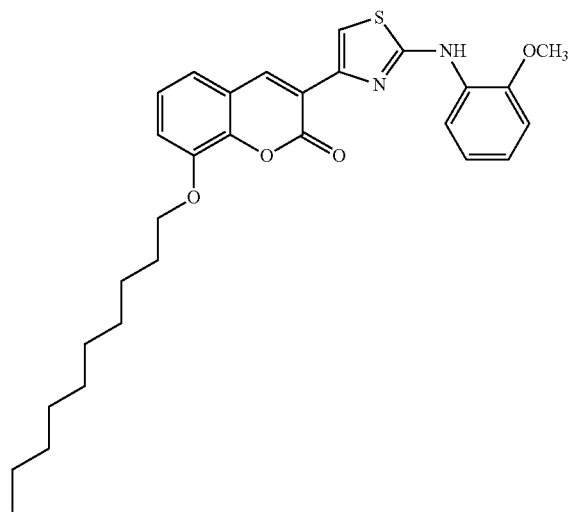
002_08_13
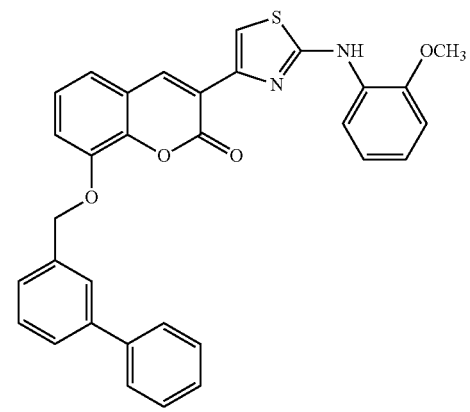
002_08_14
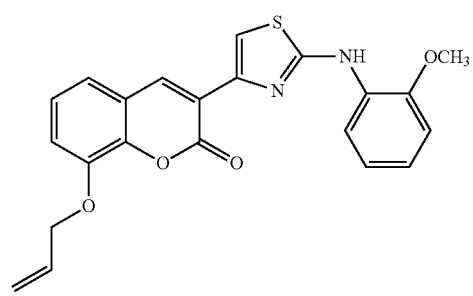
002_08_15
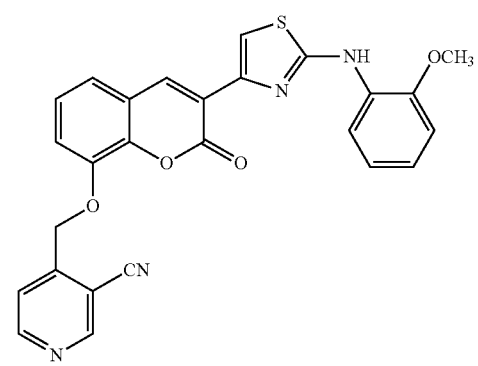
002_08_16

-continued
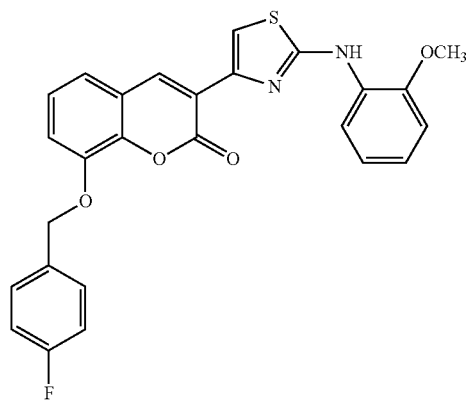
002_08_17
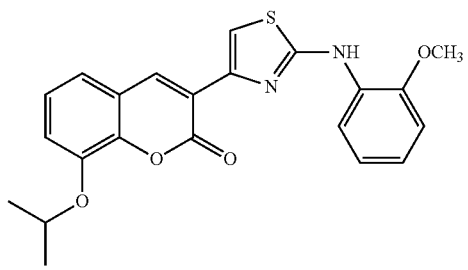
002_08_2
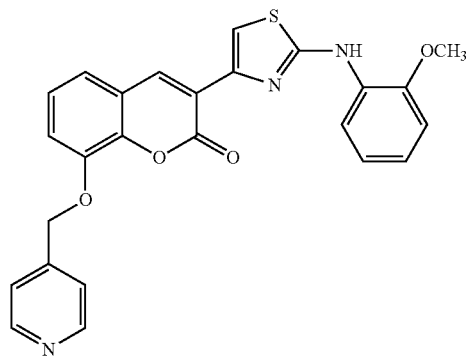
002_08_20
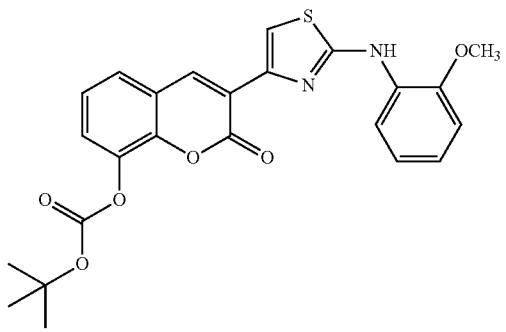
002_08_21
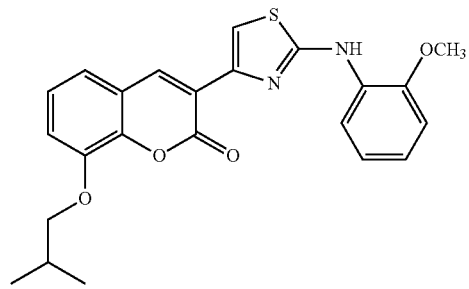
002_08_3
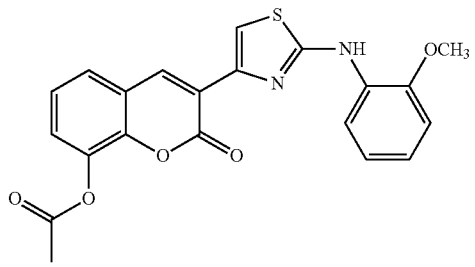
002_08_6
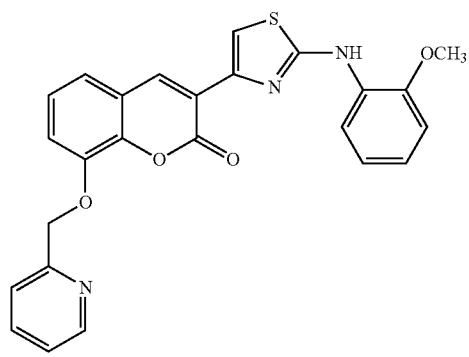
002_08_7
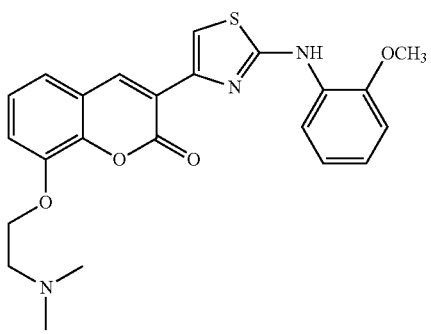
002_08_8

-continued
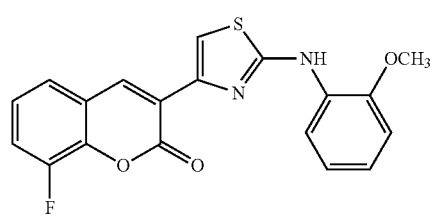
DBM-003-8F
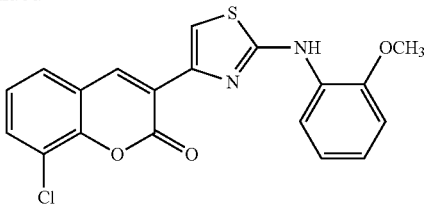
DBM-003-8Cl (DBM 308)
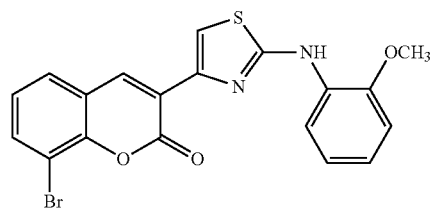
DBM-003-8Br (DBM 318)
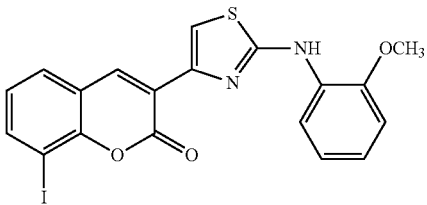
DBM-003-8I
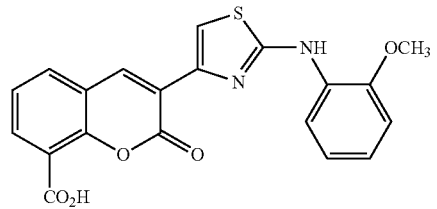
DBM-003-8COOH (DBM 328)
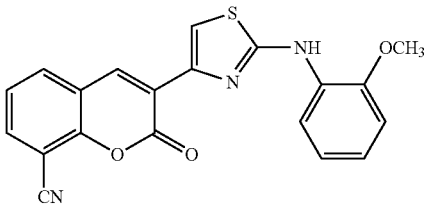
DBM-003-8CN
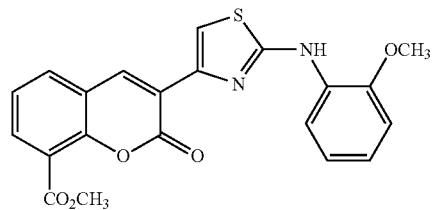
DBM-003-8COOCH₃
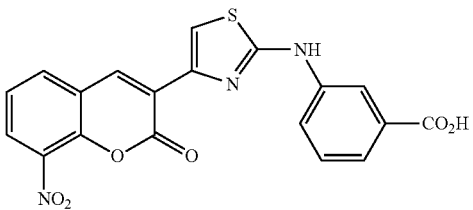
DBM-003-TU4
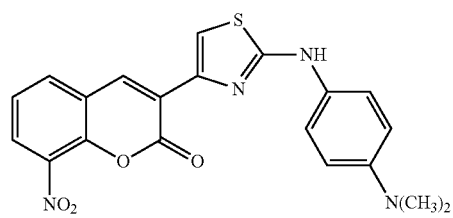
DBM-003-TU31
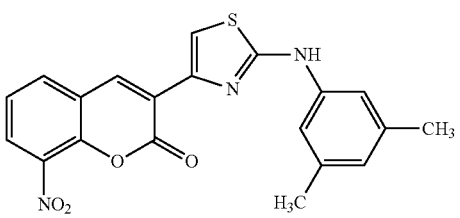
DBM-003-TU16
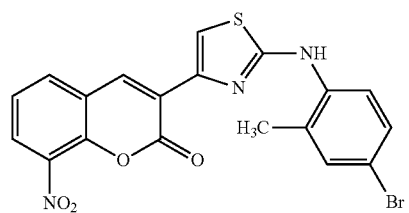
DBM-003-TU21
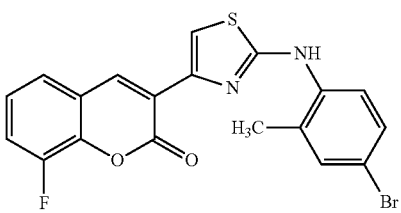
DBM-003-TU21-F
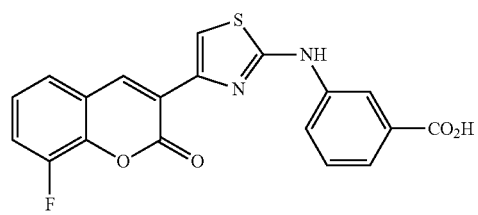
DBM-003-TU4-F
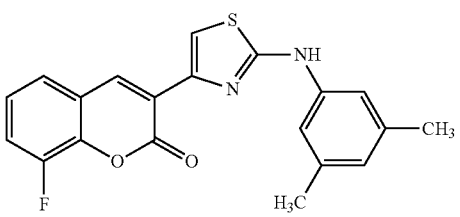
DBM-003-TU16-F -continued
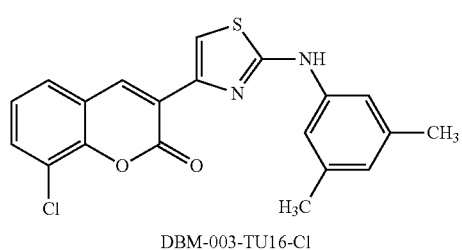
DBM-003-TU16-Cl
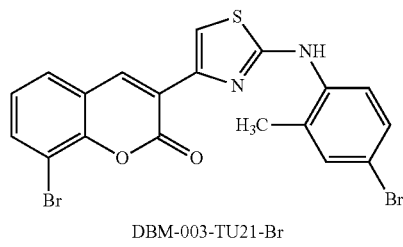
DBM-003-TU21-Br
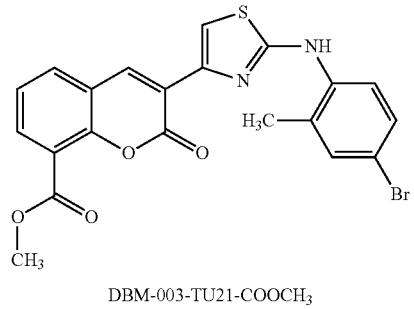
DBM-003-TU21-COOCH₃
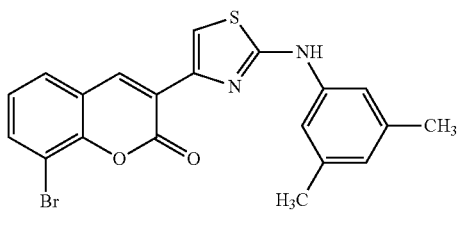
DBM-003-TU16-Br
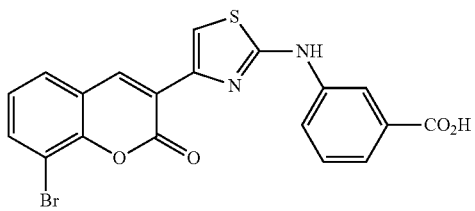
DBM-003-TU4-Br
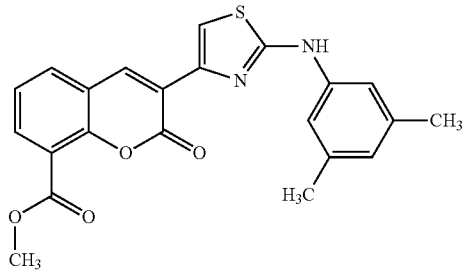
DBM-003-TU16-COOCH₃
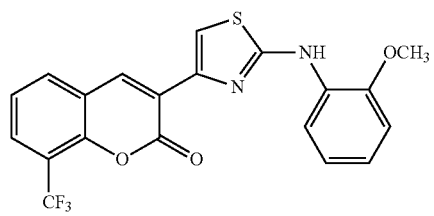
007-01 (DBM-701)
007-02
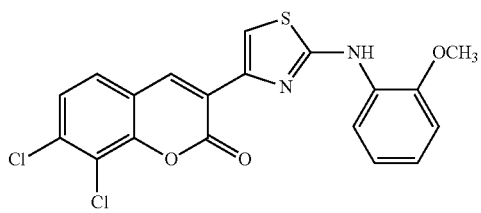
0007-03
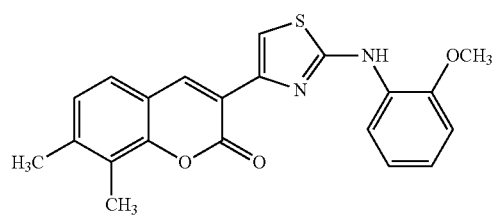
004-04
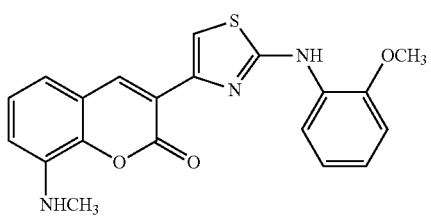
004-05
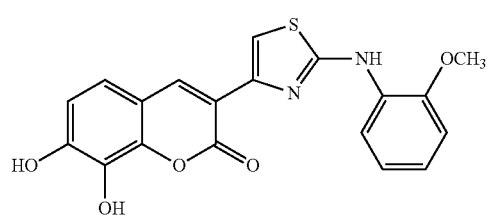
004-06
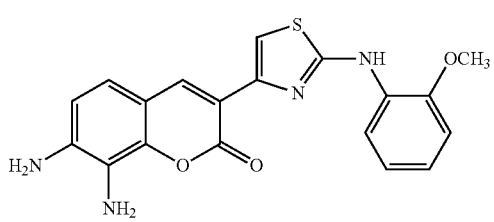

-continued
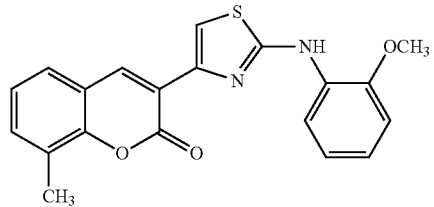
004-07 (DBM 707)
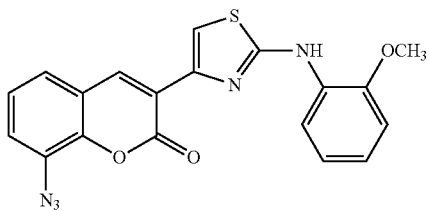
004-09
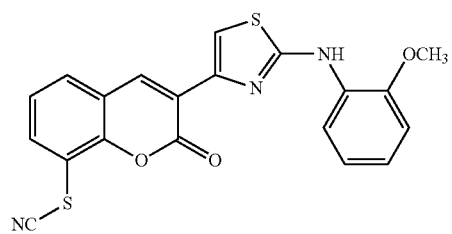
004-10
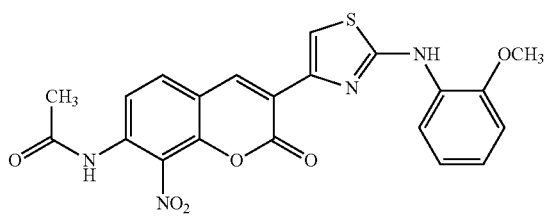
004-14
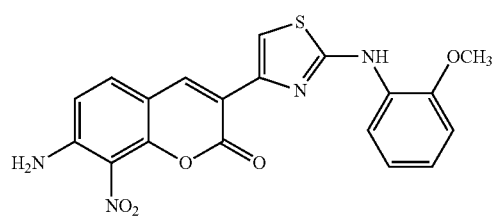
004-15 (DBM 715)
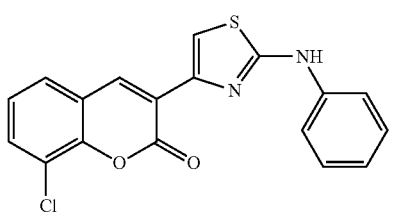
DBM-E-01
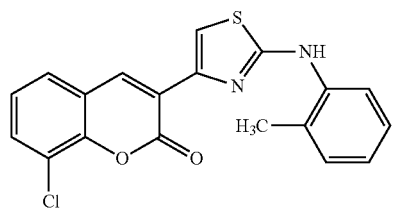
DBM-E-02
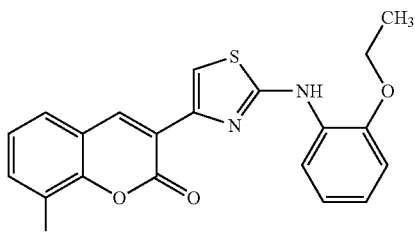
DBM E-03
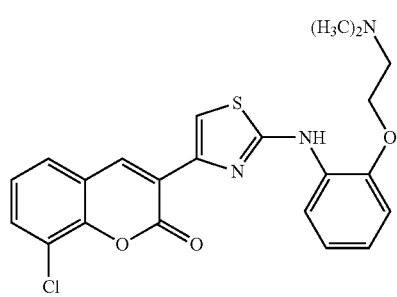
EBM-E-04
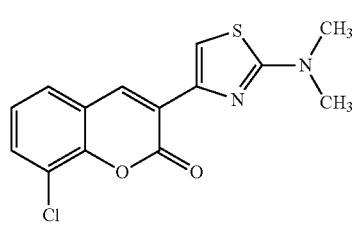
DBM-E-05.1
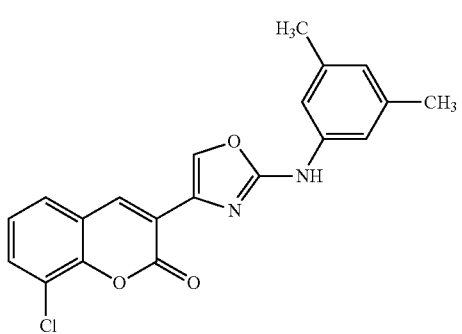
DBM-E-05
DBM-E-06

-continued
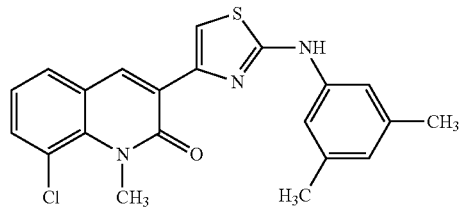
DBM-E-07
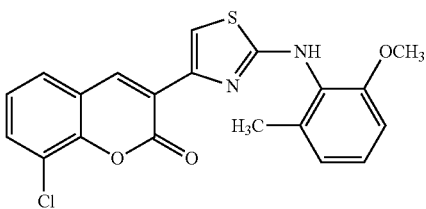
DBM-E-11
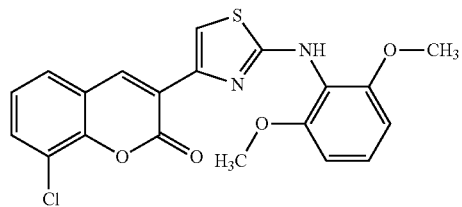
DBM-E-12
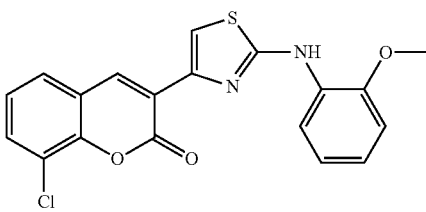
DBM-E-13
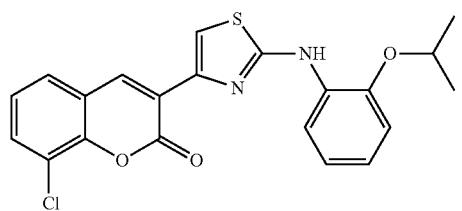
DBM-E-14
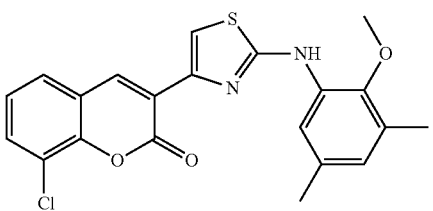
DBM-E-15
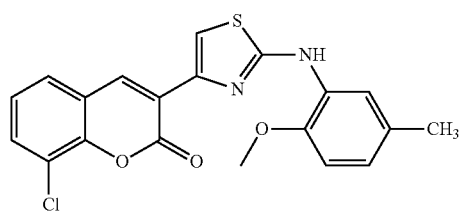
DBM-E-16
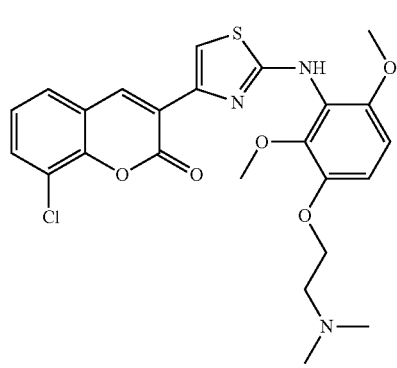
DBM-E-18
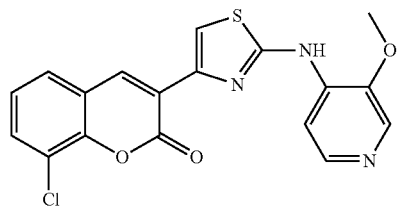
DBM-E-20
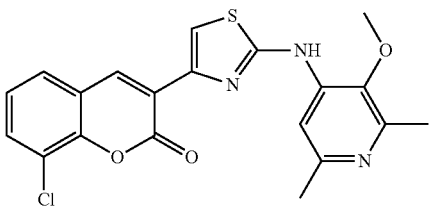
DBM-E-21

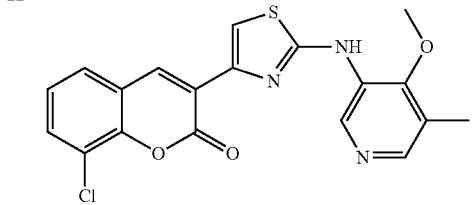
-continued
DBM-E-22
DBM-E-23
P1
P2
P3
P4
P5
P6
P7
P8
P9
P10
P11
P12
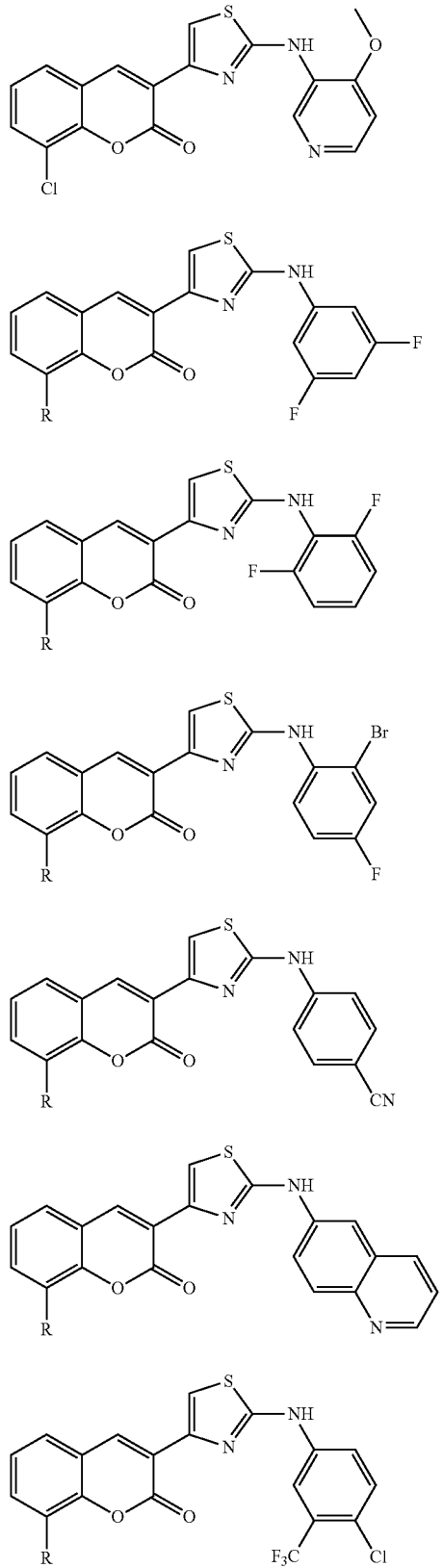

-continued
P13
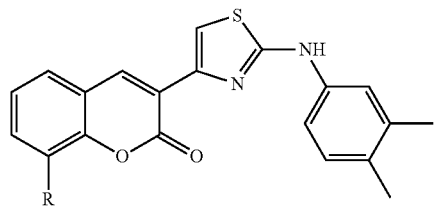
P14
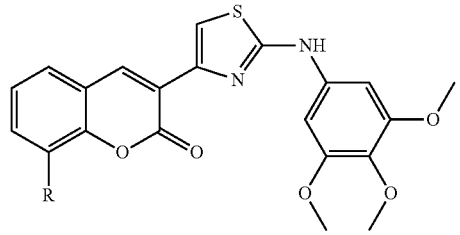
P15
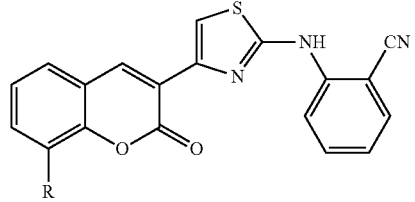
P16
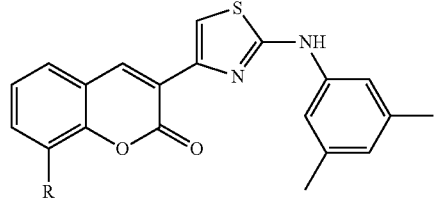
P17
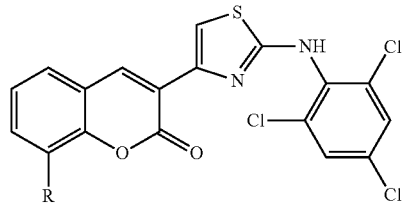
P18
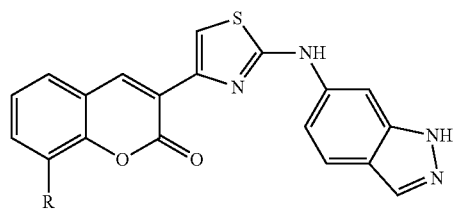
P19
P20
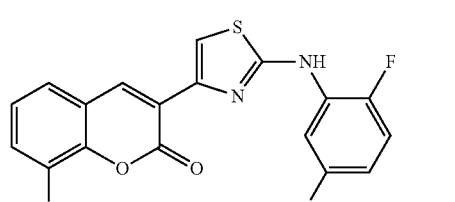
P21
P22
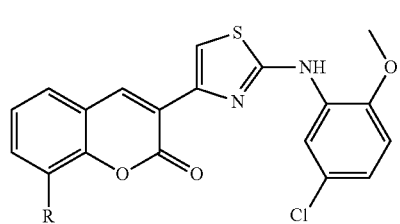
P23
P24
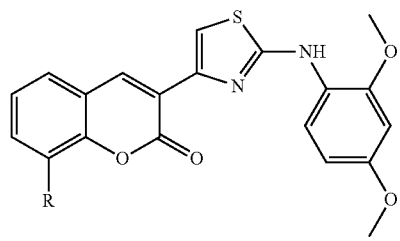
P25
P26

-continued
P27
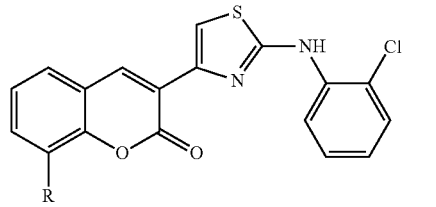
P28
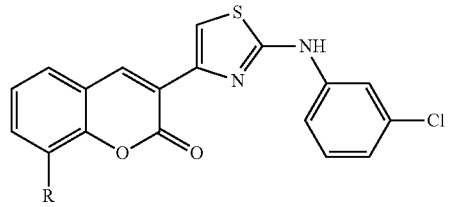
P29
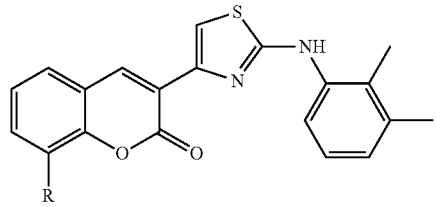
P30
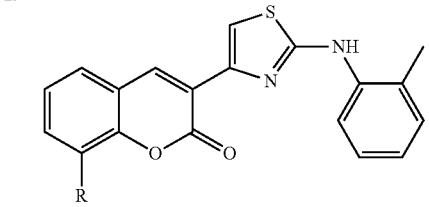
P31
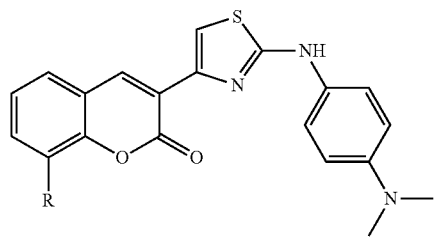
P32
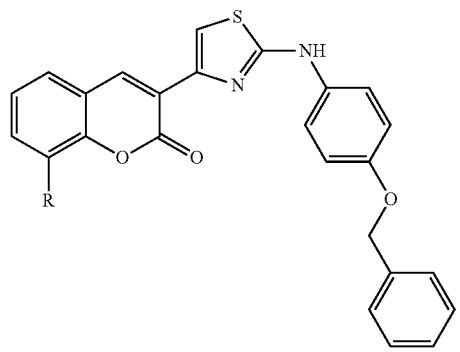
P33
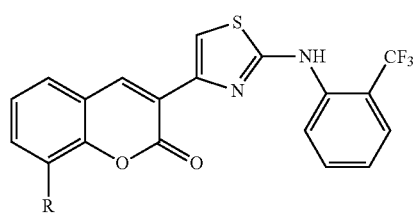
P34
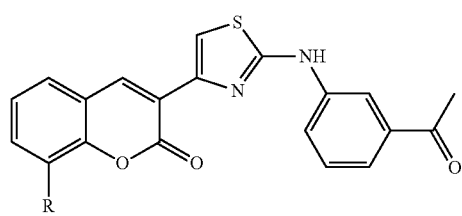
P35
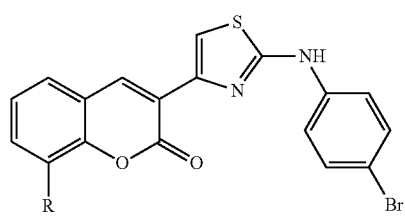
P36
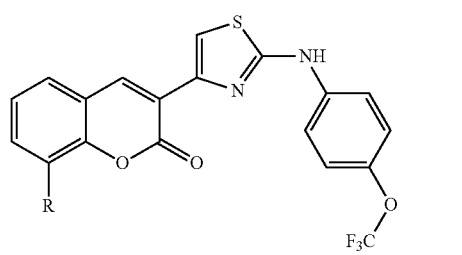
P37
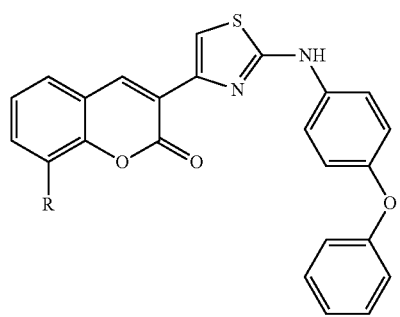
P38
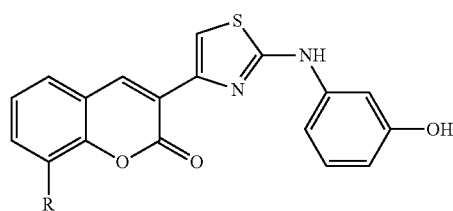

-continued
P39
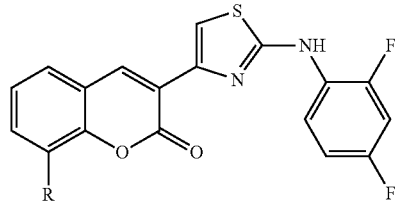
P40
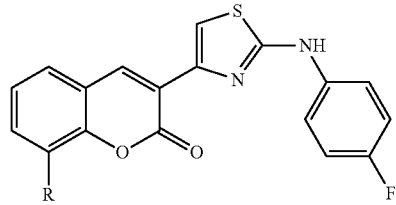
P41
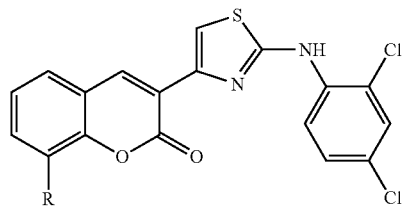
P42
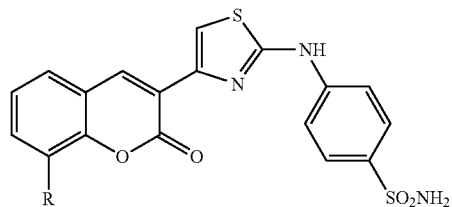
P43
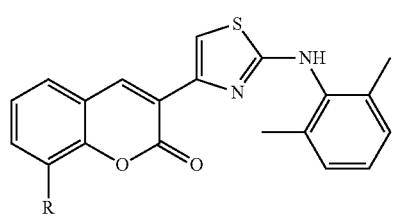
P44
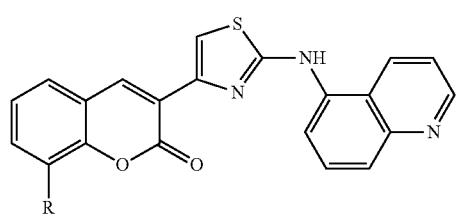
P45
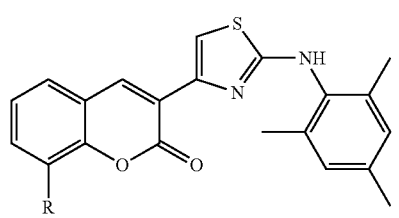
P46
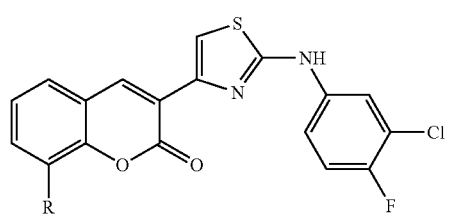
P47
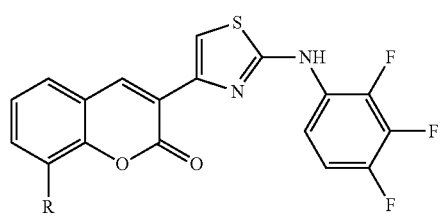
P48
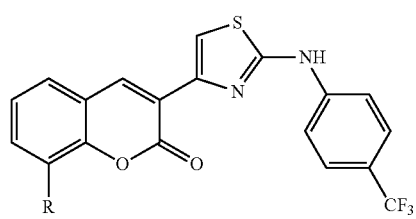
P49
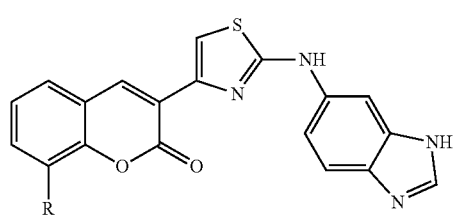
P50
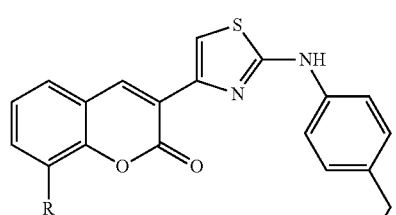
P51
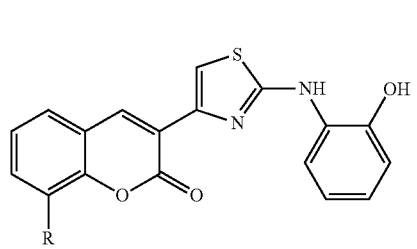
P52
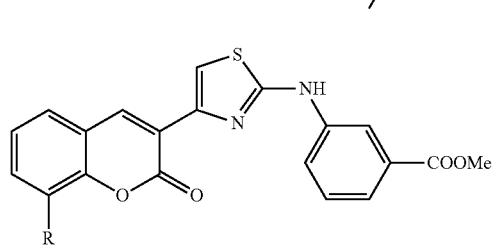

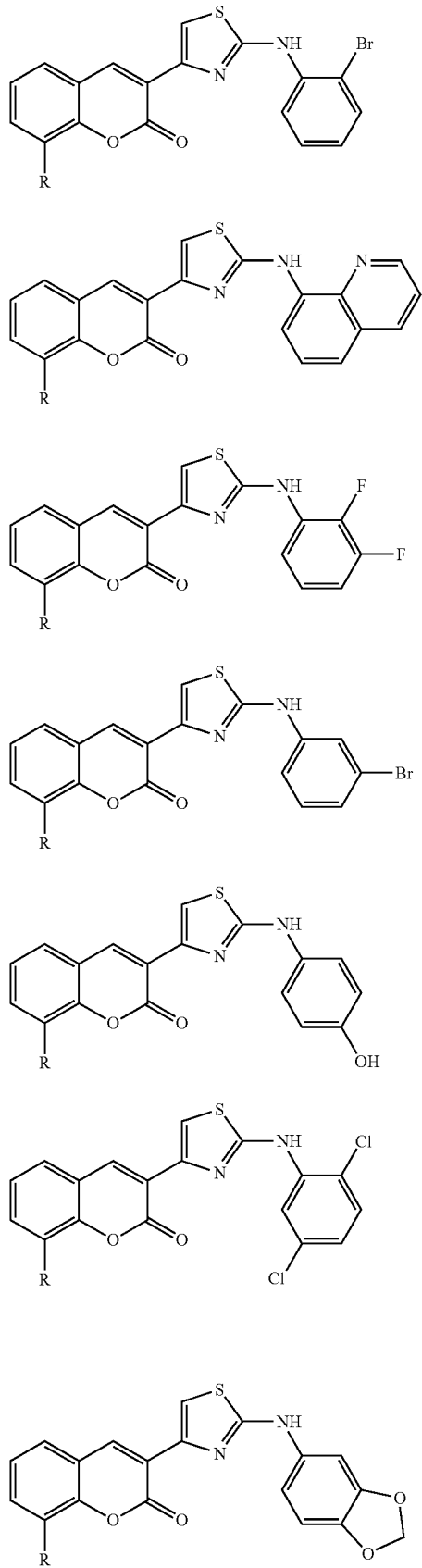

-continued
P67
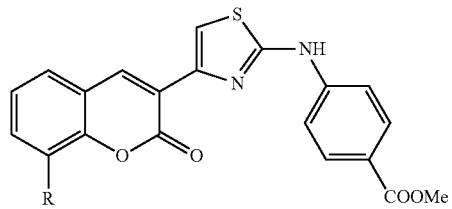
P68
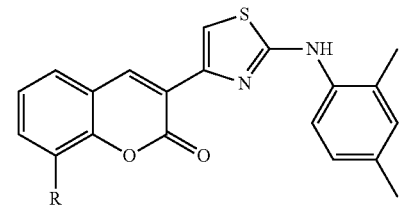
P69
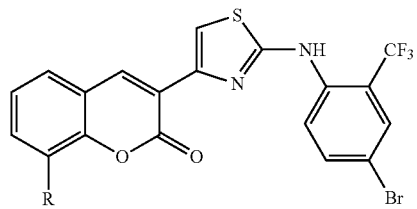
P70
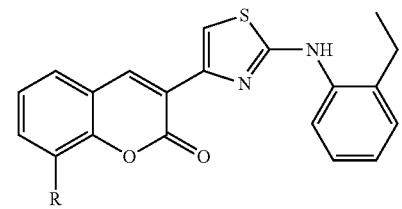
P71
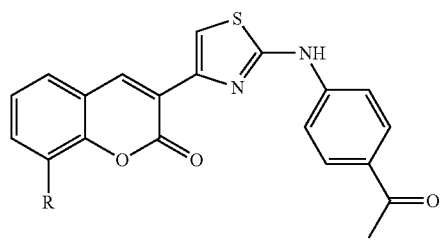
P72
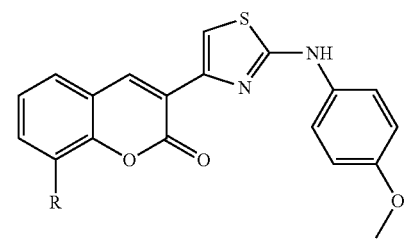
P73
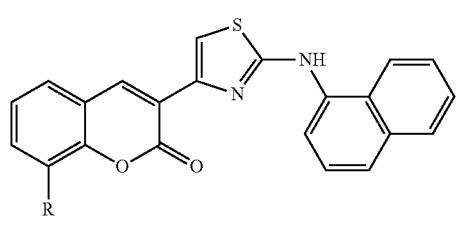
P74
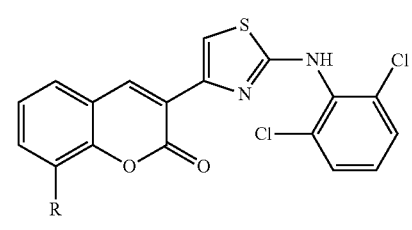
P75
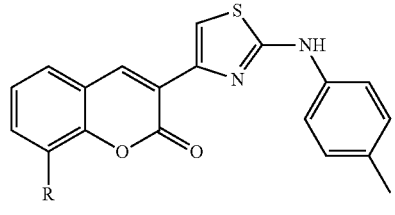
P76
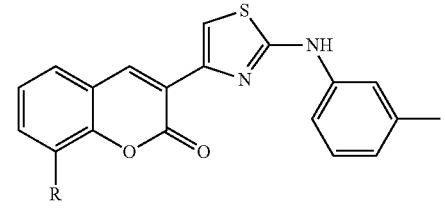
P77
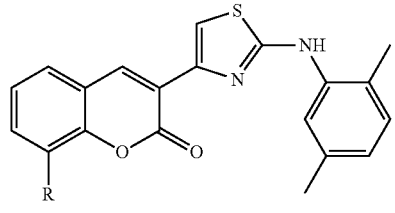
P78
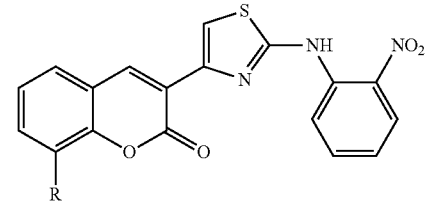
P79
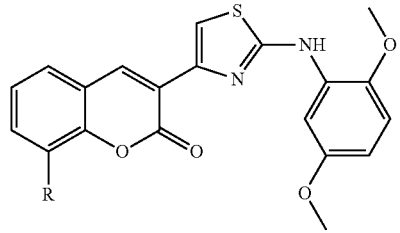
P80
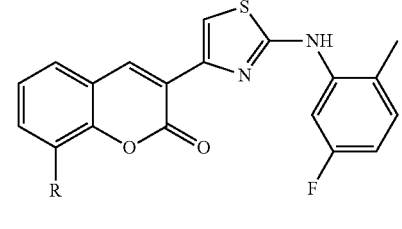

-continued
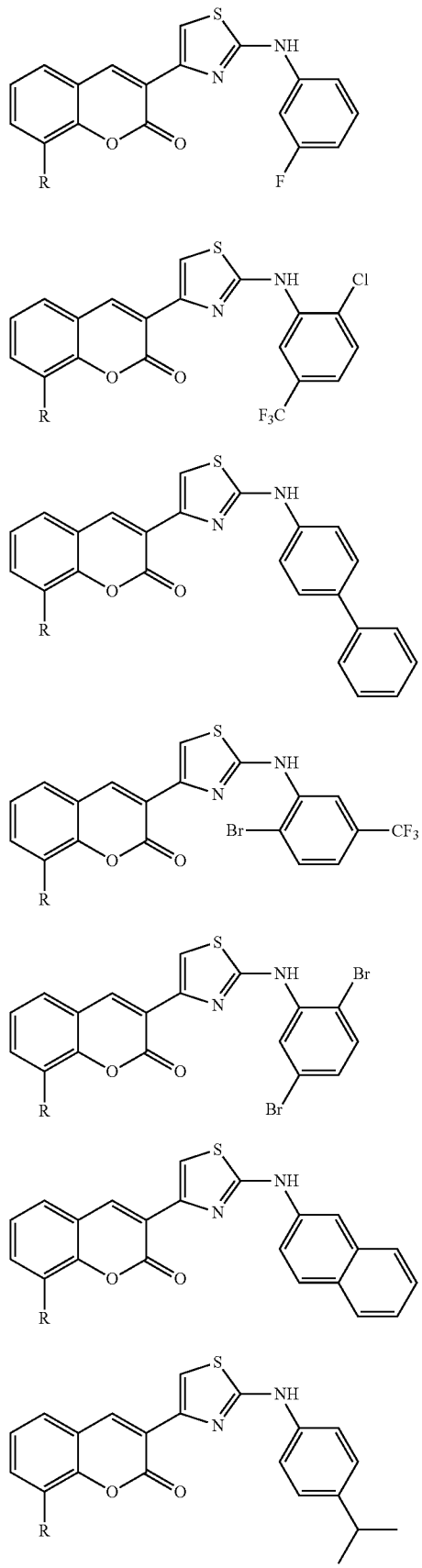
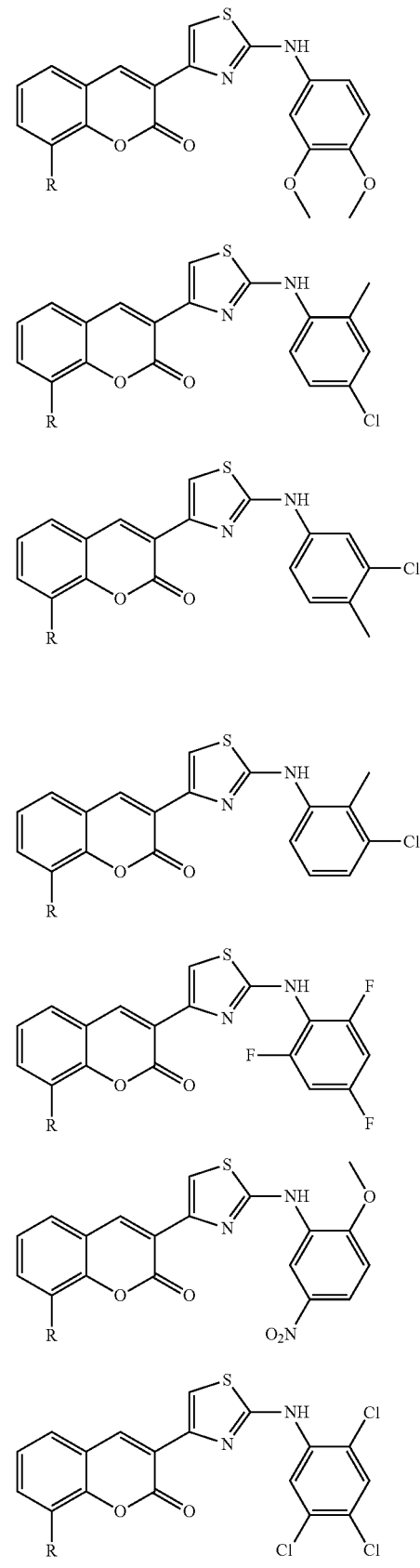

P95 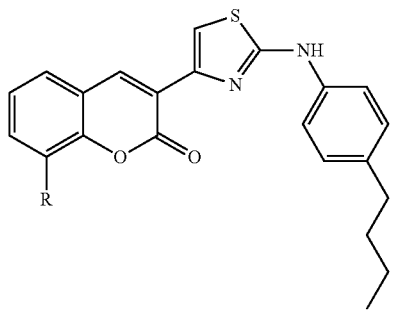
P96 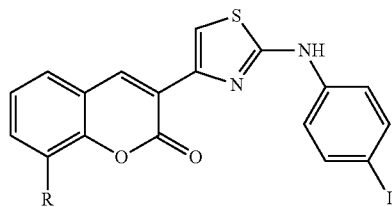
P97 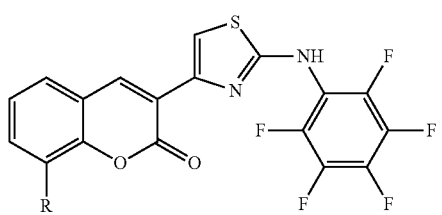
P98 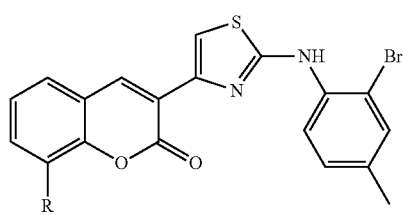
P99 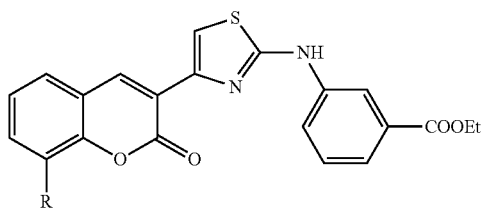
P100 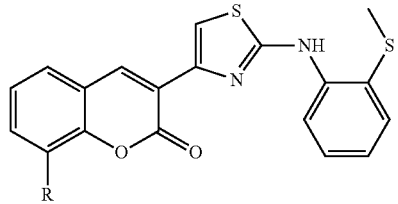
P101 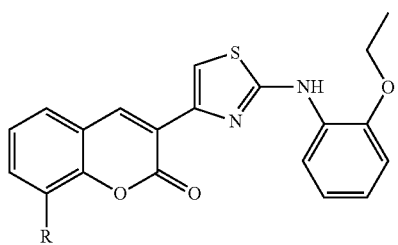
P102 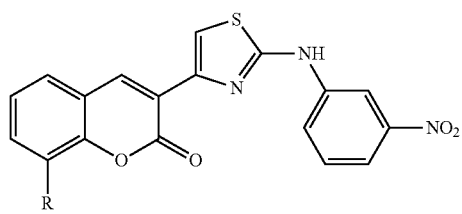
P103 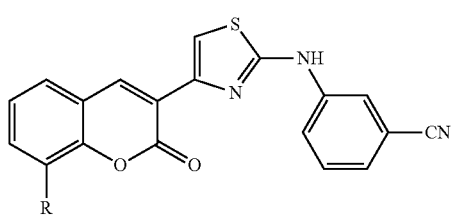
P104 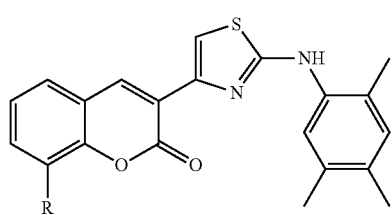
P105 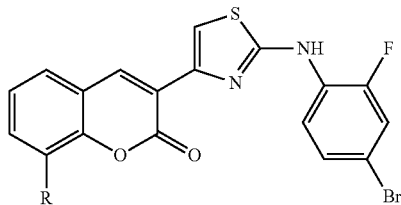
P106 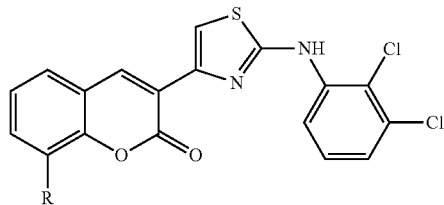

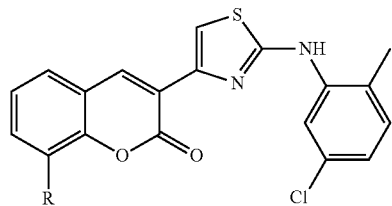
P107

In Compounds P1 through P107, R can be halogen (e.g., chloro).

A class of coumarin derivatives described herein is represented by Formula II:

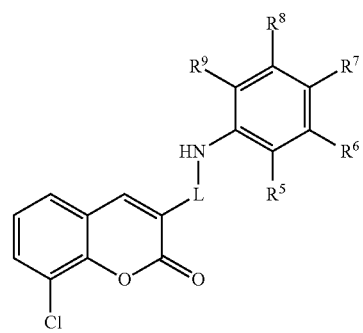

and pharmaceutically acceptable salts or prodrugs thereof.

In Formula II, L is a heteroaryl.

Also, in Formula II, $R^5$, $R^6$, $R^7$, $R^8$, and $R^9$ are each independently selected from hydrogen and methoxy.

In some examples, Formula II is represented by Structure II-A:

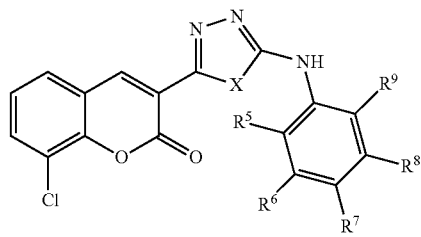

In Structure II-A, X is NH or O.

Also in Structure II-A, $R^5$, $R^6$, $R^7$, $R^8$, and $R^9$ are as defined above for Formula II.

In some examples, Formula II is represented by Structure II-B:

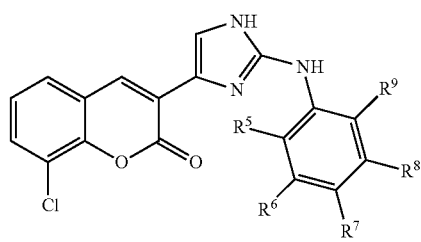

In Structure II-B, $R^5$, $R^6$, $R^7$, $R^8$, and $R^9$ are as defined above for Formula II.

In some examples, Formula II is represented by Structure II-C:

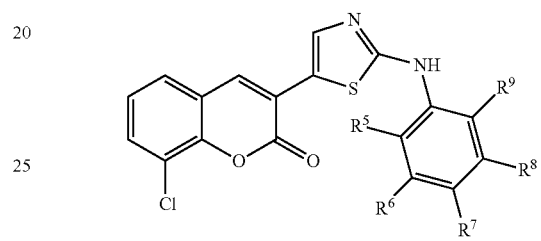

In Structure II-C, $R^5$, $R^6$, $R^7$, $R^8$, and $R^9$ are as defined above for Formula II.

Examples of Formula II include the following compounds:

Compound II-1

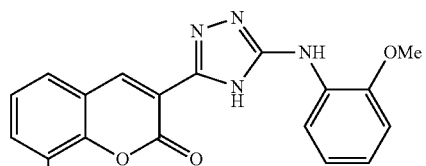

Compound II-2

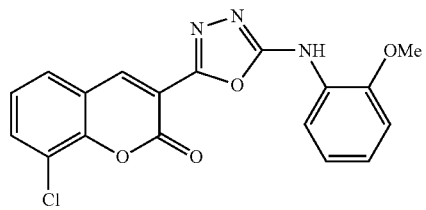

Compound II-3

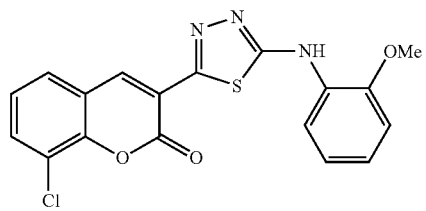

-continued

Compound II-4

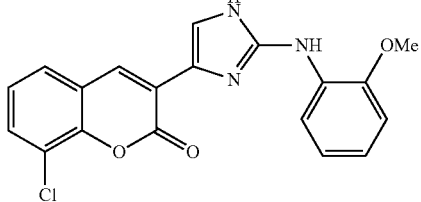

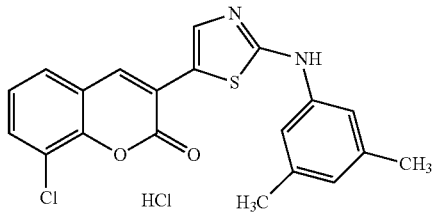

DBM-E-10

A class of coumarin derivatives described herein is represented by Formula III:

III

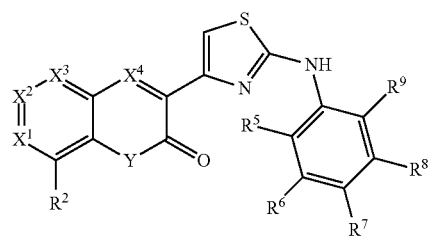

and pharmaceutically acceptable salts or prodrugs thereof.

In Formula III, $X^1$, $X^2$, $X^3$ and $X^4$ are each independently selected from CH and N.

Also, in Formula III, Y is O or NR, where R is hydrogen or methyl.

Additionally, in Formula III, $R^2$ is hydrogen, $C_{1-6}$ alkyl, halogen, or trifluoroalkyl. Optionally, $R^2$ is Cl or methyl.

Further, in Formula III, $R^5$, $R^6$, $R^7$, $R^8$, and $R^9$ are each independently selected from hydrogen and methoxy.

In some examples, Formula III is represented by Structure III-A:

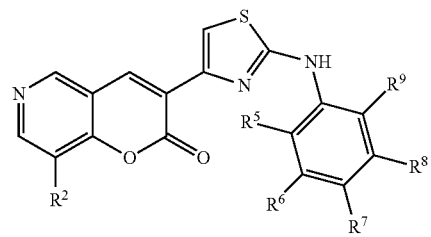

In Structure III-A, $R^2$, $R^5$, $R^6$, $R^7$, $R^8$, and $R^9$ are as defined above for Formula III.

In some examples, Formula III is represented by Structure III-B:

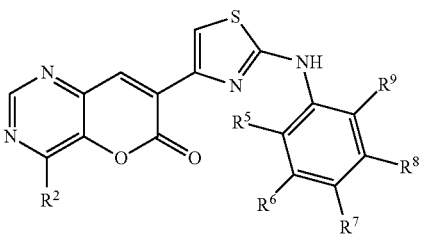

In Structure III-B, $R^2$, $R^5$, $R^6$, $R^7$, $R^8$, and $R^9$ are as defined above for Formula III.

In some examples, Formula III is represented by Structure III-C:

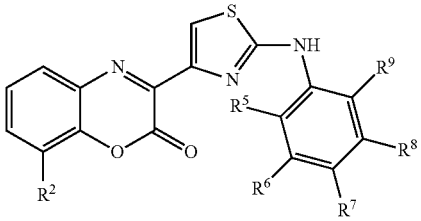

In Structure III-C, $R^2$, $R^5$, $R^6$, $R^7$, $R^8$, and $R^9$ are as defined above for Formula III.

In some examples, Formula III is represented by Structure III-D:

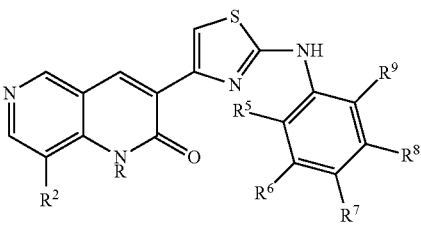

In Structure III-D, R is hydrogen or methyl.

Also, in Structure III-D, $R^2$, $R^5$, $R^6$, $R^7$, $R^8$, and $R^9$ are as defined above for Formula III.

Examples of Formula III include the following compounds:

Compound III-1

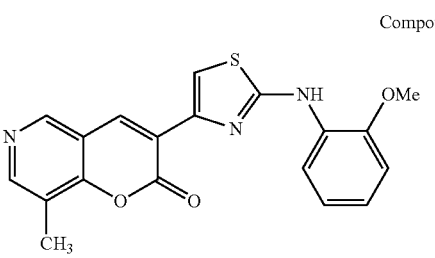

Compound III-2

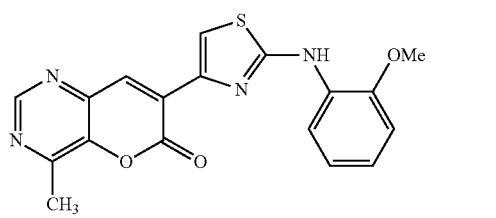

Compound III-3

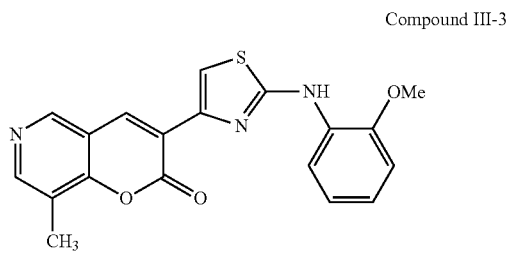

Compound III-4

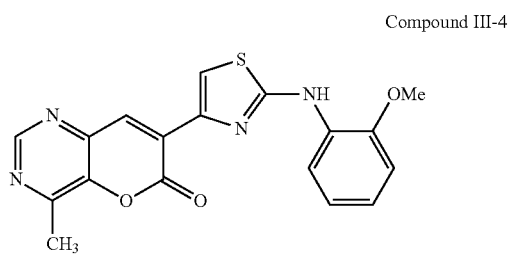

A class of coumarin derivatives described herein is represented by Formula IV:

IV

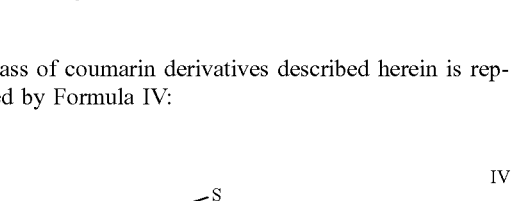

and pharmaceutically acceptable salts or prodrugs thereof.

In Formula IV, $X^1$ is O or $NCH_3$.

Also, in Formula IV, $X^2$ is CH or N.

Additionally, in Formula IV, Y is O, NH, or $NCH_3$.

Further, in Formula IV, $R^5$, $R^6$, $R^7$, $R^8$, and $R^9$ are each independently selected from hydrogen and methoxy.

Examples of Formula IV include the following compounds:

Compound IV-1

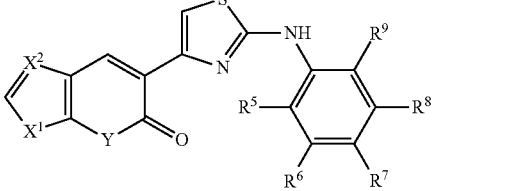

Compound IV-2

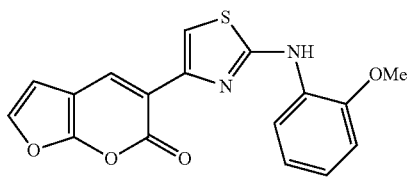

Compound IV-3

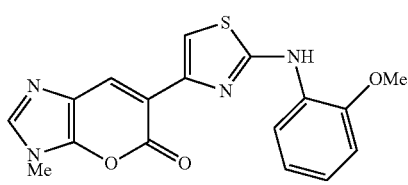

Compound IV-4

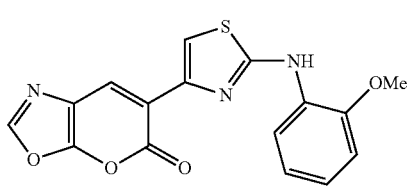

Compound IV-5

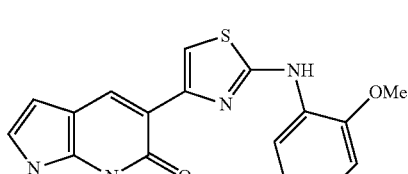

Compound IV-6

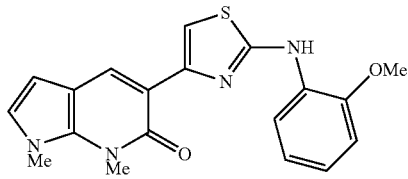

Compound IV-7

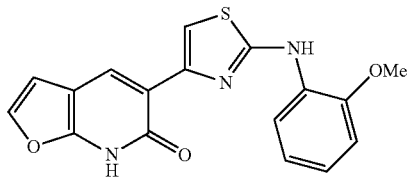

Compound IV-8

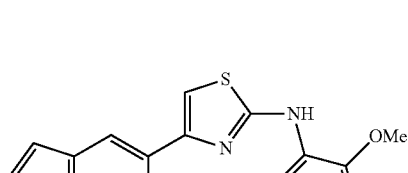

A class of coumarin derivatives described herein is represented by Formula V:

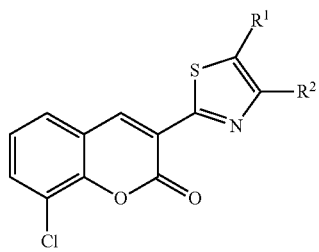

V and pharmaceutically acceptable salts or prodrugs thereof.

In Formula V, $R^1$ and $R^2$ are each independently selected from hydrogen, substituted or unsubstituted amino, and substituted or unsubstituted carbonyl.

Examples of Formula V include the following compounds:

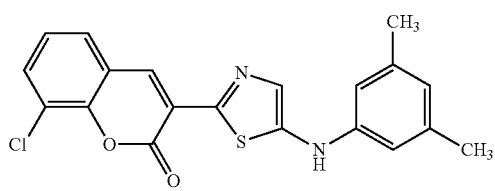

DBM-E-08

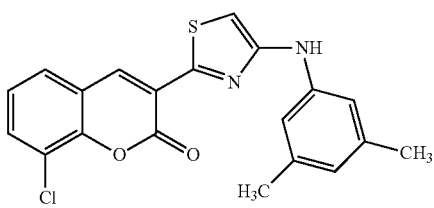

DBM-E-09

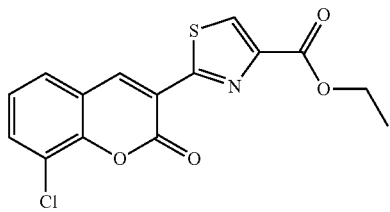

DBM-E-09.1

A class of coumarin derivatives described herein is represented by Formula VI:

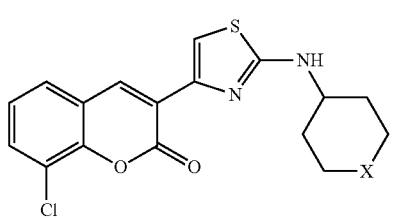

VI and pharmaceutically acceptable salts or prodrugs thereof.

In Formula VI, X is $CH_2$, NH, or O.

Examples of Formula VI include the following compounds:

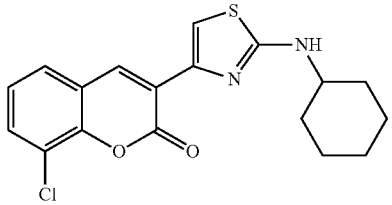

Compound VI-1

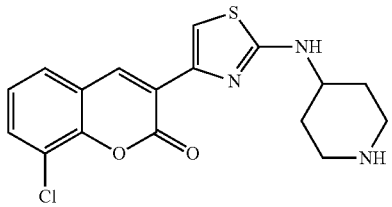

Compound VI-2

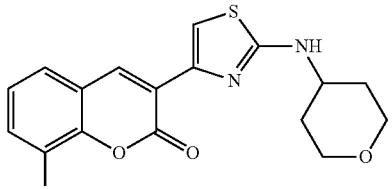

Compound VI-3

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formulas I-VI include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene, et al., Protective Groups in Organic Synthesis, 2d. Ed., Wiley & Sons, 1991, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

III. Pharmaceutical Formulations

One or more of the compounds described herein or pharmaceutically acceptable salts or prodrugs thereof can be provided in a pharmaceutical composition comprising a pharmaceutical carrier. Furthermore, the one or more compounds described herein can be combined with other agents, including treatments for lung, digestive, hepatic, and biliary tract related diseases and disorders. For example, in the case of cystic fibrosis, the compounds described herein can be combined with mucus thinning drugs (e.g., dornase alfa, N-Acetyl cysteine, and hypertonic saline), bronchodilators (e.g., metaproterenol sulfate, pirbuterol acetate, salmeterol, albuterol, and terbutaline sulfate), P2Y2-receptor agonists (e.g., denufosol), and agents that target nonsense mutations (e.g., PTC124). Further examples of additional agents that can be combined with the compounds described herein include antibiotics (e.g., aminoglycosides, antipseudomonal penicillins, and cephalosporins), antimicrobial drugs (e.g., rifabutin), ethambutol, clarithromycin, clofazimine, aztreonam, steroidal and nonsteroidal anti-inflammatory drugs (e.g., ibuprofen and prednisone), pentoxifylline, dornase alfa, or ursodeoxycholic acid.

The one or more compounds described herein can be provided as pharmaceutical compositions administered in combination with one or more other therapeutic or prophylactic agents. As used throughout, a therapeutic agent is a compound or composition effective in ameliorating a pathological condition. Illustrative examples of therapeutic agents include, but are not limited to, chemotherapeutic agents, anti-viral agents, anti-opportunistic agents, antibiotics, and immunostimulatory agents. Optionally, more than one therapeutic agent is administered in combination with the provided compositions.

The one or more compounds described herein, with or without additional agents, can be provided in the form of an inhaler or nebulizer for inhalation therapy. As used herein, inhalation therapy refers to the delivery of a therapeutic agent, such as the compounds described herein, in an aerosol form to the respiratory tract (i.e., pulmonary delivery). As used herein, the term aerosol refers to very fine liquid or solid particles carried by a propellant gas under pressure to a site of therapeutic application. When a pharmaceutical aerosol is employed, the aerosol contains the one or more compounds described herein, which can be dissolved, suspended, or emulsified in a mixture of a fluid carrier and a propellant. The aerosol can be in the form of a solution, suspension, emulsion, powder, or semi-solid preparation. In the case of a powder, no propellant gas is required when the device is a breath activated dry powder inhaler. Aerosols employed are intended for administration as fine, solid particles or as liquid mists via the respiratory tract of a patient.

The propellant of an aerosol package containing the one or more compounds described herein can be capable of developing pressure within the container to expel the compound when a valve on the aerosol package is opened. Various types of propellants can be utilized, such as fluorinated hydrocarbons (e.g., trichloromonofluromethane, dichlorodifluoromethane, and dichlorotetrafluoroethane) and compressed gases (e.g., nitrogen, carbon dioxide, nitrous oxide, or Freon). The vapor pressure of the aerosol package can be determined by the propellant or propellants that are employed. By varying the proportion of each component propellant, any desired vapor pressure can be obtained within the limits of the vapor pressure of the individual propellants.

As described above, the one or more compounds described herein can be provided with a nebulizer, which is an instrument that generates very fine liquid particles of substantially uniform size in a gas. The liquid containing the one or more compounds described herein can be dispersed as droplets about 5 mm or less in diameter in the form of a mist. The small droplets can be carried by a current of air or oxygen through an outlet tube of the nebulizer. The resulting mist can penetrate into the respiratory tract of the patient.

Additional inhalants useful for delivery of the compounds described herein include intra-oral sprays, mists, metered dose inhalers, and dry powder generators (See Gonda, *J. Pharm. Sci.* 89:940-945, 2000, which is incorporated herein by reference in its entirety, at least, for inhalation delivery methods taught therein). For example, a powder composition containing the one or more compounds as described herein, with or without a lubricant, carrier, or propellant, can be administered to a patient. The delivery of the one or more compounds in powder form can be carried out with a conventional device for administering a powder pharmaceutical composition by inhalation.

Depending on the intended mode of administration, the pharmaceutical composition can be in the form of solid, semi-solid, or liquid dosage forms, such as, for example, tablets, suppositories, pills, capsules, powders, liquids, aerosols, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or pharmaceutically acceptable salts or prodrugs thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or pharmaceutically acceptable salts or prodrugs thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, aerosols, and inhalants (e.g., intra-oral sprays, mists, metered dose inhalers, nebulizers, and dry powder generators). The compounds described herein or pharmaceutically salts or prodrugs thereof are admixed under sterile conditions with a physiologically acceptable carrier and any preservatives, buffers, or propellants as can be required. Ophthalmic formulations, ointments, powders, and solutions are also contemplated as being within the scope of the compositions.

The term pharmaceutically acceptable salts as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught therein.)

Administration of compounds described herein or pharmaceutically acceptable salts or prodrugs thereof can be carried out using therapeutically effective amounts of the compounds described herein or pharmaceutically acceptable salts or prodrugs thereof for periods of time effective to treat neurological disorders. The effective amount of the compounds described herein or pharmaceutically acceptable salts or prodrugs thereof can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

IV. Methods of Use

The methods described herein include a method of treating protein folding disorders (e.g., cystic fibrosis) in a subject. These methods include the step of administering to the subject a compound of the structures described herein. Additional steps can be included in the method described herein. For example, the methods can further include the steps of selecting a subject with a protein folding disorder, such as cystic fibrosis, and administering to the subject one or more of the CFTR correctors described herein.

In the methods described herein, the subjects treated can be further treated with one or more additional agents. The one or more additional agents and the compounds described herein or pharmaceutically acceptable salts or prodrugs thereof can be administered together in a single composition (e.g., as an admixture) or in separate compositions in any order, including simultaneous administration, as well as temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

As described above, the compounds described herein are useful in the treatment of protein folding disorders. Examples of protein folding disorders include cystic fibrosis; neurodegenerative diseases such as Alzheimer's disease, Parkinson's disease, Creutzfeld-Jakob disease, Kuru, GSS disease, Huntington's disease, Polyglutamine diseases, Prion disease, Bovine Spongiform Encephalopathy (BSE), Amyotrophic Lateral Sclerosis, Alexander's disease, Primary Systemic Amyloidosis, Secondary Systemic Amyloidosis, Senile Systemic Amyloidosis, and Amyloidosis in senescence; ocular diseases such as Cataract, Retinitis Pigmentosa, and Macular Degeneration; and other diseases such as Islet amyloid, Medullar Carcinoma of the Thyroid, Hereditary Renal Amyloidosis, Hemodialysis-related amyloidosis, Desmin-related Cardiomyopathy, Charcot-Marie Tooth disease, diabetes insipidis, diabetes insipidis, alpha1 antitrypsin deficiency, Fabry's disease, Gaucher's disease, Pompe's disease, and Charcot-Marie Tooth disease. The compounds described herein are also useful in the treatment of chronic obstructive pulmonary diseases (COPD), including chronic bronchitis and/or emphysema (e.g., emphysema caused by smoking or by exposure to smoke). CFTR mRNA and protein are down-regulated in the COPD umbrella of diseases.

The compounds described herein are also useful in rescuing halide efflux in a cell, correcting the protein processing defect in a cell, and correcting functional delF508-CFTR chloride channels in a call. The methods of rescuing halide efflux in a cell include contacting a cell with a compound as described herein. In these methods, the cell endogenously expresses a CFTR mutation. Optionally, the CFTR mutation is delF508-CFTR. Optionally, the halide efflux is chloride efflux.

The methods of correcting a processing defect of a delF508-CFTR protein in a cell include contacting a cell with a compound as described herein. In these methods, the cell expresses a delF508-CFTR mutation. Optionally, the cell is a CF human airway epithelial cell or a CF human lung.

The methods of correcting functional delF508-CFTR chloride channels in a cell include contacting a cell with a compound as described herein. Optionally, the chloride channels are in the apical membrane of a polarized epithelial cell. Optionally, the method is performed in vitro or in vivo.

V. Methods of Profiling

Additionally, a method of profiling a compound for treating a protein misfolding disorder as described herein (i.e., a CFTR corrector) is provided. The methods employ assays that can gauge the relative potency and efficacy of the compounds described herein, as compared to a control, for treating a protein folding disorder such as cystic fibrosis. The methods optionally include a CF bronchial epithelial cell that endogenously expresses a CFTR mutation (e.g., the delF508-CFTR mutation). The cell can be, for example, a primary or immortal CF lung and/or airway epithelial cell (e.g., CFBE41o-cells). CFBE41o-cells are human airway epithelial cells on a delF508-CFTR homozygous background. Optionally, the cells do not overexpress the CFTR mutation.

The cell models used in other methods of identifying CFTR correctors have employed low temperature, chemical chaperones such as glycerol, 4-phenylbutyrate, DMSO, and overexpression of CFTR in a transduced Fisher rat thyroid cell line as the model, whereas the present methods do not require, and optionally exclude, over-expression of CFTR, low temperature, and chemical chaperones, variables that can distort the results.

The method of profiling can include detecting the rescue of halide efflux from a cell. The step of detecting a rescue of halide efflux from the cell can be monitored using the halide quenched dye 6-methoxy-N-(3-sulfopropyl)-quinolinium (SPQ, Molecular Probes Inc., Eugene, Oreg.). In this method, cells are treated with a compound as described herein for a period of time (e.g., 48 hours). The rescue or correction of halide efflux is then detected using the SPQ assay with the halide dye. The degree of halide efflux rescue or correction indicates that the compound has corrected delF508-CFTR-driven membrane chloride ion transport and is, therefore, useful in treating cystic fibrosis. Optionally, the halide efflux is chloride efflux. The method of screening can further comprise performing the method with multiple concentrations of the compound.

The method of profiling can also include determining the degree of CFTR glycosylation or CFTR protein processing. Optionally, this method can be performed using Western blot analysis. In this method, cells can be treated with the compound as described herein for a period of time (e.g., 24 hours) and, optionally, at multiple concentrations (e.g., 4 doses).

The method of profiling can further include determining the degree of functional delF508-CFTR chloride ion channels in the apical cell membrane of cells (e.g., polarized CF human airway epithelial cells). This method can use electrophysiological methods, such as Ussing chamber-based measurement of short-circuit current, voltammeter-based measurement of open-circuit transepithelial voltage and transepithelial resistance, and patch-clamp electrophysiology.

In general, compounds useful for treating protein misfolding disorders can be identified from large libraries of natural products or synthetic (or semi-synthetic) extracts or chemical libraries according to methods known in the art. The precise source of test extracts or compounds is not critical to the screening procedure(s). Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries and libraries of natural compounds in the form of bacterial, fungal, plant, and animal extracts are commercially available. In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

As used herein the terms treatment, treating, or treat refer to a method of reducing or delaying the onset of one or more signs or symptoms or an improvement in the clinical state of the subject being treated for a disease or disorder (e.g., a protein misfolding disorder such as cystic fibrosis). Thus, in the disclosed method, treatment can refer to a 10%, 20%, 30%, 40%, 50%, 60%, 70%, 80%, 90%, or 100% reduction in the severity of one or more symptoms of a disease or condition. For example, reduced numbers of infections or hospitalizations, reduction in respiratory or gastrointestinal symptoms, improved nutritional status, or improved pulmonary function in the subject as compared to a control indicate effective treatment. As used herein, control refers to the untreated condition (e.g., the subject not treated with the compounds and compositions described herein). Thus, the reduction can be a 10%, 20%, 30%, 40%, 50%, 60%, 70%, 80%, 90%, or 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90%, or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats;

mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compounds described herein, and are not intended to limit the scope of the claims.

EXAMPLES

Example 1: Synthesis

A synthetic scheme for DBM-308 is shown in Scheme 1.

Scheme 1:

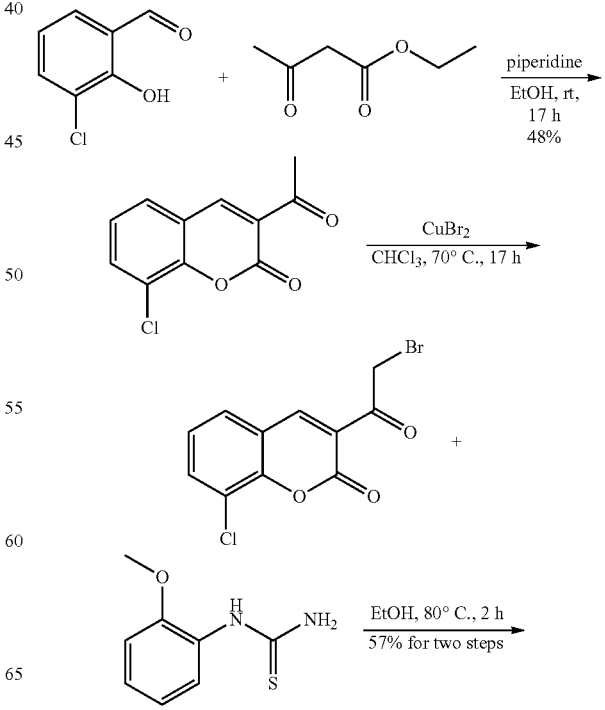

-continued

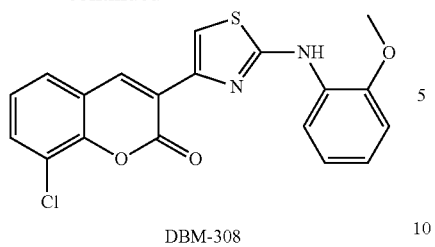

DBM-308

A synthetic scheme for DBM-E-1 is shown in Scheme 2.

Scheme 2:

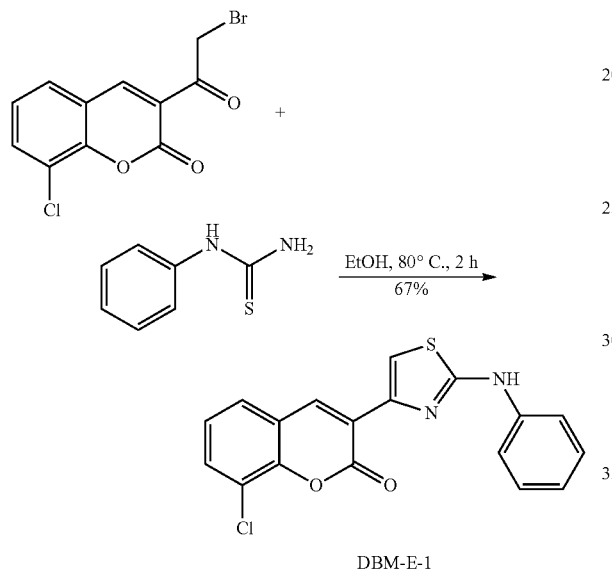

DBM-E-1

A synthetic scheme for DBM-E-2 is shown in Scheme 3.

Scheme 3:

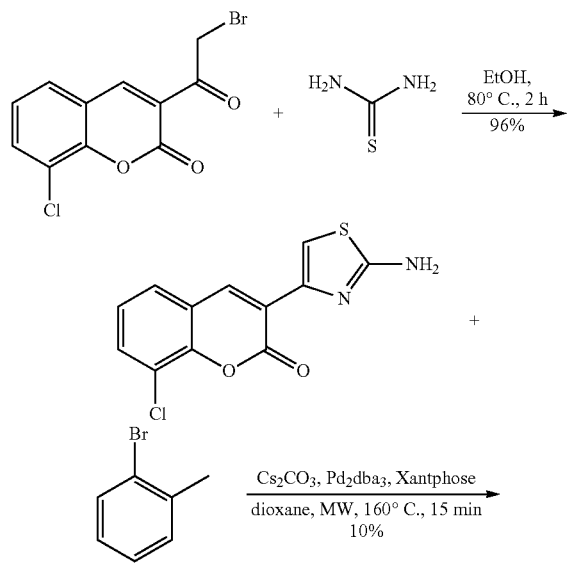

-continued

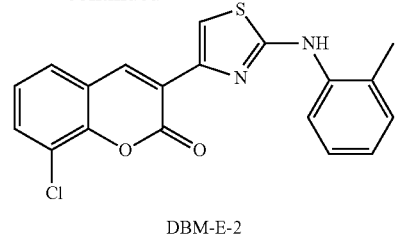

DBM-E-2

DBM-E-3 was prepared according to the procedure listed below and the synthetic scheme shown in Scheme 4.

Scheme 4:

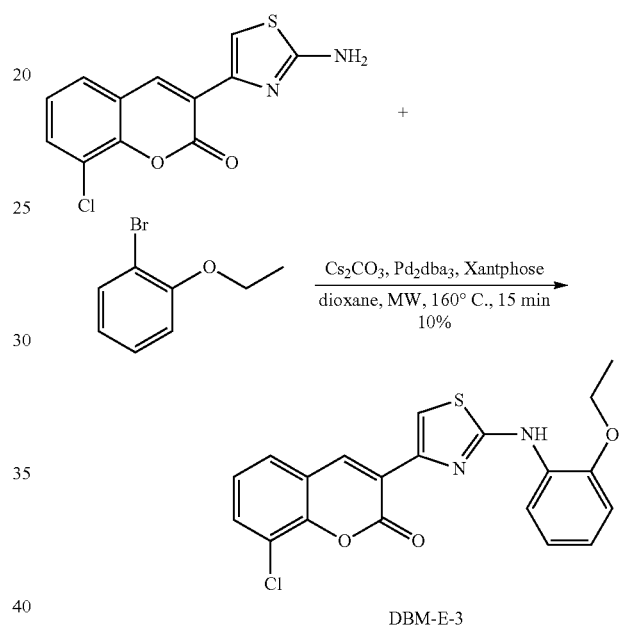

DBM-E-3

3-(2-bromoacetyl)-8-chloro-2H-chromen-2-one (150 mg, 0.54 mmol) and 1-bromo-2-ethoxybenzene (108 mg, 0.54 mmol) were reacted in a microwave in the presence of $Cs_2CO_3$ (528 mg, 1.62 mmol), $Pd_2(dba)_3$ (40 mg, 0.054 mmol.), xantphose (60 mg, 0.108 mmol), and dioxane (2 mL) at 160° C. for 15 minutes. The resulting product was then purified by pre-HPLC to yield 8-chloro-3-(2-(2-ethoxyphenylamino)thiazol-4-yl)-2H-chromen-2-one (20 mg, 10%) as a yellow solid. ESI-MS (EI$^+$, m/z): 399.1 [M+1]$^+$; $^1$HNMR (500 MHz, DMSO-d$_6$): δ 1.40 (t, J=7 Hz, 3H), 4.14 (q, J=7 Hz, 2H), 6.99-7.05 (m, 3H), 7.39 (t, J=8 Hz, 1H), 7.76-7.79 (m, 2H), 7.93 (t, J=7 Hz, 1H), 8.48-8.49 (m, 1H), 8.65 (s, 1H), 9.54 (s, 1H).

DBM-E-4 was prepared according to the procedure listed below and the synthetic scheme shown in Scheme 5.

Scheme 5:

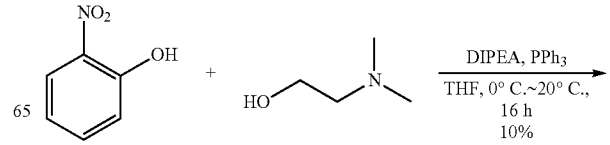

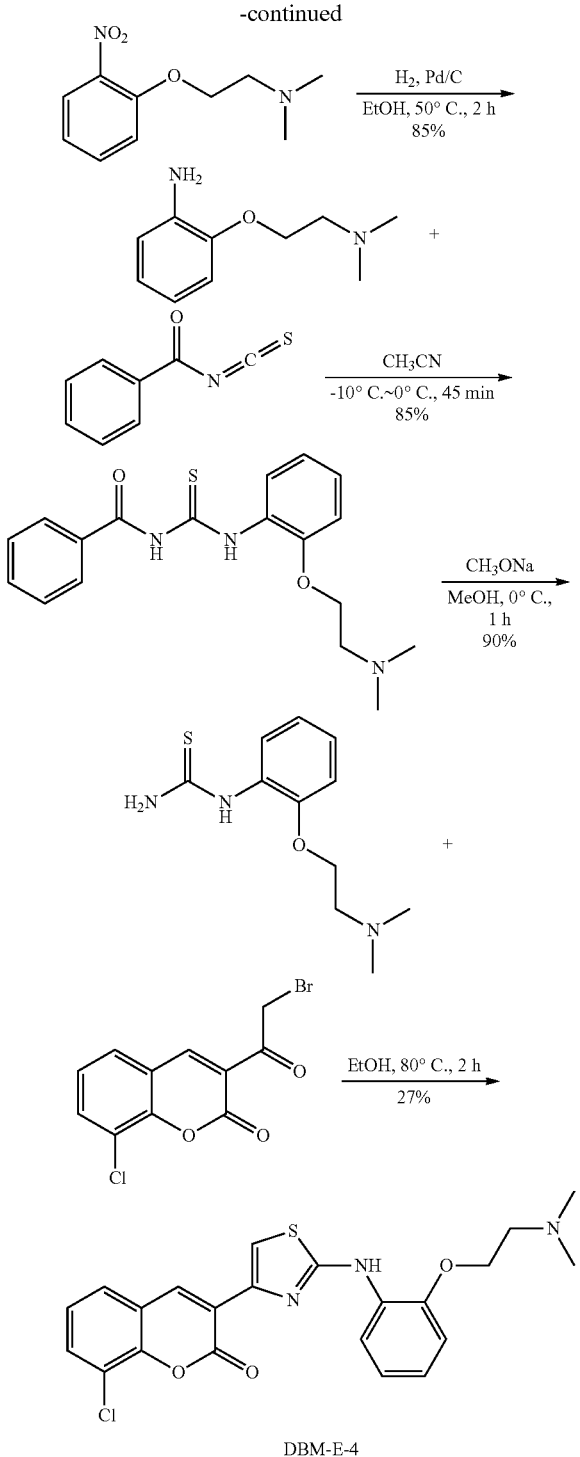

DBM-E-4

Step 1:
N,N-dimethyl-2-(2-nitrophenoxy)ethanamine

To a solution of 2-nitrophenol (13.9 g, 10 mmol), 2-(dimethylamino)ethanol (10.7 g, 12 mmol), and PPh$_3$ (29 g, 11 mmol) in dry THF (200 mL) was added DIAD (22 g, 11 mmol) dropwise at 0° C. Then, the mixture was stirred at rt for 17 hrs. The solvent was removed. The residue was dissolved in 1 N HCl aq. and washed with EtOAc. The water layer was neutralized with saturated NaHCO$_3$ and extracted with EtOAc (2×). The organic layers were collected, washed with brine, dried (Na$_2$SO$_4$), and concentrated to afford N,N-dimethyl-2-(2-nitrophenoxy)ethanamine (2.1 g, 10%) as a yellow oil. ESI-MS (EI$^+$, m/z): 211.0 [M+1]$^+$.

Step 2: 2-(2-(dimethylamino)ethoxy)aniline

To a solution of N,N-dimethyl-2-(2-nitrophenoxy)ethanamine (1.0 g, 4.76 mmol) in EtOH (10 mL) was added Pd/C (800 mg, 10%). The mixture was stirred at 50° C. for 2 hrs under H$_2$. The reaction mixture was cooled down to rt and then filtered. The filtrate was concentrated to afford 2-(2-(dimethylamino)ethoxy)aniline (730 mg, 85%) as a yellow oil. ESI-MS (EI$^+$, m/z): 181.0 [M+1]$^+$.

Step 3: N-(2-(2-(dimethylamino)ethoxy)phenylcarbamothioyl)benzamide 2-(2-(dimethylamino)ethoxy)aniline (550 mg, 3 mmol) and benzoyl isothiocyanate (727 mg, 3.6 mmol) were reacted. The resulting mixture was then purified by filtration to provide N-(2-(2-(dimethylamino)ethoxy)phenylcarbamothioyl)benzamide (360 mg, 35%) as a white solid. ESI-MS (EI$^+$, m/z): 344.0 [M+1]$^+$.

Step 4:
1-(2-(2-(dimethylamino)ethoxy)phenyl)thiourea

N-(2-(2-(dimethylamino)ethoxy)phenylcarbamothioyl)benzamide (343 mg, 1.0 mmol) was reacted with a solution of NaOMe in MeOH (1 mL, 30%), and the resulting mixture was purified by filtration to provide 1-(2-(2-(dimethylamino)ethoxy)-phenyl)thiourea (160 mg, 67%) as a white solid. ESI-MS (EI$^+$, m/z): 240.0 [M+1]$^+$.

Step 5: 8-chloro-3-(2-(2-(2-(dimethylamino)ethoxy)phenylamino)thiazol-4-yl)-2H-chromen-2-one 3-(2-bromoacetyl)-8-chloro-2H-chromen-2-one (~279 mg, 50%, 0.53 mmol) and 1-(2-(2-(dimethylamino)ethoxy)phenyl)thiourea (106 mg, 0.44 mmol) were reacted in ethanol at 80° C. The product was then purified by filtration to provide 8-chloro-3-(2-(2-(2-(dimethylamino)ethoxy)phenylamino)thiazol-4-yl)-2H-chromen-2-one (60 mg, 31%) as a yellow solid. ESI-MS (EI$^+$, m/z): 442.0 [M+1]$^+$; $^1$H NMR (500 MHz, CF$_3$COOD): δ 3.64 (s, 6H), 4.27 (s, 2H), 5.02 (s, 2H), 7.65 (d, J=8.0 Hz, 1H), 7.75 (t, J=8.0 Hz, 1H), 7.94-7.99 (m, 2H), 8.12 (s, 1H), 8.14 (d, J=8.0 Hz, 1H), 8.20 (d, J=7.5 Hz, 1H), 8.33 (d, J=7.5 Hz, 1H), 9.03 (s, 1H)

DBM-E-5 was prepared according to the procedure listed below and the synthetic scheme shown in Scheme 6.

Scheme 6:

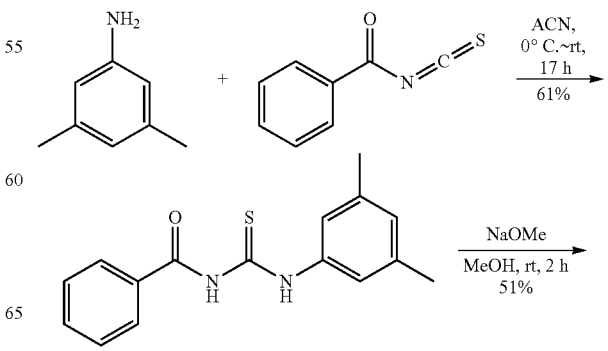

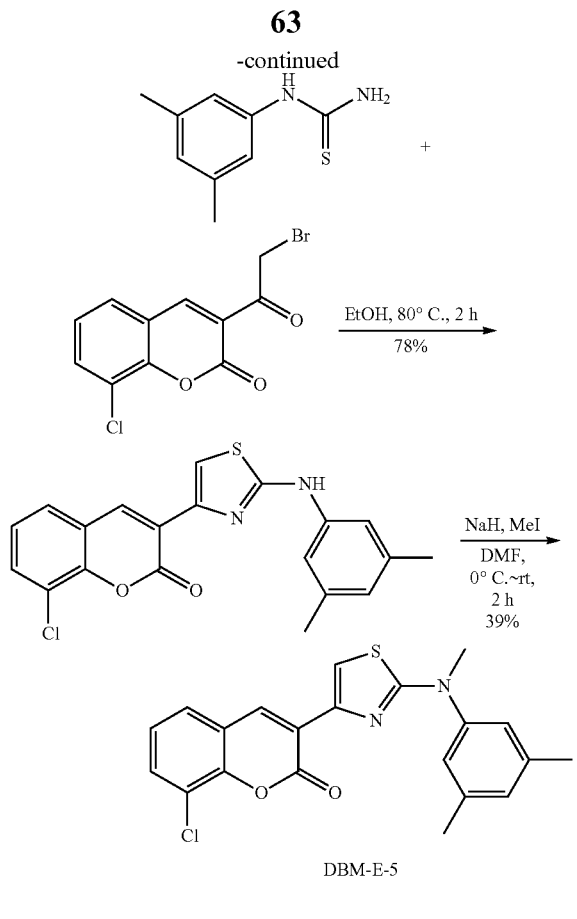

DBM-E-5

Step 1: N-(3,5-dimethylphenylcarbamothioyl)benzamide 3,5-dimethylaniline (2.42 g, 20 mmol) and benzoyl isothiocyanate (4.24 g, 26 mmol) in acetonitrile were reacted at a temperature of from 0° C. to room temperature over 17 hours. The resulting mixture was then purified by filtration to provide N-(3,5-dimethylphenylcarbamothioyl)benzamide (3.5 g, 61%) as a white solid. ESI-MS (EI$^+$, m/z): 285.1 [M+1]$^+$.

Step 2: 1-(3,5-dimethylphenyl)thiourea

N-(3,5-dimethylphenylcarbamothioyl)benzamide (3.5 g, 12.3 mmol) and a solution of NaOMe in MeOH (4 mL, 30%) were mixed at room temperature for two hours. The resulting mixture was then purified by filtration to provide 1-(3,5-dimethylphenyl)thiourea (1.1 g, 51%) as a white solid. ESI-MS (EI$^+$, m/z): 181.0 [M+1]$^+$.

Step 3: 8-chloro-3-(2-(3,5-dimethylphenylamino)thiazol-4-yl)-2H-chromen-2-one 3-(2-bromoacetyl)-8-chloro-2H-chromen-2-one (~1 g, 50%, 1.67 mmol) and 1-(3,5-dimethylphenyl)thiourea (600 mg, 3.33 mmol) were reacted in ethanol at 80° C. The product was then purified by filtration to provide 8-chloro-3-(2-(3,5-dimethylphenylamino)thiazol-4-yl)-2H-chromen-2-one (500 mg, 78%) as a yellow solid. ESI-MS (EI$^+$, m/z): 383.0 [M+1]$^+$;

Step 4: 8-chloro-3-(2-((3,5-dimethylphenyl)(methyl)amino)thiazol-4-yl)-2H-chromen-2-one To a solution of 8-chloro-3-(2-(3,5-dimethylphenylamino)thiazol-4-yl)-2H-chromen-2-one (150 mg, 0.39 mmol) in dry DMF (10 mL) was added NaH (31 mg, 60%, 0.78 mmol) at 0° C. The mixture was then stirred at 0° C. for 15 min. MeI (56 mg, 0.39 mmol) was added and the mixture was stirred at rt for 2 hrs. The reaction solution was quenched with saturated NH$_4$Cl solution, diluted with EtOAc (80 mL), washed with H$_2$O (2×) and brine (2×), dried (Na$_2$SO$_4$), filtered, and concentrated to give 8-chloro-3-(2-((3,5-dimethylphenyl)(methyl)amino)thiazol-4-yl)-2H-chromen-2-one (60 mg, 39%) as a yellow solid. ESI-MS (EI$^+$, m/z): 397.0 [M+1]$^+$; $^1$H NMR (500 MHz, DMSO-d$_6$): δ 2.31 (s, 6H), 3.56 (s, 3H), 6.98 (s, 1H), 7.13 (s, 2H), 7.39 (t, J=8.0 Hz, 1H), 7.63 (s, 1H), 7.77 (d, J=8.0 Hz, 1H), 7.89 (d, J=7.5 Hz, 1H), 8.69 (s, 1H).

DBM-E-6 was prepared according to the procedure listed below and the synthetic scheme shown in Scheme 7.

Scheme 7:

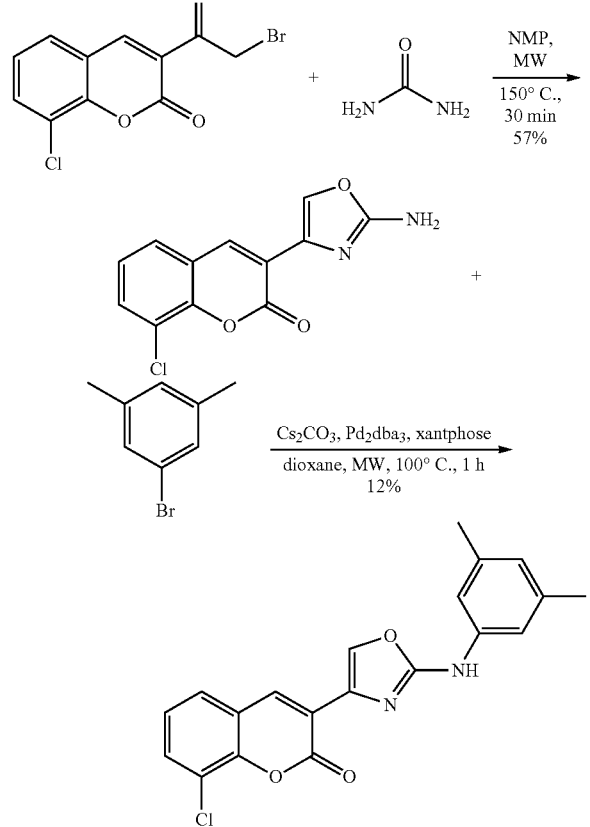

DBM-E-6

Step 1: 3-(2-aminooxazol-4-yl)-8-chloro-2H-chromen-2-one

To an oven-dried microwave vial was added 3-(2-bromoacetyl)-8-chloro-2H-chromen-2-one (600 mg, 50%, 1 mmol), urea (90 mg, 1.5 eq), and dry NMP (2 mL). The vial was capped and purged with nitrogen. The reaction mixture was heated to 150° C. for 30 min under microwave irradiation. Then, the mixture was allowed to cool and purified by pre-HPLC to afford 3-(2-aminooxazol-4-yl)-8-chloro-2H-chromen-2-one (150 mg, 57%) as a pale yellow solid. ESI-MS (EI$^+$, m/z): 263.0 [M+1]$^+$

Step 2: 8-chloro-3-(2-(3,5-dimethylphenylamino)oxazol-4-yl)-2H-chromen-2-one

To an oven-dried microwave vial was added 3-(2-aminooxazol-4-yl)-8-chloro-2H-chromen-2-one (100 mg, 0.38 mmol), 1-bromo-3,5-dimethylbenzene (702 mg, 3.8 mmol), $Cs_2CO_3$ (249 mg, 0.76 mmol), $Pd_2(dba)_3$ (35 mg, 0.038 mmol), xantphose (44 mg, 0.076 mmol), and dry dioxane (3 mL). The vial was capped and purged with nitrogen. The reaction mixture was heated to 100° C. for 1 h under microwave irradiation. The mixture was allowed to cool and diluted with EtOAc (100 mL), washed with $H_2O$ (2×) and brine (2×), dried ($Na_2SO_4$), filtered, and concentrated. The residue was purified by silica gel column chromatography (EtOAc/PE=0~10%) to get a crude product. The crude product was purified by pre-HPLC to afford 8-chloro-3-(2-(3,5-dimethylphenylamino)-oxazol-4-yl)-2H-chromen-2-one (17 mg, 12%) as a yellow solid. ESI-MS (EI$^+$, m/z): 367.1 [M+1]$^+$; $^1$HNMR (400 MHz, DMSO-d$_6$): δ 2.30 (s, 6H), 6.64 (s, 1H), 7.34 (s, 1H), 7.41 (t, J=8.0 Hz, 2H), 7.77-7.79 (m, 1H), 7.95 (d, J=7 Hz, 1H), 8.20 (s, 1H), 8.50 (s, 1H), 10.18 (s, 1H).

DBM-E-7 was prepared according to the procedure listed below and the synthetic scheme shown in Scheme 8.

Scheme 8:

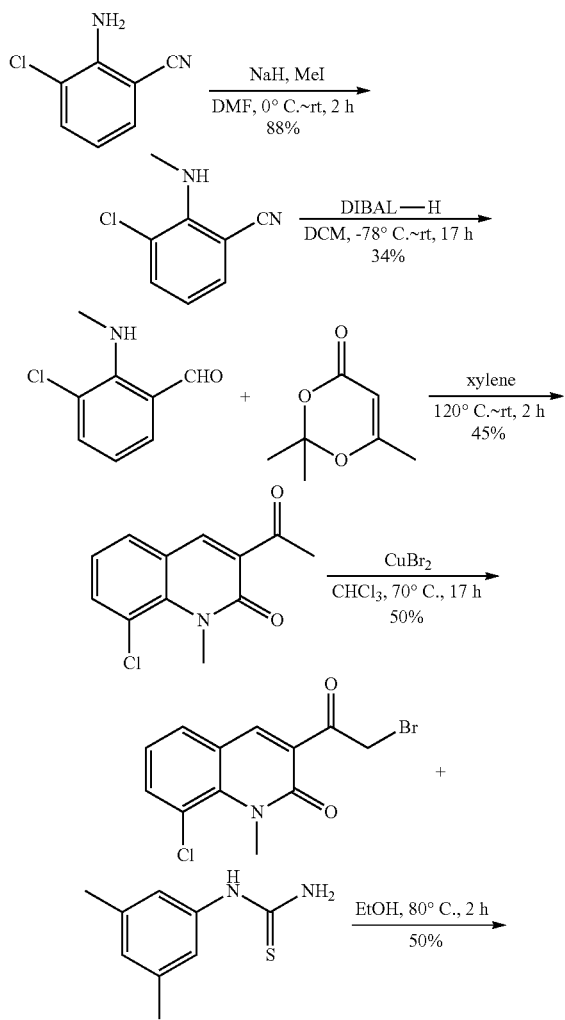

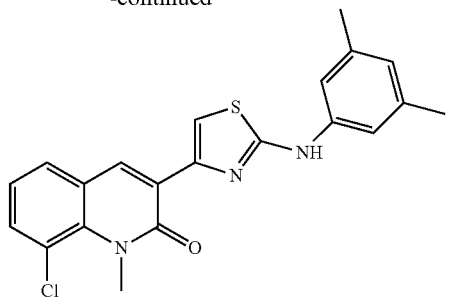

DBM-E-7

Step 1: 3-chloro-2-(methylamino)benzonitrile

To a solution of 2-amino-3-chlorobenzonitrile (5.0 g, 32.9 mmol) in dry DMF (60 mL) was added NaH (1.97 g, 60%, 49.3 mmol) at 0° C. Then, the mixture was stirred at 0° C. for 15 min. MeI (4.67 g, 32.9 mmol) was added and the mixture was stirred at rt for 2 hrs. The reaction solution was quenched with saturated $NH_4Cl$ solution, diluted with EtOAc (200 mL), washed with $H_2O$ (2×) and brine (2×), dried ($Na_2SO_4$), filtered, and concentrated. The residue was purified by silica gel column chromatography (EtOAc/PE=0~5%) to give 3-chloro-2-(methylamino)benzonitrile (4.8 g, 88%) as a white solid. ESI-MS (EI$^+$, m/z): 167.0 [M+1]$^+$.

Step 2: 3-chloro-2-(methylamino)benzaldehyde

To a solution of 3-chloro-2-(methylamino)benzonitrile (4 g, 24 mmol) in dry DCM (50 mL) was added DIBAL-H (1M, 36 mL, 36 mmol) at −78° C. Then, the mixture was stirred at rt for 17 hrs. The reaction mixture was quenched with a saturated citric acid solution, diluted with DCM (150 mL), washed with $H_2O$ (2×) and brine (2×), dried ($Na_2SO_4$), filtered, and concentrated. The residue was purified by silica gel column chromatography (EtOAc/PE=0~3%) to give 3-chloro-2-(methylamino)benzaldehyde (1.4 g, 34%) as a yellow oil. ESI-MS (EI$^+$, m/z): 170.0 [M+1]$^+$.

Step 3: 3-acetyl-8-chloro-1-methylquinolin-2(1H)-one

A solution of 3-chloro-2-(methylamino)benzaldehyde (800 mg, 4.7 mmol) in xylene (30 mL) at 120° C. was treated with 2,2,6-trimethyl-4H-1,3-dioxin-4-one (6.7 g, 47 mmol). The reaction mixture was heated at 120° C. for 2 hrs and then cooled to rt. The solvent was removed and the residue was purified by silica gel column chromatography (EtOAc/PE=0~3%) to give 3-acetyl-8-chloro-1-methylquinolin-2(1H)-one (500 mg, 45%) as a yellow solid. ESI-MS (EI m/z): 236.0 [M+1]$^+$; $^1$H NMR (500 MHz, DMSO-d$_6$): δ 2.61 (s, 3H), 3.86 (s, 3H), 7.31 (t, J=8 Hz, 1H), 7.79-7.81 (m, 1H), 7.92-7.94 (m, 1H), 8.41 (s, 1H).

Step 4: 3-(2-bromoacetyl)-8-chloro-1-methylquinolin-2(1H)-one

To a solution of 3-acetyl-8-chloro-1-methylquinolin-2 (1H)-one (432 mg, 1.84 mmol) in $CHCl_3$ (20 mL) was added $CuBr_2$ (404 mg, 1.84 mmol) at rt. The mixture was stirred at 70° C. for 17 hrs. The solvent was evaporated, the crude product was diluted with EtOAc (100 mL), washed with water (2×), brine (2×), dried (Na$_2$SO$_4$), and concentrated to provide 3-(2-bromoacetyl)-8-chloro-1-methylquinolin-2(1H)-one (~500 mg, 50%), which was used directly in the next step. ESI-MS (EI$^+$, m/z): 313.9 [M+H]$^+$.

Step 5: 8-chloro-3-(2-(3,5-dimethylphenylamino)thiazol-4-yl)-1-methylquinolin-2(1H)-one 3-(2-bromoacetyl)-8-chloro-1-methylquinolin-2(1H)-one (~200 mg, 50%, 0.32 mmol) and 1-(3,5-dimethylphenyl)thiourea (115 mg, 0.64 mmol) were reacted in ethanol at 80° C. The product was then purified by filtration to provide 8-chloro-3-(2-(3,5-dimethylphenylamino)thiazol-4-yl)-1-methylquinolin-2(1H)-one (50 mg, 50%) as a yellow solid. ESI-MS (EI$^+$, m/z): 396.0 [M+1]$^+$; $^1$HNMR (500 MHz, DMSO-d$_6$): δ 2.31 (s, 6H), 3.94 (s, 3H), 6.64 (s, 1H), 7.29-7.35 (m, 3H), 7.69-7.71 (m, 1H), 7.81 (d, J=7.0 Hz, 1H), 7.99 (s, 1H), 8.58 (s, 1H), 10.16 (s, 1H).

DBM-E-8 was prepared according to the procedure listed below and the synthetic scheme shown in Scheme 9.

Scheme 9:

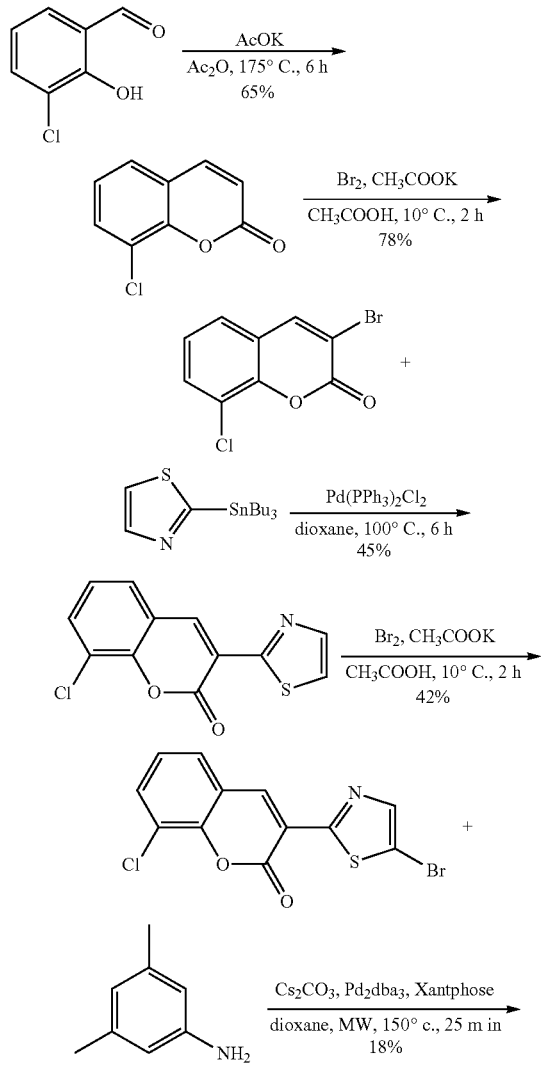

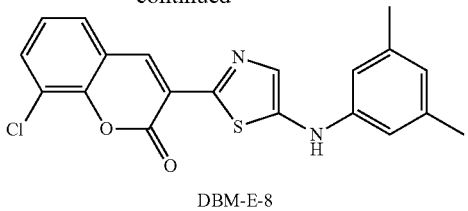

DBM-E-8

Step 1: 8-chloro-2H-chromen-2-one

A mixture of 3-chloro-2-hydroxybenzaldehyde (1 g, 6.4 mmol) and CH$_3$COOH (1.3 g, 12.8 mmol) in Ac$_2$O (45 mL) was heated to 175° C. for 6 hrs. The mixture was then cooled down to rt. The precipitate which formed was collected to give 8-chloro-2H-chromen-2-one (1.02 g, 88%) as a brown solid. ESI-MS (EI$^+$, m/z): 181.0 [M+1]$^+$.

Step 2: 3-bromo-8-chloro-2H-chromen-2-one

To a mixture of 8-chloro-2H-chromen-2-one (1 g, 5.56 mmol) and CH$_3$COOK (1.09 g, 11.1 mmol) in CH$_3$COOH (30 mL) was added Br$_2$ (4.4 g, 27.8 mmol). The mixture was stirred at 50° C. for 4 hrs. The reaction mixture was cooled to rt and poured into water (100 mL) and filtered to get a brown solid. The crude product was purified by silica gel column chromatography (EtOAc/PE=0~5%) to give 3-bromo-8-chloro-2H-chromen-2-one (640 mg, 45%) as a yellow solid. ESI-MS (EI$^+$, m/z): 260.9 [M+1]$^+$.

Step 3: 8-chloro-3-(thiazol-2-yl)-2H-chromen-2-one

A mixture of 3-bromo-8-chloro-2H-chromen-2-one (620 mg, 2.4 mmol), 2-(tributylstannyl)thiazole (1.8 g, 4.8 mmol), and Pd(PPh$_3$)$_4$ (276 mg, 0.24 mmol) in dry dioxane (20 mL) was heated to 100° C. for 6 hrs. The reaction mixture was then cooled to rt and concentrated. The residue was purified by silica gel column chromatography (EtOAc/PE=0~30%) to give 8-chloro-3-(thiazol-2-yl)-2H-chromen-2-one (500 mg, 79%) as a yellow solid. ESI-MS (EI$^+$, m/z): 264.0 [M+1]$^+$.

Step 4: 3-(5-bromothiazol-2-yl)-8-chloro-2H-chromen-2-one

To a mixture of 8-chloro-3-(thiazol-2-yl)-2H-chromen-2-one (400 mg, 1.52 mmol) and CH$_3$COOK (447 mg, 4.56 mmol) in CH$_3$COOH (15 ml) was added Br$_2$ (479 mg, 3.04 mmol). Then, the mixture was stirred at rt for 2 hrs. The reaction mixture was poured into water (100 mL) and filtered to get a brown solid. The crude product was purified by silica gel column chromatography (EtOAc/PE=0~20%) to give 3-(5-bromothiazol-2-yl)-8-chloro-2H-chromen-2-one (250 mg, 48%) as a yellow solid. ESI-MS m/z): 342.0 [M+1]$^+$.

Step 5: 8-chloro-3-(5-(3,5-dimethylphenylamino)thiazol-2-yl)-2H-chromen-2-one 3-(5-bromothiazol-2-yl)-8-chloro-2H-chromen-2-one (100 mg, 0.3 mmol) and 3,5-dimethylaniline (182 mg, 1.5 mmol) were reacted in a microwave in the presence of Cs$_2$CO$_3$ (293 mg, 0.9 mmol), Pd$_2$(dba)$_3$ (21 mg, 0.03 mmol.), xantphose (52 mg, 0.09 mmol), and dioxane (2 mL) at 150° C. for 25 minutes. The mixture was then purified by pre-HPLC to provide 8-chloro-3-(5-(3,5-dimethylphenylamino)thiazol-2-yl)-2H-chromen-2-one (25 mg, 22%) as a yellow solid. ESI-MS (EI+, m/z): 383.1 [M+1]+; 1H NMR (500 MHz, DMSO-d6): δ 2.25 (s, 6H), 6.56 (s, 1H), 6.74 (s, 2H), 7.43 (t, J=8 Hz, 1H), 7.63 (s, 1H), 7.79-7.81 (m, 1H), 7.93-7.94 (m, 1H), 8.81 (s, 1H), 9.15 (s, 1H).

DBM-E-10 was prepared according to the procedure listed below and the synthetic scheme shown in Scheme 10.

Scheme 10:

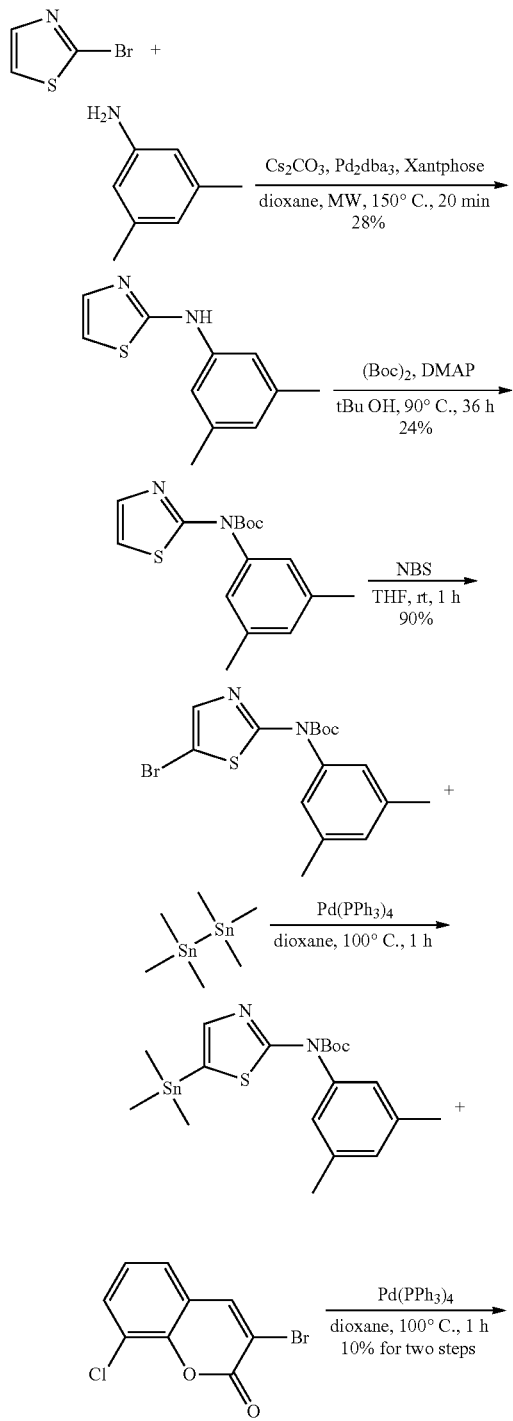

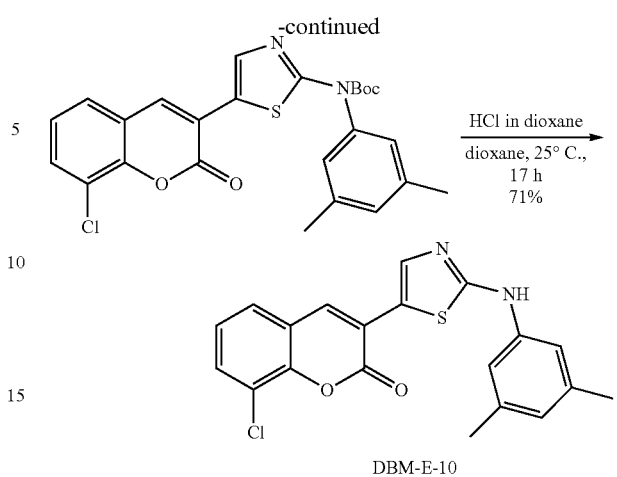

Step 1: N-(3,5-dimethylphenyl)thiazol-2-amine

2-Bromothiazole (3.26 g, 20 mmol), 3,5-dimethylaniline (3.6 g, 30 mmol) and p-toluenesulfonic acid (1.7 g, 10 mmol) were dissolved in i-propanol (50 mL). The mixture was stirred at 80° C. for 17 hrs. The reaction mixture was diluted with EtOAc (200 mL), washed with H2O (2×) and brine (2×), dried (Na2SO4), filtered, and concentrated. The residue was purified by silica gel column chromatography (EtOAc/PE=0~20%) to give N-(3,5-dimethylphenyl)thiazol-2-amine (1.1 g, 27%) as a white solid. ESI-MS (EI+, m/z): 205.0 [M+1]+.

Step 2: tert-butyl 3,5-dimethylphenyl(thiazol-2-yl)carbamate

A mixture of N-(3,5-dimethylphenyl)thiazol-2-amine (1.02 g, 5 mmol), (Boc)2O (5.45 g, 25 mmol) and DMAP (1.52 g, 12.5 mmol) in t-BuOH (20 mL) was heated to 80° C. for 36 hrs. The solvent was removed and the residue was purified by silica gel column chromatography (EtOAc/PE=0~5%) to give tert-butyl 3,5-dimethylphenyl(thiazol-2-yl)carbamate (360 mg, 24%) as a white solid. ESI-MS m/z): 305.0 [M+1]+.

Step 3: tert-butyl 5-bromothiazol-2-yl(3,5-dimethylphenylkarbamate

To a mixture of tert-butyl 3,5-dimethylphenyl(thiazol-2-yl)carbamate (390 mg, 1.28 mmol) in THF (15 mL) was added NBS (252 mg, 1.41 mmol) at rt. Then the mixture was stirred at rt for 1 h. The solvent was removed and the residue was purified by silica gel column chromatography (EtOAc/PE=0~5%) to give tert-butyl 5-bromothiazol-2-yl(3,5-dimethylphenyl)carbamate (445 mg, 90%) as a pale yellow solid. ESI-MS (EI+, m/z): 385.0 [M+1]+.

Step 4: tert-butyl 3,5-dimethylphenyl(5-(trimethylstannyl)thiazol-2-yl)carbamate A mixture of tert-butyl 5-bromothiazol-2-yl(3,5-dimethylphenyl)carbamate (445 mg, 1.17 mmol), 1,1,1,2,2,2-hexamethyldistannane (579 mg, 1.76 mmol), and Pd(PPh3)2Cl2 (83 mg, 0.12 mmol) in dioxane (15 mL) was stirred at 100° C. for 1 h. Then the mixture was cooled to rt and quenched with a saturated KF solution. The mixture was stirred at rt for 1 h, diluted with EtOAc (100 mL), washed with H2O (2×) and brine (2×), dried (Na₂SO₄), filtered, and concentrated. The crude product tert-butyl 3,5-dimethylphenyl(5-(trimethylstannyl)thiazol-2-yl)carbamate (~500 mg) was used directly in the next step. ESI-MS (EI⁺, m/z): 469.0 [M+1]⁺.

Step 5: tert-butyl-5-(8-chloro-2-oxo-2H-chromen-3-yl)thiazol-2-yl(3,5-dimethylphenyl) carbamate A mixture of tert-butyl 3,5-dimethylphenyl(5-(trimethylstannyl)thiazol-2-yl) carbamate (~500 mg), 3-bromo-8-chloro-2H-chromen-2-one (300 mg, 1.16 mmol), and Pd(PPh₃)₂Cl₂ (83 mg, 0.12 mmol) in dioxane (15 mL) was stirred at 100° C. for 1 h. Then, the mixture was cooled to rt, diluted with EtOAc (100 mL), washed with H₂O (2×) and brine (2×), dried (Na₂SO₄), filtered, and concentrated. The residue was purified by pre-HPLC to give tert-butyl 5-(8-chloro-2-oxo-2H-chromen-3-yl)thiazol-2-yl(3,5-dimethylphenyl)carbamate (30 mg, 10% for two steps) as a yellow solid. ESI-MS (EI⁺, m/z): 483.0 [M+1]⁺.

Step 5: 8-chloro-3-(2-(3,5-dimethylphenylamino)thiazol-5-yl)-2H-chromen-2-one

To a solution of tert-butyl-5-(8-chloro-2-oxo-2H-chromen-3-yl)thiazol-2-yl(3,5-dimethylphenyl)carbamate (25 mg, 0.05 mmol) in dioxane (2 mL) was added a solution of HCl in dioxane (4M, 60 mL). The mixture was stirred at 25° C. for 17 hrs. Then the solvent was removed. The solid was washed with Et₂O to afford 8-chloro-3-(2-(3,5-dimethylphenylamino)thiazol-5-yl)-2H-chromen-2-one (17 mg, 71%) as a yellow solid. ESI-MS (EI⁺, m/z): 383.1 [M+1]⁺; ¹H NMR (400 MHz, CF₃COOD): δ 2.91 (s, 6H), 7.58 (s, 2H), 7.71 (s, 1H), 7.96 (t, J=8.0 Hz, 1H), 8.16 (d, J=8.0 Hz, 1H), 8.30 (d, J=8.0 Hz, 1H), 8.61 (s, 1H), 8.82 (s, 1H).

A synthetic scheme for DBM-E-11 is shown in Scheme 11.

Scheme 11:

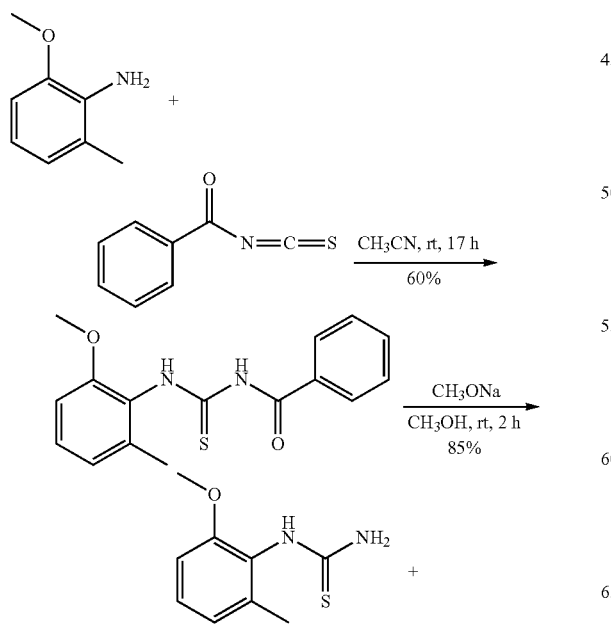

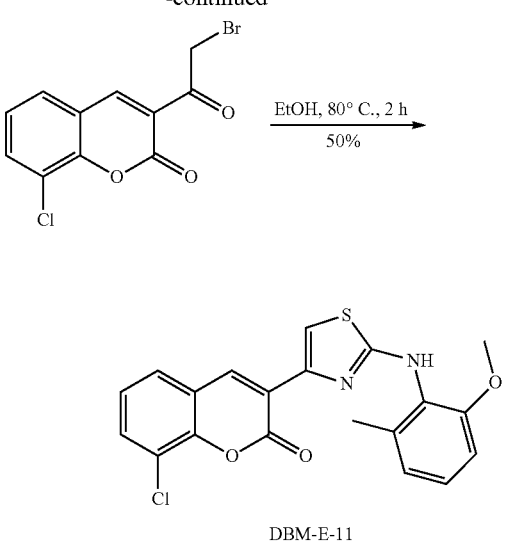

DBM-E-11

A synthetic scheme for DBM-E-12 is shown in Scheme 12.

Scheme 12:

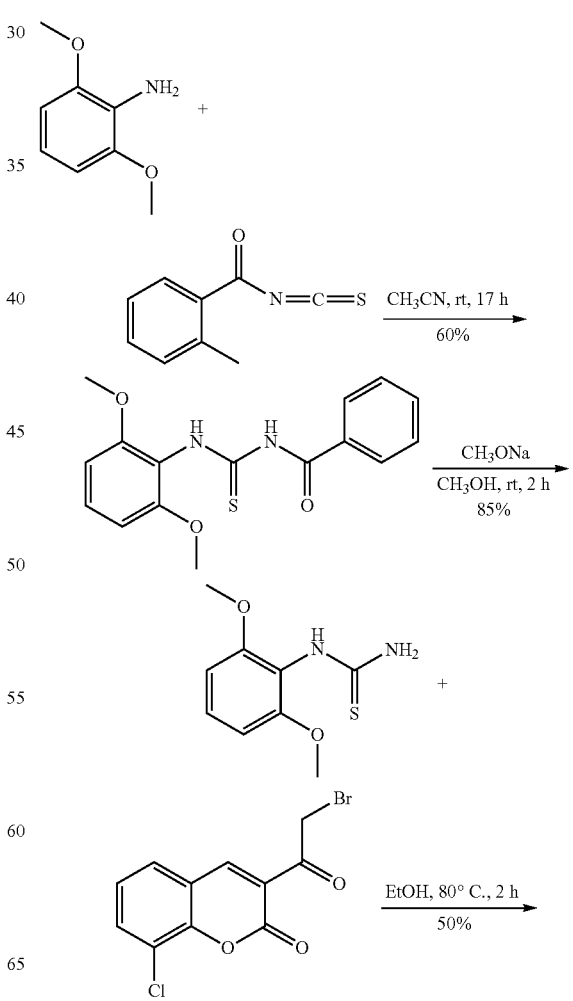

-continued

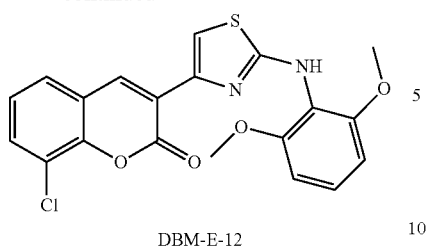

DBM-E-12

DBM-E-13 was prepared according to the procedure listed below and the synthetic scheme shown in Scheme 13.

Scheme 13:

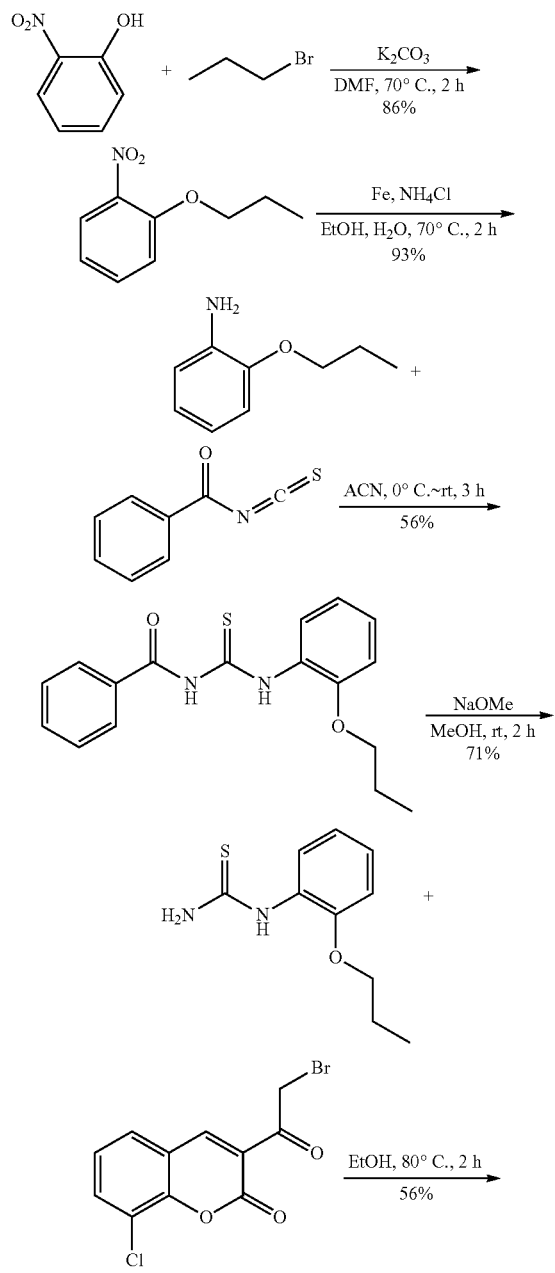

-continued

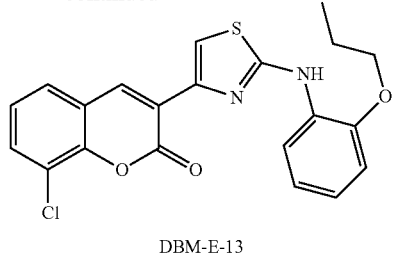

DBM-E-13

Step 1: 1-nitro-2-propoxybenzene

A mixture of 2-nitrophenol (3 g, 21.6 mmol), 1-bromopropane (3.9 g, 32.4 mmol), and $K_2CO_3$ (8.9 g, 64.8 mmol) in DMF (50 mL) was stirred at 70° C. for 2 hrs. The reaction mixture was cooled to rt, diluted with EtOAc (150 mL), washed with $H_2O$ (2×) and brine (2×), dried ($Na_2SO_4$), filtered, and concentrated. The residue was purified by silica gel column chromatography (EtOAc/PE=0~3%) to give 1-nitro-2-propoxybenzene (3.36 g, 86%) as a yellow oil. ESI-MS (EI$^+$, m/z): 182.0 [M+1]$^+$.

Step 2: 2-propoxyaniline

A mixture of 1-nitro-2-propoxybenzene (1.5 g, 8.3 mol), Fe (2.32 g, 41.5 mmol), $NH_4Cl$ (2.19 g, 41.5 mmol) in EtOH (20 mL) and $H_2O$ (2 mL) was stirred at 90° C. for 2 hrs. The reaction mixture was filtered. The filtrate was concentrated and the residue was diluted with DCM (100 mL), dried ($Na_2SO_4$), filtered, and concentrated to afford 2-propoxyaniline (1.16 g, 93%) as yellow oil. ESI-MS (EI$^+$, m/z): 152.0 [M+1]$^+$.

Step 3: N-(2-propoxyphenylcarbamothioyl)benzamide 2-propoxyaniline (1.16 g, 7.68 mmol) and benzoyl isothiocyanate (1.63 g, 10.0 mmol) were reacted in acetonitrile at a temperature of from 0° C. to room temperature over 3 hours. The mixture was then purified by filtration to provide N-(2-propoxyphenylcarbamothioyl)benzamide (1.36 g, 56%) as a white solid. ESI-MS (EI$^+$, m/z): 315.0 [M+1]$^+$.

Step 4: 1-(2-propoxyphenyl)thiourea

N-(2-propoxyphenylcarbamothioyl)benzamide (1.36 g, 4.3 mmol) was reacted with a solution of NaOMe in MeOH (4 mL, 30%). The resulting mixture was then purified by filtration to provide 1-(2-propoxyphenyl)thiourea (650 mg, 71%) as a white solid. ESI-MS (EI$^+$, m/z): 211.0 [M+1]$^+$.

Step 5: 8-chloro-3-(2-(2-propoxyphenylamino)thiazol-4-yl)-2H-chromen-2-one 3-(2-bromoacetyl)-8-chloro-2H-chromen-2-one (~300 mg, 50%, 0.5 mmol) and 1-(2-propoxyphenyl)thiourea (158 mg, 0.75 mmol) were reacted in ethanol at 80° C. The product was then purified by filtration to provide 8-chloro-3-(2-(2-propoxyphenylamino)thiazol-4-yl)-2H-chromen-2-one (115 mg, 56%) as a yellow solid. ESI-MS (EI$^+$, m/z): 413.0 [M+1]$^+$; $^1$H NMR (400 MHz, DMSO-$d_6$): δ 0.99 (t, J=7.2 Hz, 3H), 1.78-1.84 (m, 2H), 4.03 (t, J=6.8 Hz, 2H), 7.01-7.05 (m, 3H), 7.39 (t, J=8 Hz, 1H), 7.76-7.79 (m, 2H), 7.93 (d, J=7.6 Hz, 1H), 8.41-8.44 (m, 1H), 8.64 (s, 1H), 9.49 (s, 1H).
A synthetic scheme for DBM-E-14 is shown in Scheme 14.
Scheme 14:
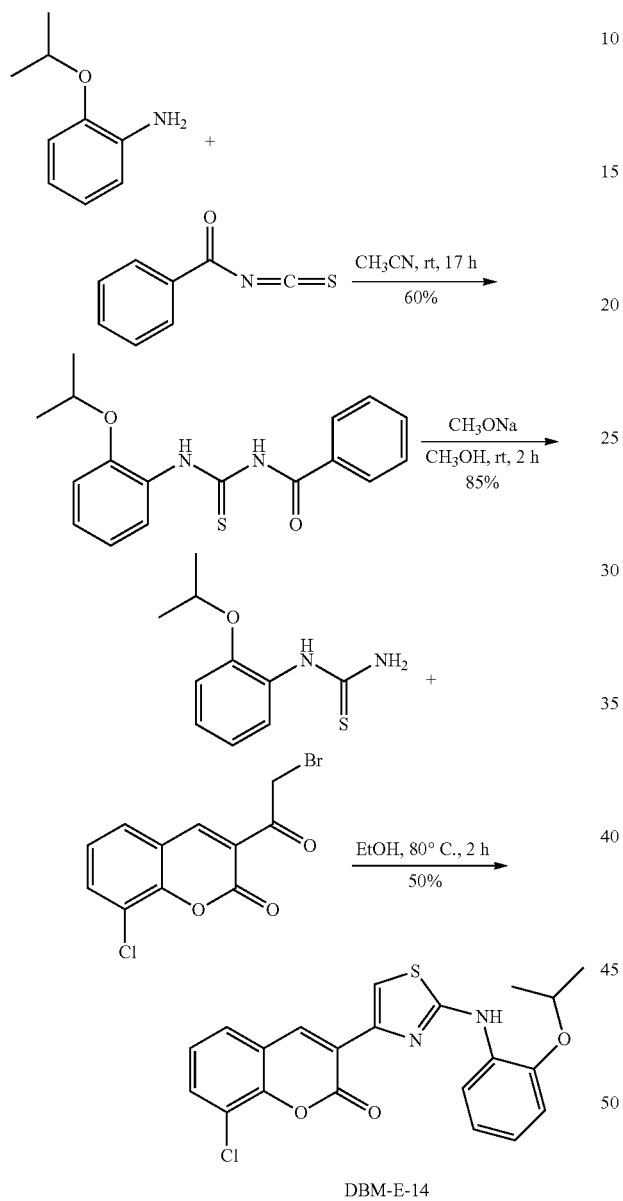
DBM-E-14
A synthetic scheme for DBM-E-15 is shown in Scheme 15.
Scheme 15:
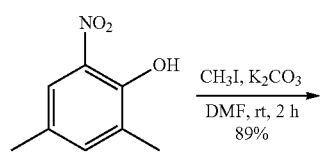
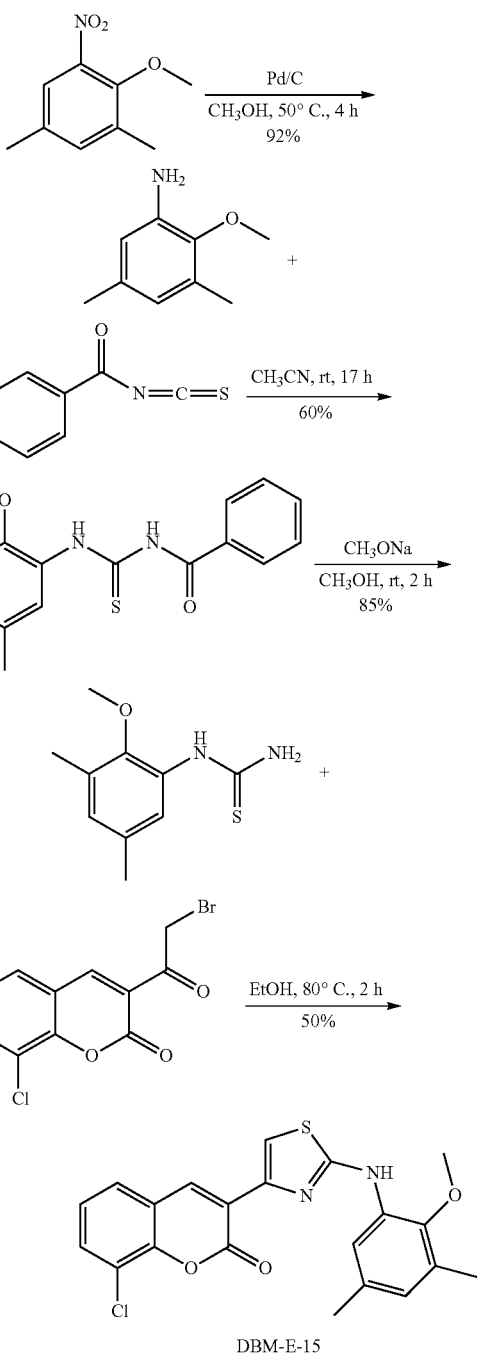
DBM-E-15
DBM-E-16 was prepared according to the procedure listed below and the synthetic scheme shown in Scheme 16.
Scheme 16:
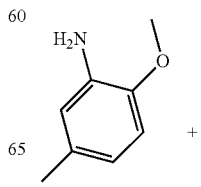

-continued

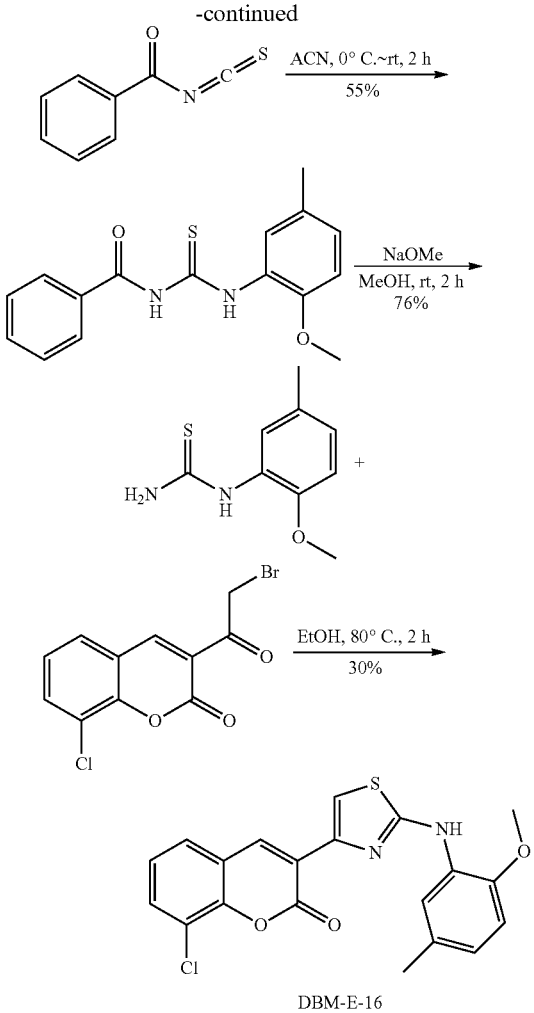

Step 1:
N-(2-methoxy-5-methylphenykarbamothioyl)benzamide 2-methoxy-5-methylaniline (500 mg, 3.65 mmol) and benzoyl isothiocyanate (773 mg, 4.74 mmol were reacted in acetonitrile at a temperature of from 0° C. to room temperature over 2 hours. The mixture was then purified by filtration to provide N-(2-methoxy-5-methylphenylcarbamothioyl) benzamide (600 mg, 55%) as a white solid. ESI-MS (EI+, m/z): 301.1 [M+1]+.

Step 2: 1-(2-methoxy-5-methylphenyl)thiourea

N-(2-methoxy-5-methylphenylcarbamothioyl)-benzamide (600 mg, 2 mmol) was reacted with a solution of NaOMe in MeOH (0.7 mL, 30%). The resulting mixture was then purified by filtration to provide 1-(2-methoxy-5-methylphenyl)thiourea (300 mg, 76%) as a white solid. ESI-MS (EI+, m/z): 197.0 [M+1]+.

Step 3: 8-chloro-3-(2-(2-methoxy-5-methylphenylamino)thiazol-4-yl)-2H-chromen-2-one 3-(2-bromoacetyl)-8-chloro-2H-chromen-2-one (~300 mg, 50%, 0.5 mmol) and 1-(2-methoxy-5-methylphenyl) thiourea (197 mg, 1 mmol) were reacted in ethanol at 80° C.

The product was then purified by filtration to provide 8-chloro-3-(2-(2-methoxy-5-methylphenylamino)thiazol-4-yl)-2H-chromen-2-one (60 mg, 30%) as a yellow solid. ESI-MS (EI+, in/z): 399.0 [M+1]+; $^1$H NMR (400 MHz, DMSO-d$_6$): δ 2.36 (s, 3H), 3.84 (s, 3H), 6.82 (d, J=8.4 Hz, 1H), 6.93 (d, J=8.4 Hz, 1H), 7.39 (t, J=8.0 Hz, 1H), 7.75-7.77 (m, 2H), 7.83 (d, J=7.6 Hz, 1H), 8.29 (s, 1H), 8.58 (s, 1H), 9.62 (s, 1H).

A synthetic scheme for DBM-E-17 is shown in Scheme 17.

Scheme 17:

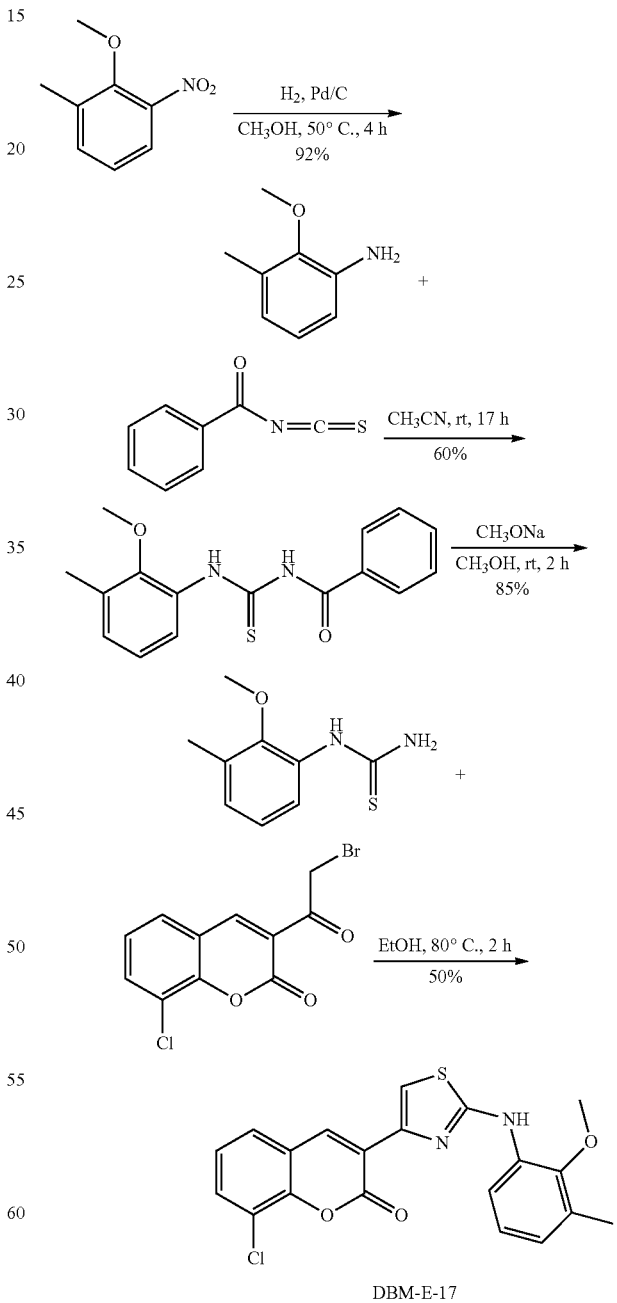

A synthetic scheme for DBM-E-18 is shown in Scheme 18.

Scheme 18:

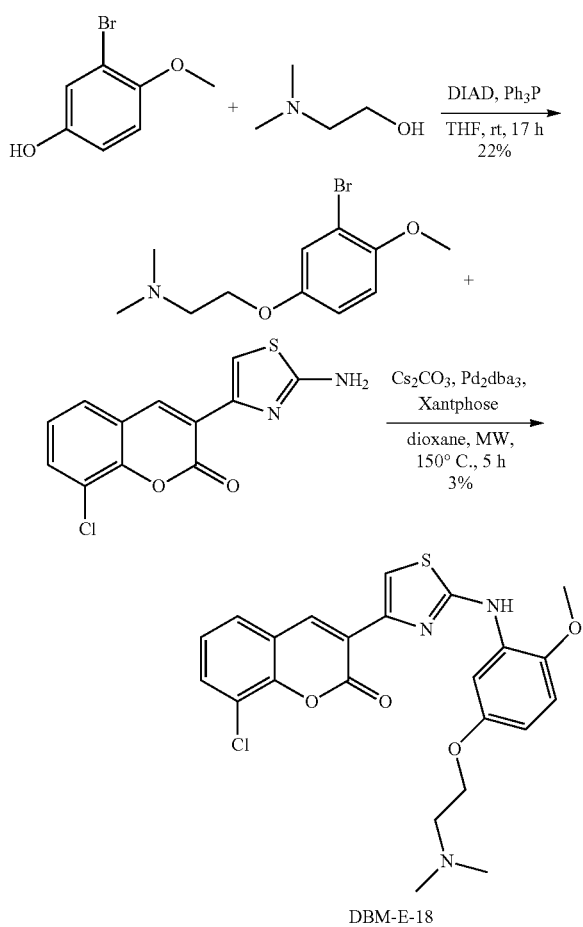

DBM-E-20 was prepared according to the procedure listed below and the synthetic scheme shown in Scheme 19.

Scheme 19:

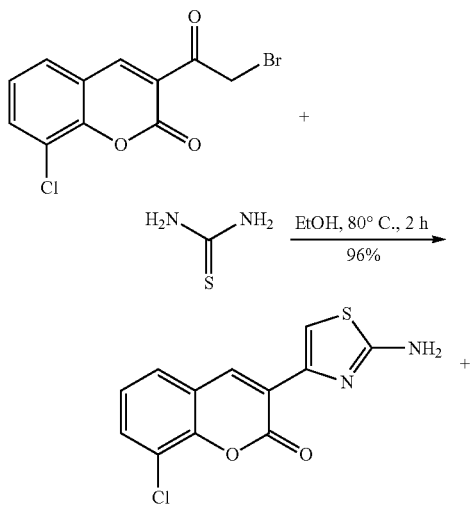

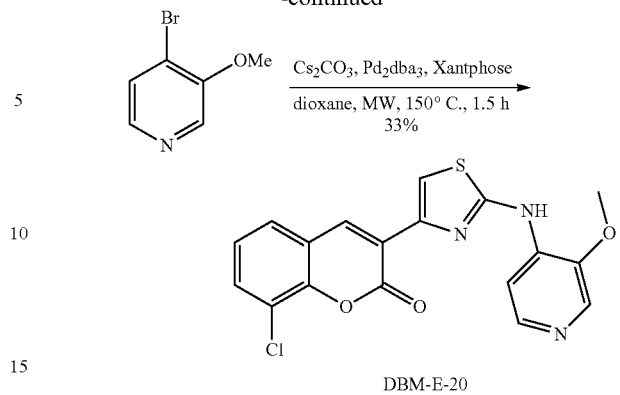

DBM-E-20

Step 1: 3-(2-aminothiazol-4-yl)-8-chloro-2H-chromen-2-one

A mixture of 3-(2-bromoacetyl)-8-chloro-2H-chromen-2-one (~1.4 g, 50%, 2.33 mmol) and thiourea (355 mg, 4.67 mmol) in EtOH (25 mL) was stirred at 80° C. for 2 hrs. The precipitate which formed was collected to give 3-(2-aminothiazol-4-yl)-8-chloro-2H-chromen-2-one (630 mg, 96%) as a yellow solid. ESI-MS (EI$^+$, m/z): 279.0 [M+1]$^+$;

Step 2: 8-chloro-3-(2-(3-methoxypyridin-4-ylamino)thiazol-4-yl)-2H-chromen-2-one 3-(2-aminothiazol-4-yl)-8-chloro-2H-chromen-2-one (100 mg, 0.36 mmol) and 4-bromo-3-methoxypyridine hydrochloride (80 mg, 0.36 mmol) were reacted in a microwave in the presence of $Cs_2CO_3$ (351 mg, 1.08 mmol), $Pd_2(dba)_3$ (25 mg, 0.036 mmol), xantphose (41 mg, 0.072 mmol), and dry dioxane (2 mL) at 150° C. for 1.5 hr. The mixture was then purified by pre-HPLC to provide 8-chloro-3-(2-(3-methoxypyridin-4-ylamino)thiazol-4-yl)-2H-chromen-2-one (45 mg, 33%) as a yellow solid. ESI-MS (EI$^+$, m/z): 386.1 [M+1]$^+$; $^1$H NMR (400 MHz, DMSO-d$_6$): δ 3.98 (s, 3H), 7.42 (t, J=8 Hz, 1H), 7.77-7.79 (m, 1H), 7.92 (s, 1H), 8.00 (d, J=7 Hz, 1H), 8.21-8.26 (m, 2H), 8.68-8.74 (m, 2H), 10.27 (s, 1H).

A synthetic scheme for DBM-E-22 is shown in Scheme 20.

Scheme 20:

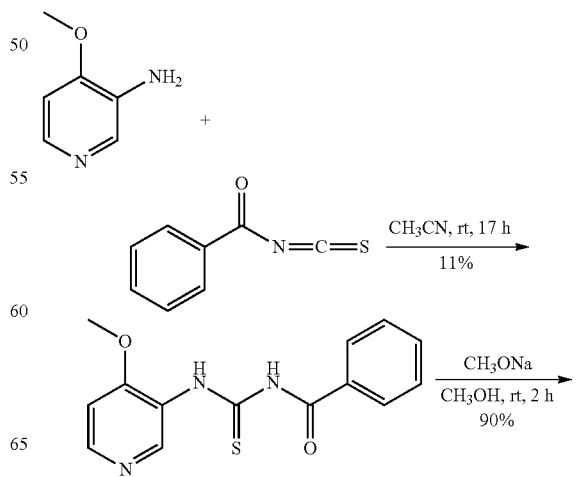

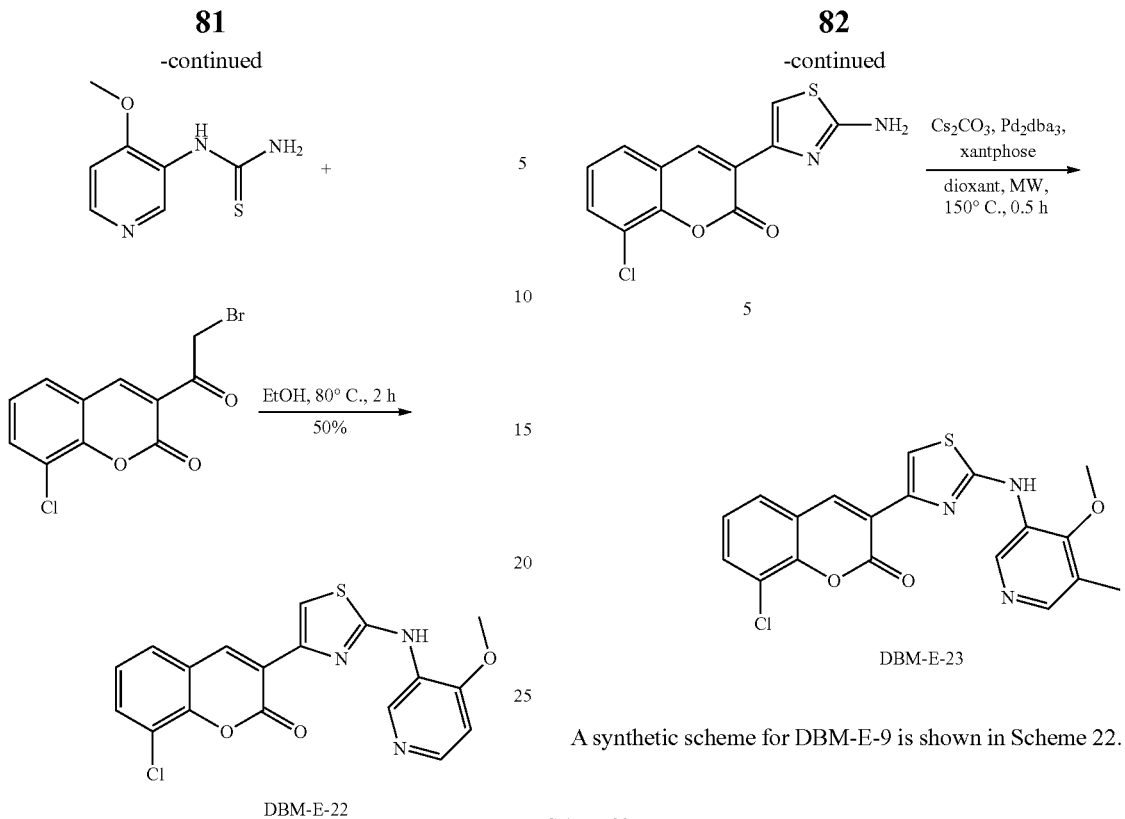
DBM-E-22
A synthetic scheme for DBM-E-23 is shown in Scheme 21.
Scheme 21:
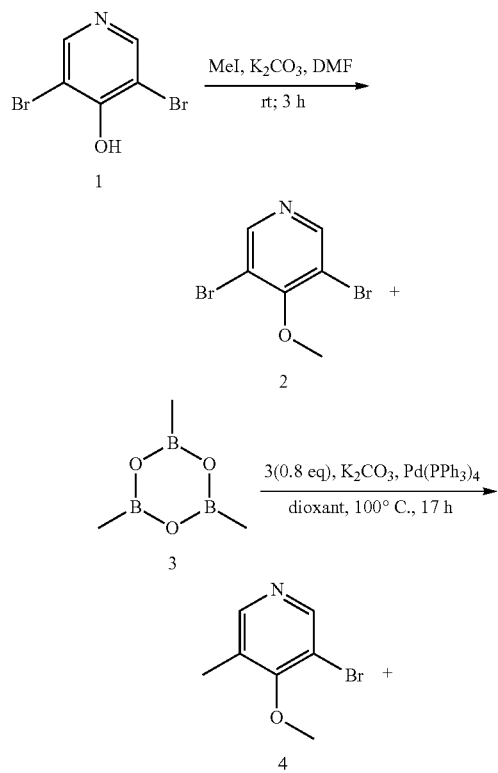
A synthetic scheme for DBM-E-9 is shown in Scheme 22.
Scheme 22:
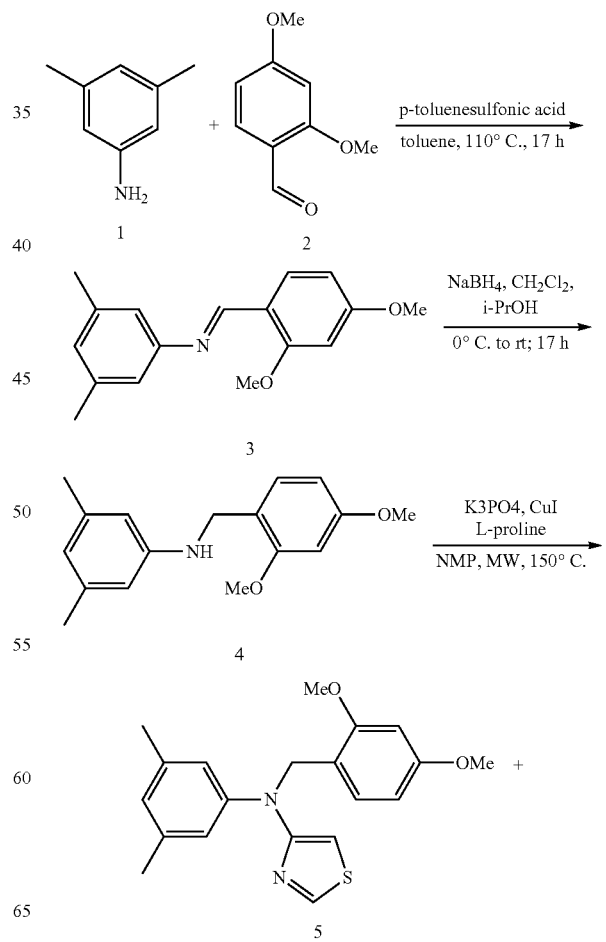

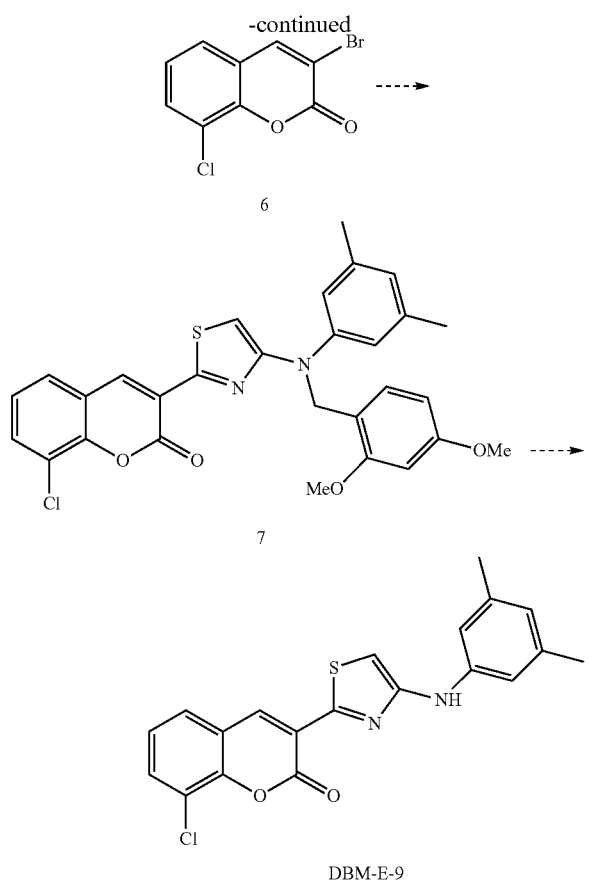

Example 2: Compound Profiling

A schematic showing a general approach for profiling the CFTR corrector drugs described herein is shown in FIG. 1. The compounds were initially subjected to the Epithelial VoltOhmmeter (EVOM) electrical bioassay measuring transepithelial resistance and voltage. A drop in transepithelial resistance in this conductivity measurement was the more reliable endpoint and was used to profile these compounds with an 8-point or a 12-point concentration-response curve. The $EC_{50}$ values for the compounds described herein and for the industry standard Vertex 809 (VX-809; Vertex Pharmaceuticals, Cambridge, Mass.) were determined (Table 1).

TABLE 1

| Compound ID | $EC_{50}$ (μM) | Maximum Effective Dose (μM) |
| --- | --- | --- |
| VX-809 | 5-10 | 10-30 |
| DBM 228 | 0.25 | 0.3 |
| DBM 308 | 0.2 | 0.3 |
| DBM 701 | 0.28 | 1.0 |
| DBM 707 | 0.26 | 1.0 |
| DBM 715 | 0.29 | 1.0 |
| DBM 328 | >30 | >30 |
| DBM-E-01 | 0.74 | 3.0 |
| DBM-E-02 | 30 | 30 |
| DBM-E-03 | 0.5 | 1.0 |
| DBM-E-04 | 1.9 | 10 |
| DBM-E-05 | Not calculated | No effective dose |
| DBM-E-05.1 | 30 | 30 |
| DBM-E-08 | 9 | 30 |
| DBM-E-09.1 | 20 | 30 |

TABLE 1-continued

| Compound ID | $EC_{50}$ (μM) | Maximum Effective Dose (μM) |
| --- | --- | --- |
| DBM-E-10 | 0.95 | 10 |
| DBM-E-11 | Not calculated | No effective dose |
| DBM-E-12 | Not calculated | No effective dose |
| DBM-E-13 | 2.7 | — |
| DBM-E-14 | 1.3 | — |
| DBM-E-16 | 0.88 | — |
| DBM-E-17 | Not calculated | — |

Example 3: SPQ High Throuphput Screening Assay

Figure 2:
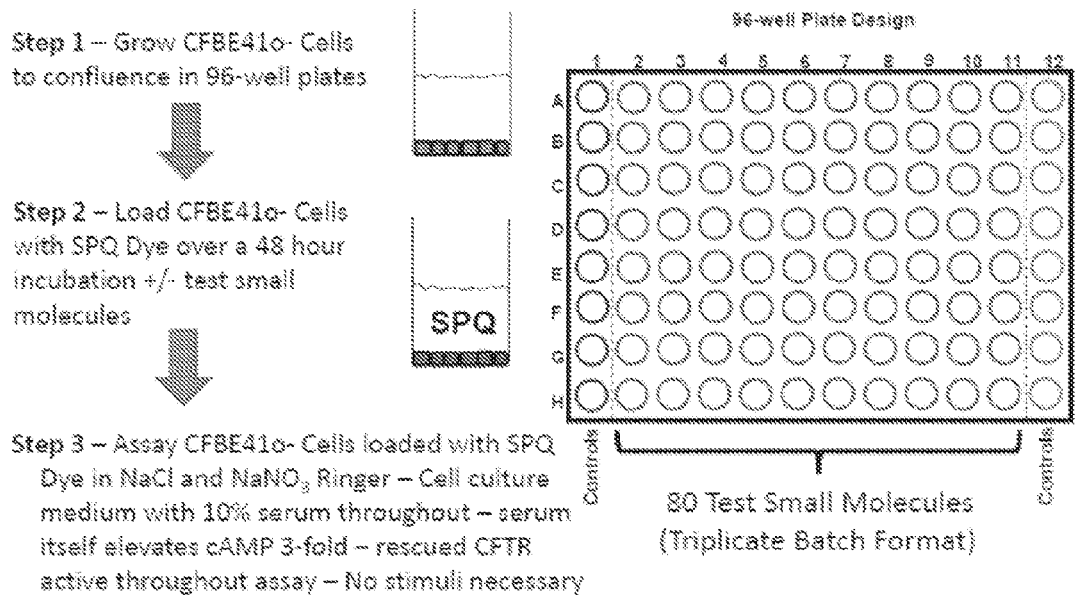
FIG. 2 is a schematic showing the general design of the SPQ fluorescence bioassay.
Figure 3:
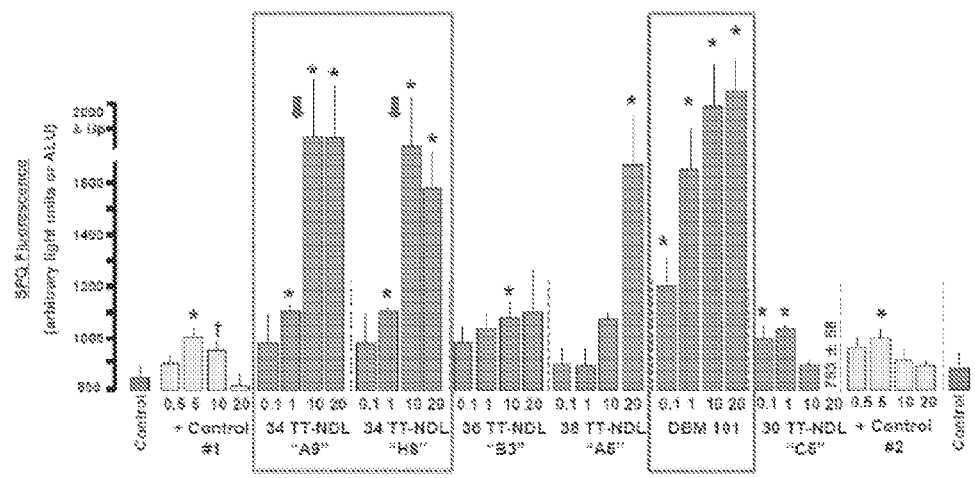
FIG. 3 shows the SPQ fluorescence bioassay data for several compounds, including Compound DBM 101.

To perform the SPQ high throuphput screening assay, CFBE41o-cells were seeded into 96-well microtiter plates and were loaded with the fluorescent halide-sensitive dye, SPQ, in serum-containing culture medium. Certain wells were loaded with known positive control corrector molecules, including VX-809. The test compounds were loaded into wells and were tested in triplicate wells at a 10 μM dose and incubated over 48 hours at room temperature. During the 48 hour period, SPQ was absorbed. Plates were washed in a sodium chloride (NaCl) based Ringer and read once over two minutes to set the baseline SPQ fluorescence activity. Then, NaCl was replaced by sodium nitrate ($NaNO_3$) based Ringer. The plates were read twice over four minutes. The primary high throughput screen (HTS) data were analyzed to detect any function of rescued delF508-CFTR under basal conditions. The plate was read up to two times to complete the SPQ HTS assay. A schematic of the method is shown in FIG. 2. Compound DBM 101 and other compounds were subjected to the assay (FIG. 3). Compound DBM 101 rescued Cl-permeability of the cell membrane, displayed dose-response effects, displayed nanomolar effects, and had no cytotoxicity (FIG. 3). Thus, the compound was confirmed as a validated corrector.

Example 4: Epithelial Voltohmmeter Electrical Assay

Figure 4:
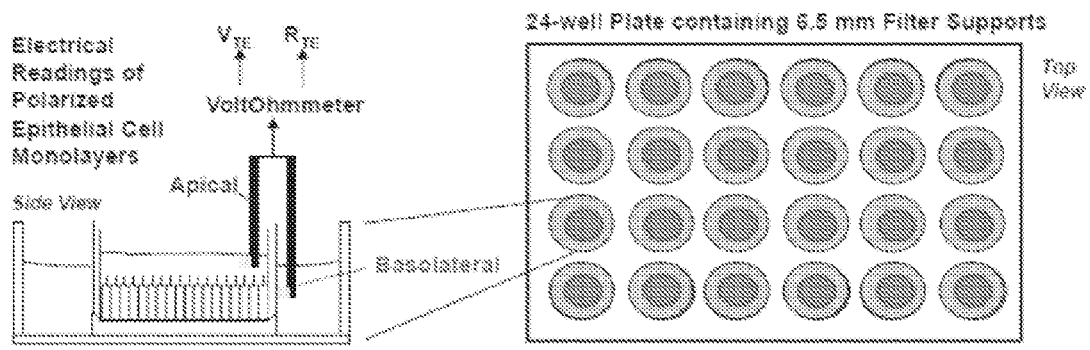
FIG. 4 is a schematic showing the general design of the epithelial voltohmmeter (EVOM) electrical assay.
Figure 5:
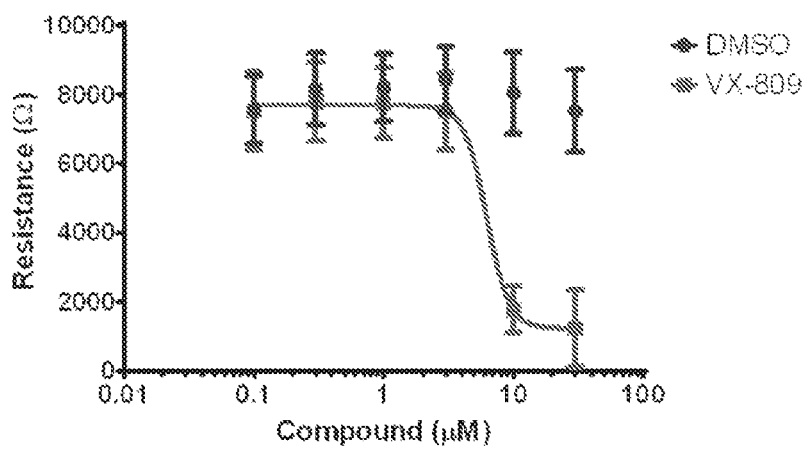
FIG. 5 is a plot showing the resistance of industry standard VX-809 at different concentrations in the EVOM electrical assay.
Figure 6:
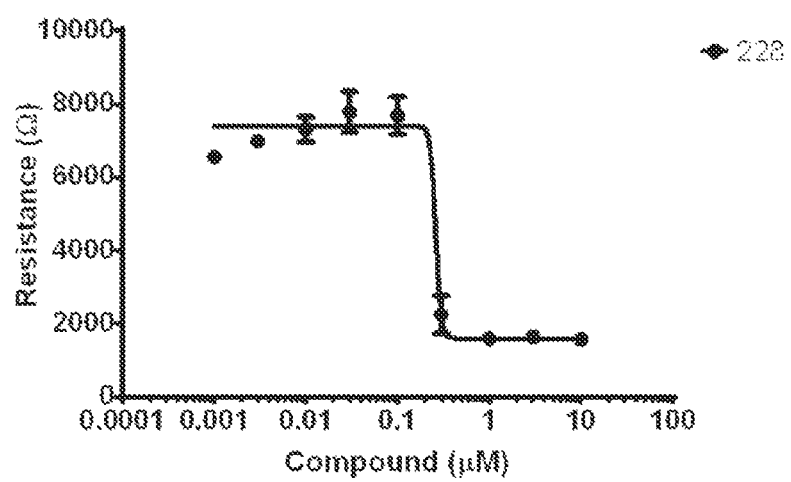
FIG. 6 is a plot showing the resistance of Compound DBM 228 at different concentrations in the EVOM electrical assay.
Figure 7:
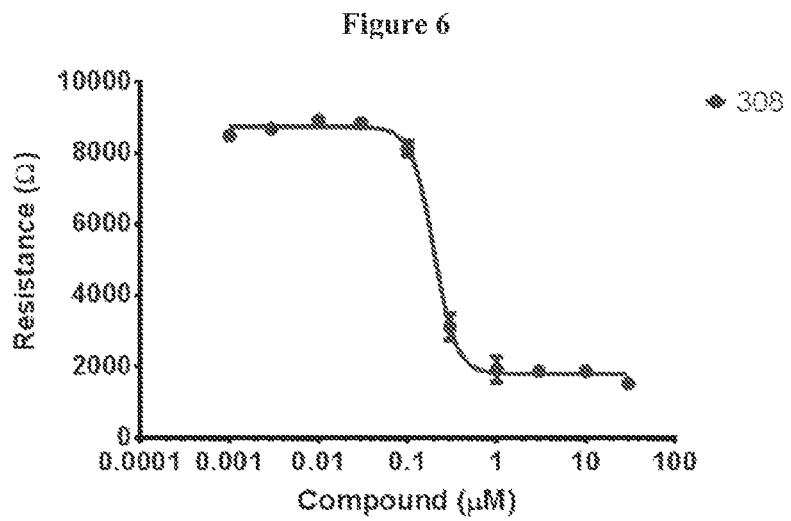
FIG. 7 is a plot showing the resistance of Compound DBM 308 at different concentrations in the EVOM electrical assay.
Figure 8:
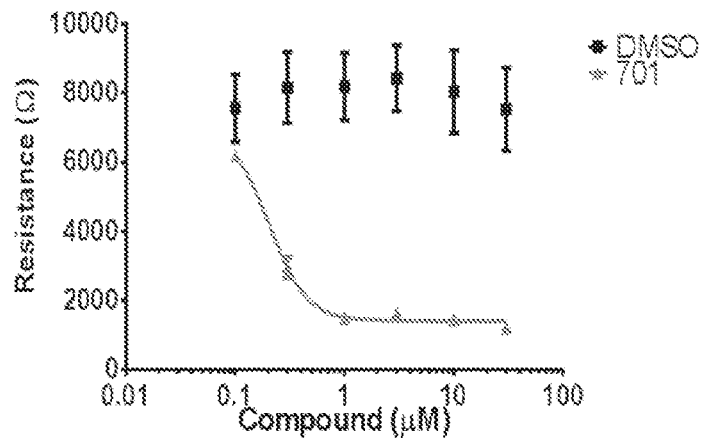
FIG. 8 is a plot showing the resistance of Compound DBM 701 at different concentrations in the EVOM electrical assay.
Figure 9:
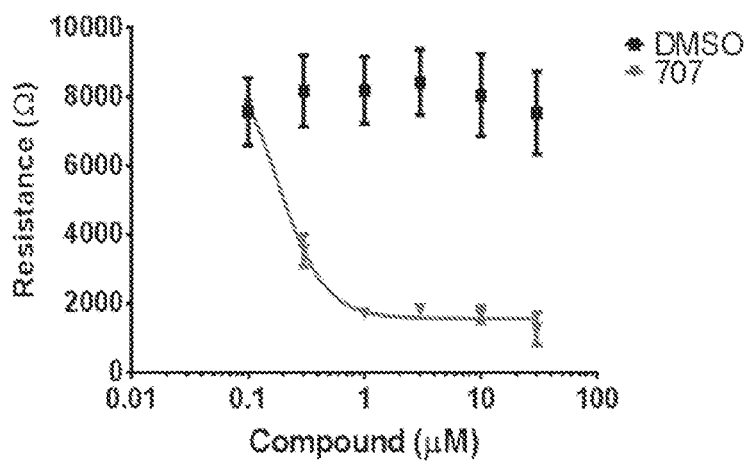
FIG. 9 is a plot showing the resistance of Compound DBM 707 at different concentrations in the EVOM electrical assay.
Figure 10:
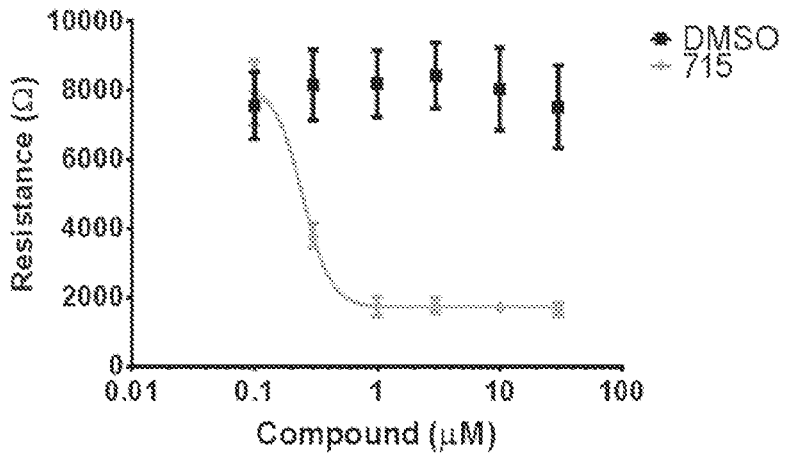
FIG. 10 is a plot showing the resistance of Compound DBM 715 at different concentrations in the EVOM electrical assay.
Figure 11:
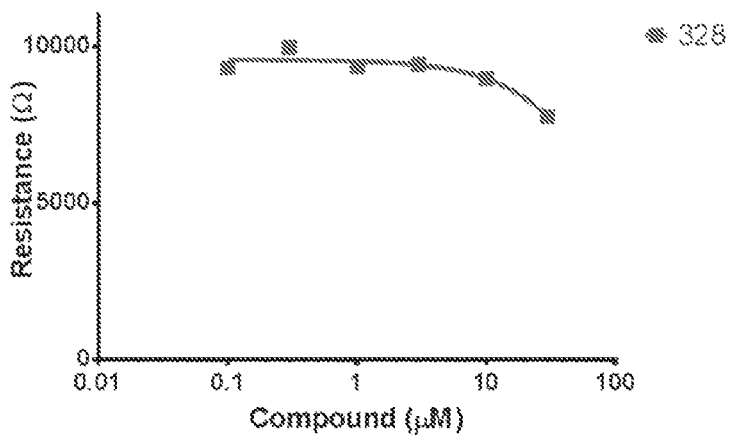
FIG. 11 is a plot showing the resistance of Compound DBM 328 at different concentrations in the EVOM electrical assay.
Figure 12:
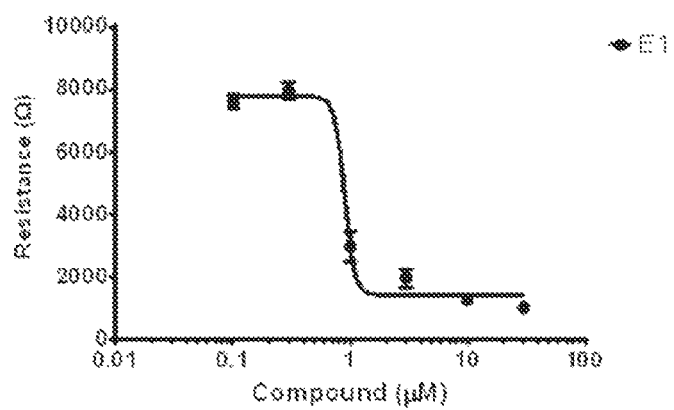
FIG. 12 is a plot showing the resistance of Compound DBM-E-01 at different concentrations in the EVOM electrical assay.
Figure 13:
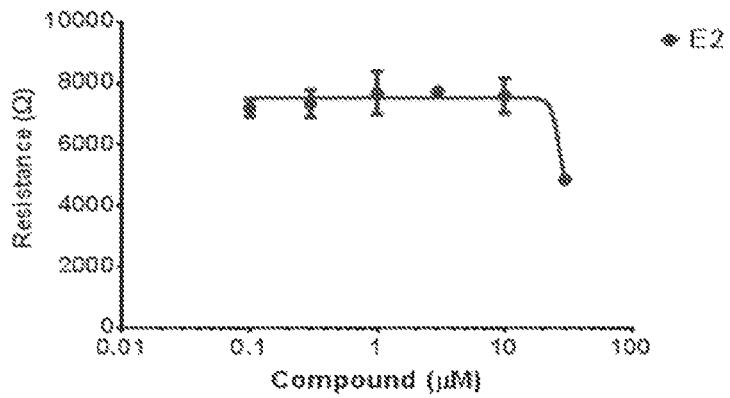
FIG. 13 is a plot showing the resistance of Compound DBM-E-02 at different concentrations in the EVOM electrical assay.
Figure 14:
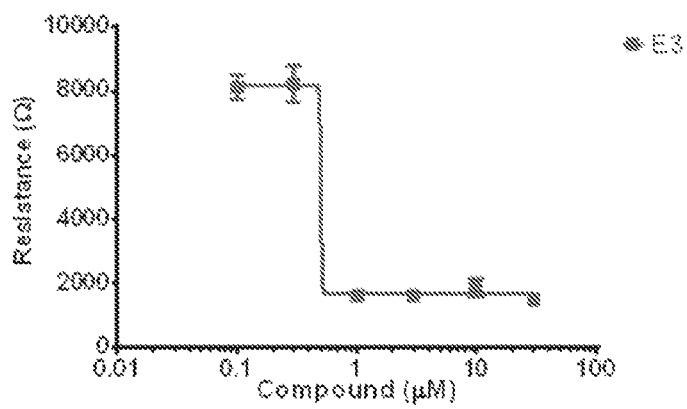
FIG. 14 is a plot showing the resistance of Compound DBM-E-03 at different concentrations in the EVOM electrical assay.
Figure 15:
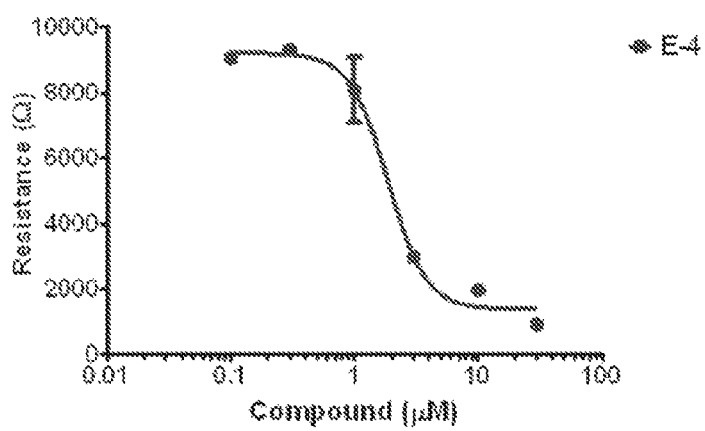
FIG. 15 is a plot showing the resistance of Compound DBM-E-04 at different concentrations in the EVOM electrical assay.
Figure 16:
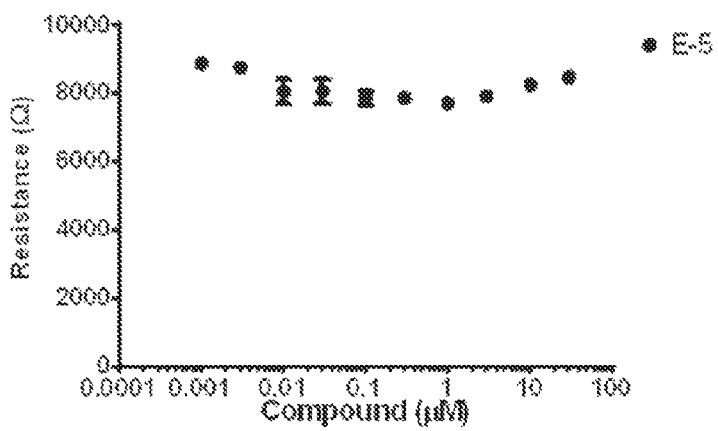
FIG. 16 is a plot showing the resistance of Compound DBM-E-05 at different concentrations in the EVOM electrical assay.
Figure 17:
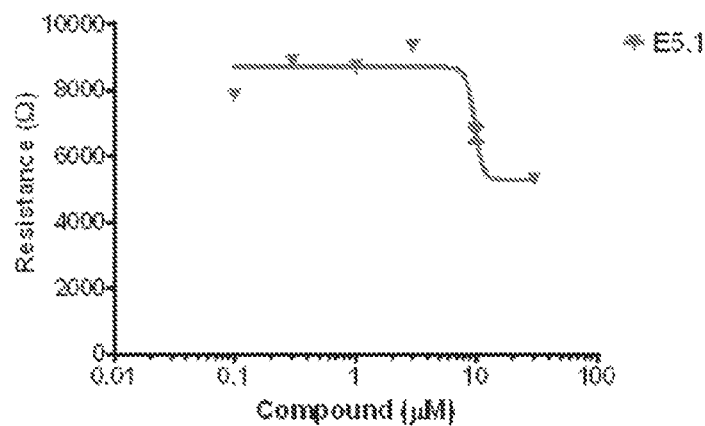
FIG. 17 is a plot showing the resistance of Compound DBM-E-05.1 at different concentrations in the EVOM electrical assay.
Figure 18:
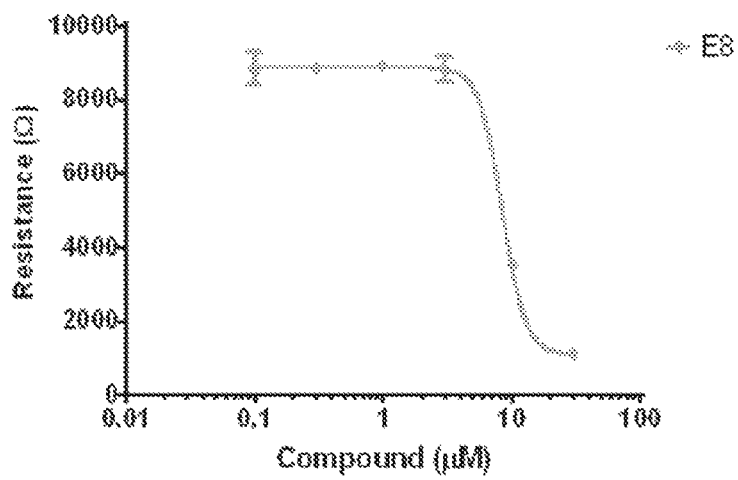
FIG. 18 is a plot showing the resistance of Compound DBM-E-08 at different concentrations in the EVOM electrical assay.
Figure 19:
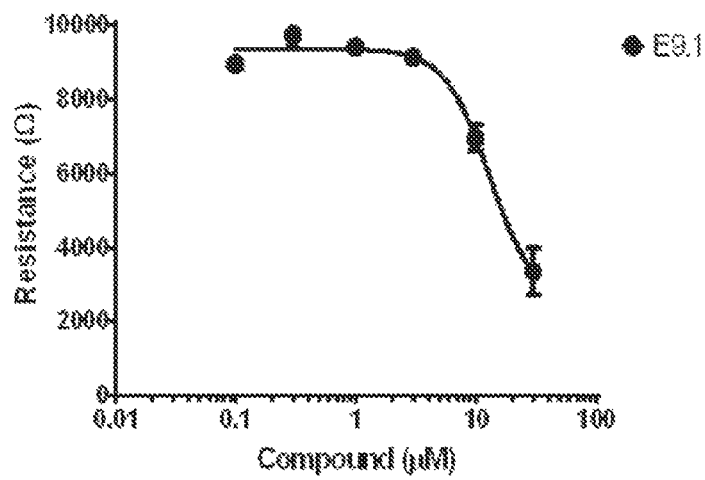
FIG. 19 is a plot showing the resistance of Compound DBM-E-9.1 at different concentrations in the EVOM electrical assay.
Figure 20:
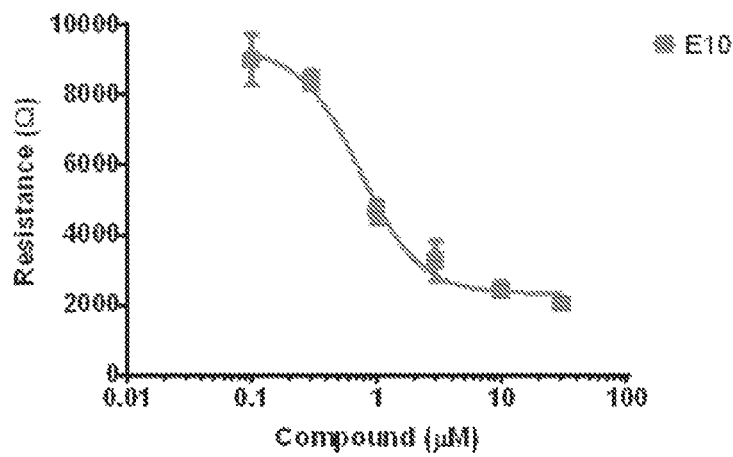
FIG. 20 is a plot showing the resistance of Compound DBM-E-10 at different concentrations in the EVOM electrical assay.
Figure 21:
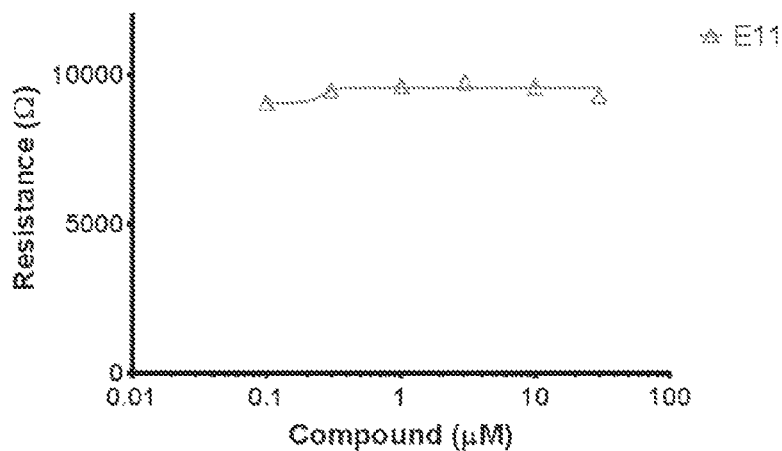
FIG. 21 is a plot showing the resistance of Compound DBM-E-11 at different concentrations in the EVOM electrical assay.
Figure 22:
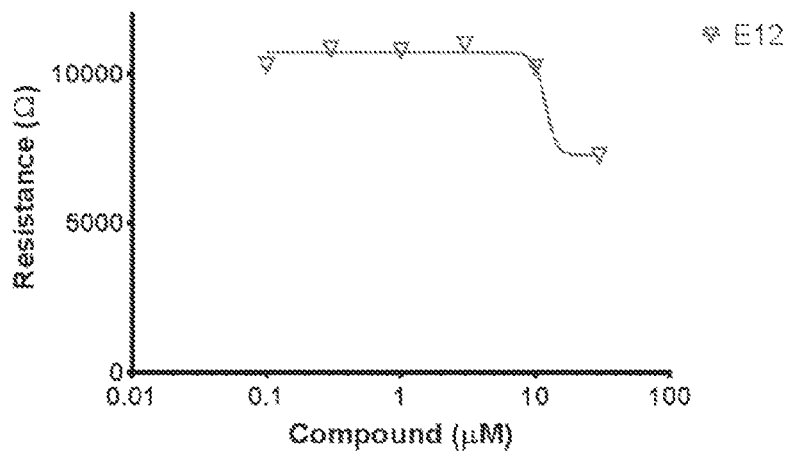
FIG. 22 is a plot showing the resistance of Compound DBM-E-12 at different concentrations in the EVOM electrical assay.
Figure 23:
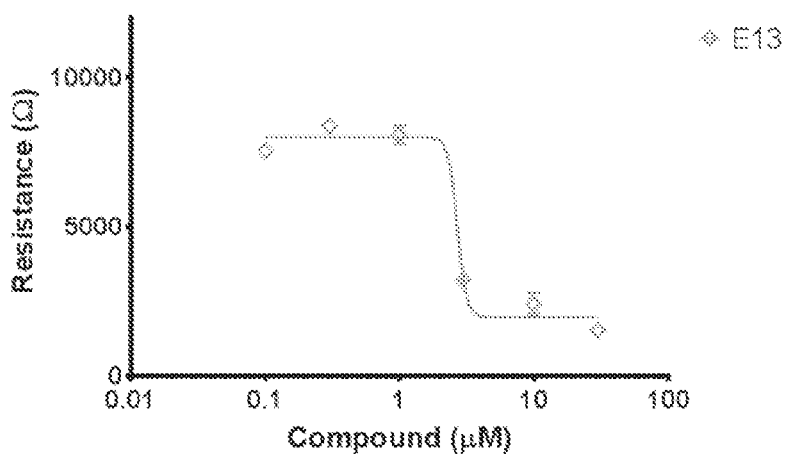
FIG. 23 is a plot showing the resistance of Compound DBM-E-13 at different concentrations in the EVOM electrical assay.
Figure 24:
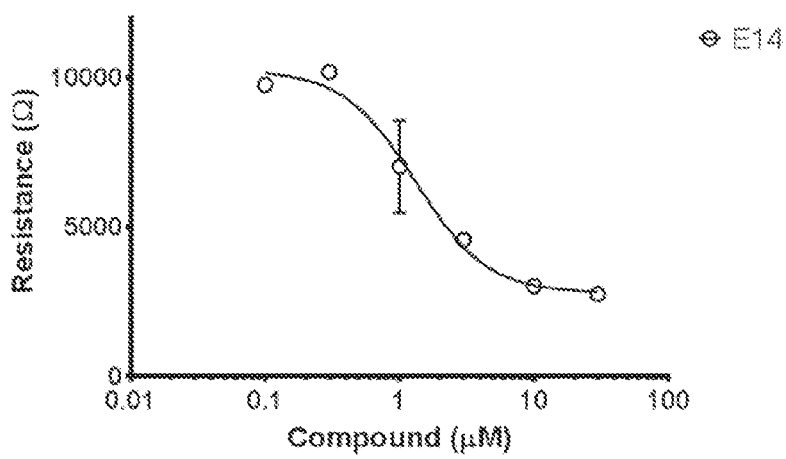
FIG. 24 is a plot showing the resistance of Compound DBM-E-14 at different concentrations in the EVOM electrical assay.
Figure 25:
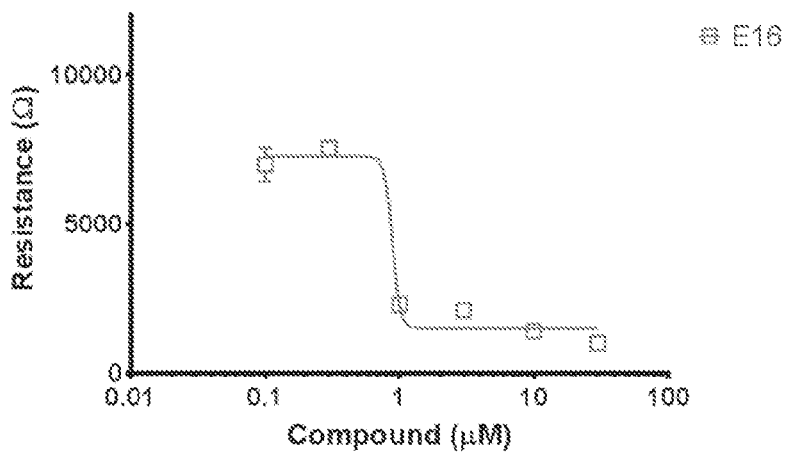
FIG. 25 is a plot showing the resistance of Compound DBM-E-16 at different concentrations in the EVOM electrical assay.
Figure 26:
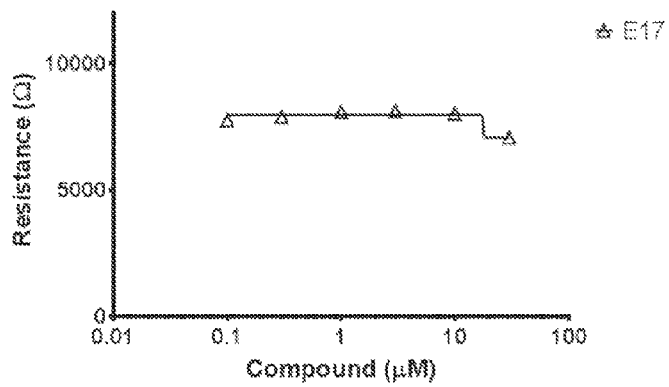
FIG. 26 is a plot showing the resistance of Compound DBM-E-17 at different concentrations in the EVOM electrical assay.

Electrical and biochemical profiling assays were performed to assess the compounds descried herein. Epithelial Voltohmmeter (EVOM) electrical assays were performed as shown in the schematic in FIG. 4. In this assay, a drop in transepithelial resistance ($R_{TE}$) indicates that delF508-CFTR Cl⁻ channels are open and active in the apical membrane of the CF human respiratory epithelium. The following compounds were tested in the EVOM electrical assay: industry standard VX-809 (FIG. 5), Compound DBM 228 (FIG. 6), Compound DBM 308 (FIG. 7), Compound DBM 701 (FIG. 8), Compound DBM 707 (FIG. 9), Compound DBM 715 (FIG. 10), Compound DBM 328 (FIG. 11), Compound DBM-E-01 (FIG. 12), Compound DBM-E-02 (FIG. 13), Compound DBM-E-03 (FIG. 14), Compound DBM-E-04 (FIG. 15), Compound DBM-E-05 (FIG. 16), Compound DBM-E-05.1 (FIG. 17), Compound DBM-E-08 (FIG. 18), Compound DBM-E-9.1 (FIG. 19), Compound DBM-E-10 (FIG. 20), Compound DBM-E-11 (FIG. 21), Compound DBM-E-12 (FIG. 22), Compound DBM-E-13 (FIG. 23), Compound DBM-E-14 (FIG. 24), Compound DBM-E-16 (FIG. 25), and Compound DBM-E-17 (FIG. 26).

Example 5: CFTR Western Blot

The compounds were then subjected to a biochemical assay to define which hit compounds rescued the band B core glycosylated endoplasmic reticulum (ER) form of delF508-CFTR within the cell interior into the maturely glycosylated band C form within the secretory pathway for proteins and within the plasma membrane. Effective compounds stabilized the band B form of CFTR and caused more of this form to accumulate at the level of the ER. The most effective compounds caused the band C form to appear.

Figure 27:
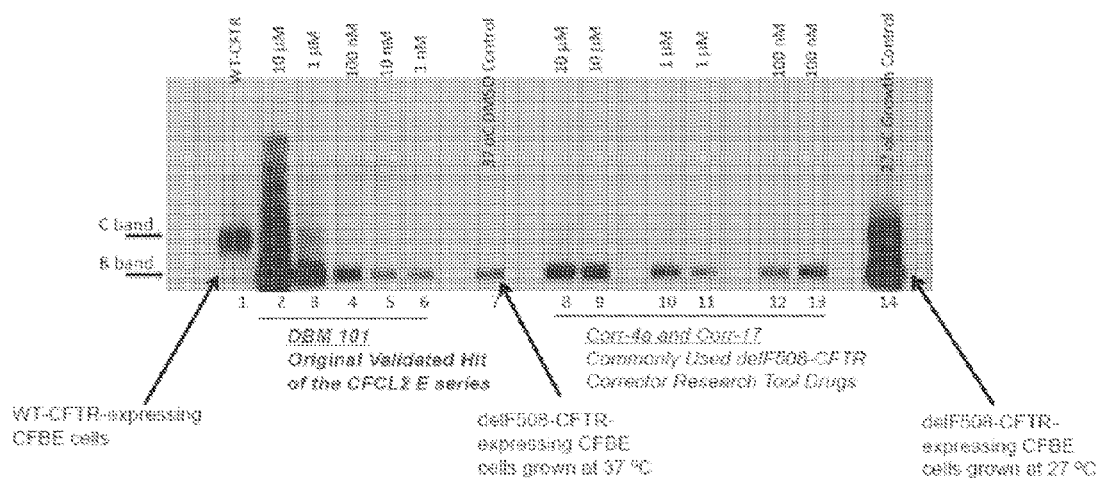
FIG. 27 contains Western blots demonstrating the delF508 CFTR rescue in CF human airway epithelial cells using Compound DBM 101 versus Corr-4a and Corr-17 at increasing dosages. WT-CFTR expressing cells, DMSO, and low temperature served as the controls.
Figure 28:
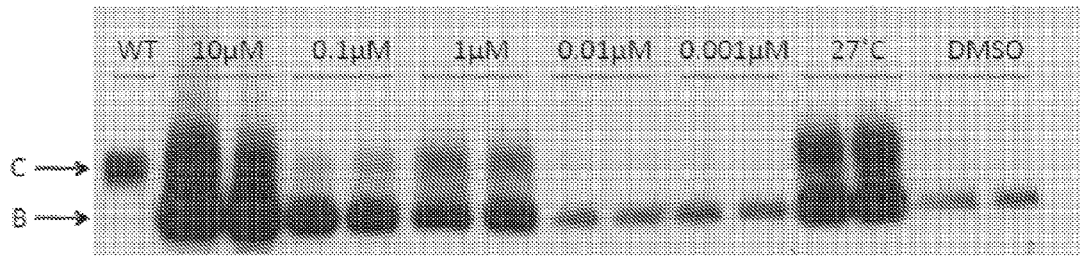
FIG. 28 contains Western blots demonstrating the delF508 CFTR rescue in CF human airway epithelial cells using Compound DBM 101 at increasing dosages (10 µM, 0.1 µM, 1 µM, 0.01 µM, and 0.001 µM). WT-CFTR expressing cells, DMSO, and low temperature (27° C.) served as the controls.
Figure 29:
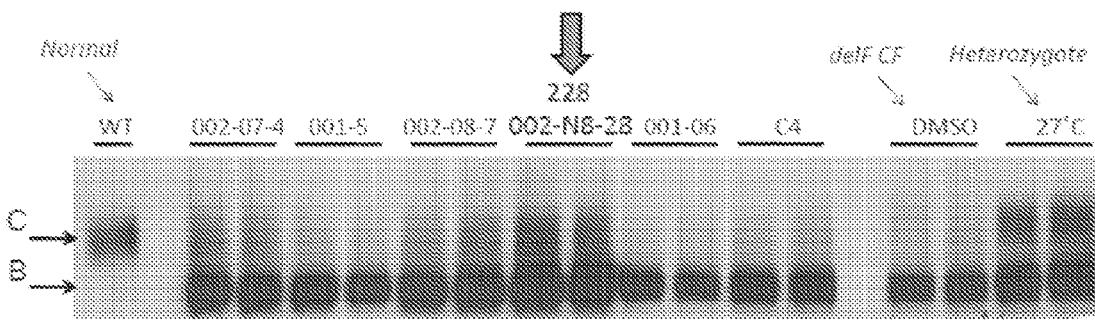
FIG. 29 contains Western blots demonstrating the delF508 CFTR rescue in CF human airway epithelial cells using Compound DBM 228 and other compounds. WT-CFTR expressing cells, DMSO, and low temperature (27° C.) served as the controls.

By way of example, the delF508-CFTR mutation can be rescued from the ER with low temperature incubation for 48 hours (see examples in the blots as the positive control). The DMSO control is the simulated CF condition where the delF508-CFTR-expressing cells were grown at physiological temperature. Compound DBM 101 was tested in the biochemical rescue assay at 10 µM, 1 µM, 100 nM, 10 nM, and 1 nM. DMSO (37° C.), Corr-4a and Corr-17 (two delF508-CFTR corrector research tool drugs) treated cells, WT-CFTR expressing cells, and low temperature (27° C.) corrected cells served as the controls. See FIG. 27. Compound DBM 101 attained the CF heterozygous phenotype of the 27° C. reduced temperature growth control at a concentration of between 1 and 10 µM. See FIGS. 27 and 28. However, known delF508-CFTR corrector drugs Corr-4a and Corr-17 discovered using heterologous cell systems over-expressing delF508-CFTR had no effect in CFBE cells (FIG. 27). Compound DBM 228 was also tested in the biochemical rescue assay at 2 µM, along with other test compounds at the same concentration. DMSO, Corr-4a treated cells, and low temperature (27° C.) corrected cells served as the controls. See FIG. 29.

Figure 30:
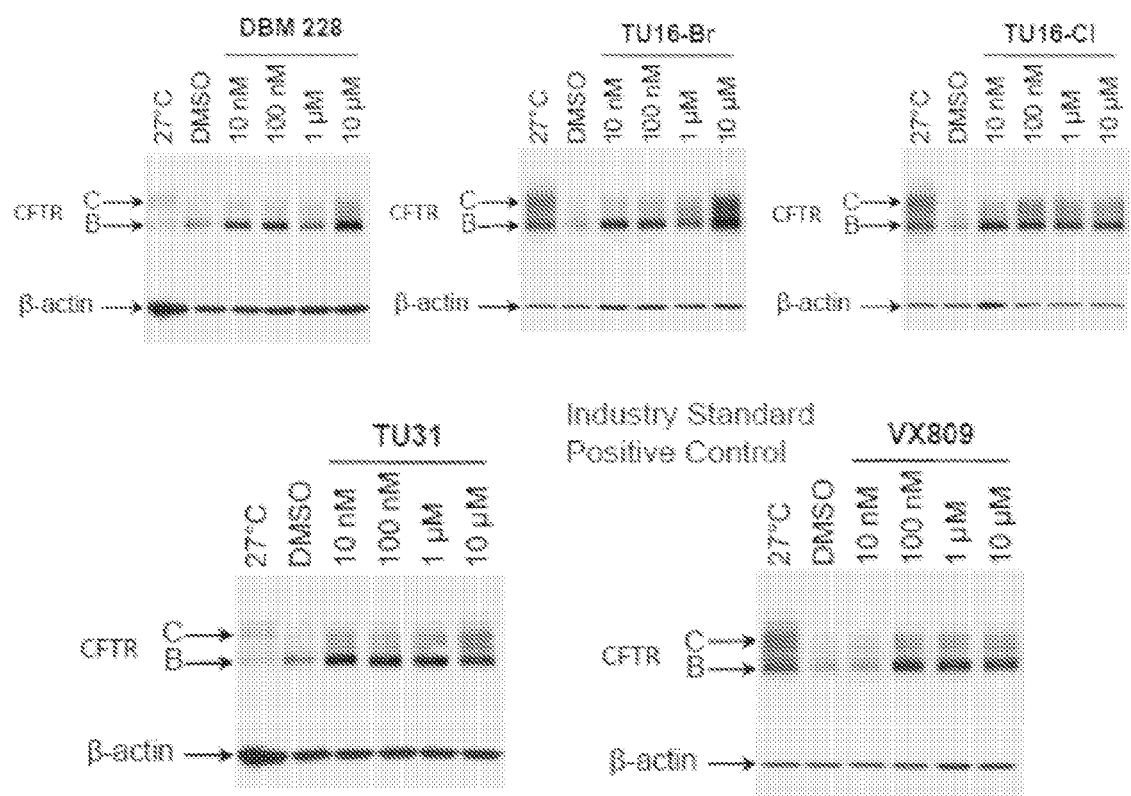
FIG. 30 contains Western blots demonstrating the delF508 CFTR rescue in CF human airway epithelial cells using Compound DBM 228, Compound DBM-003-TU16-Br, Compound DBM-003-TU16-Cl, Compound DBM-003-TU31, and industry standard VX-809 at increasing dosages (10 nM, 100 nM, 1 µM, and 10 µM). DMSO and low temperature (27° C.) served as the controls.
Figure 31:
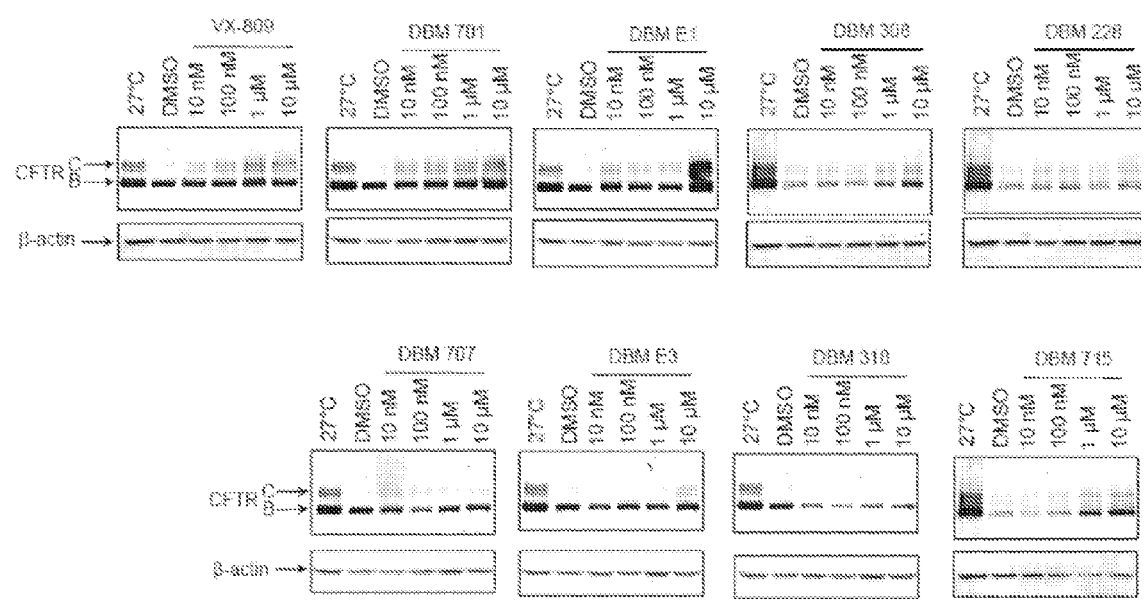
FIG. 31 contains Western blots demonstrating the delF508 CFTR rescue in CF human airway epithelial cells using Compound DBM 701, Compound DBM-E-01, Compound DBM 308, Compound DBM 228, DBM 707, DBM-E-03, DBM-318, DBM 715, and industry standard VX-809 at increasing dosages (10 nM, 100 nM, 1 µM, and 10 µM). DMSO and low temperature (27° C.) served as the controls.
Figure 32:
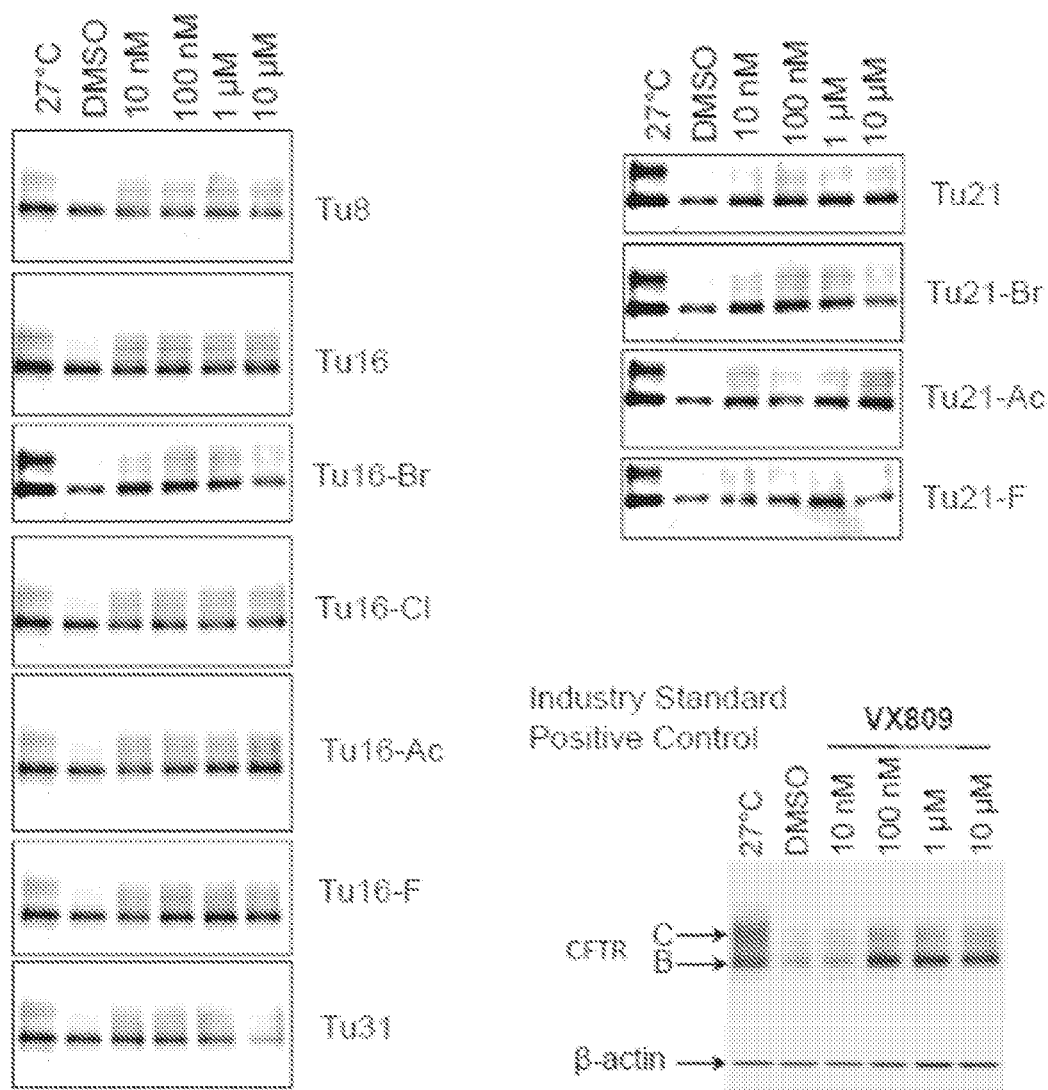
FIG. 32 contains Western blots demonstrating the delF508 CFTR rescue in CF human airway epithelial cells using Compound DBM-003-TU8, Compound DBM-003-TU16, Compound DBM-003-TU16-Br, Compound DBM-003-TU16-Cl, Compound DBM-003-TU16-Ac (DBM-003-TU16-COOCH$_3$), Compound DBM-003-TU16-F, Compound DBM-003-TU31, Compound DBM-003-TU21, Compound DBM-003-TU21-Br, Compound DBM-003-TU21-Ac (DBM-003-TU21-COOCH$_3$), Compound DBM-003-TU21-F, and industry standard VX-809 at increasing dosages (10 nM, 100 nM, 1 µM, and 10 µM). DMSO and low temperature (27° C.) served as the controls.
Figure 33:
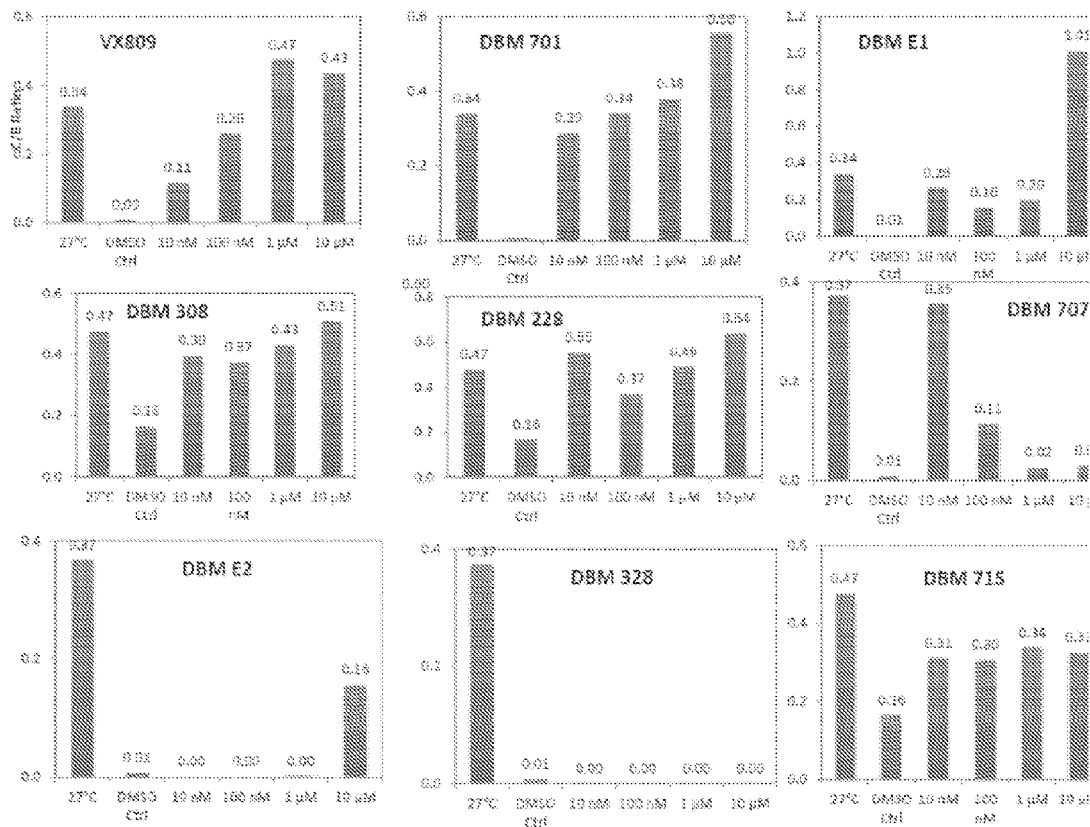
FIG. 33 shows densitometry graphs for blots of VX-809, Compound DBM 701, Compound DBM-E-01, Compound DBM 308, Compound DBM 228, Compound DBM 707, Compound DBM-E-02, Compound DBM 328, and Compound DBM 715 at increasing dosages (10 nM, 100 nM, 1 µM, and 10 µM). DMSO and low temperature (27° C.) served as the controls.

Certain compounds described herein were also tested in the biochemical rescue assay. Each compound was tested at 10 µM, 1 µM, 10 nM, and 100 nM. DMSO, WT-CFTR expressing cells, and low temperature (27° C.) corrected cells served as the controls. See FIGS. 30-32. The experiments were performed in 10% serum containing medium using the method as described above. The data demonstrate that the corrector compounds described herein are effective independent of serum protein. Densitometry graphs for blots of certain compounds are shown in FIG. 33. The data show that the compounds described herein are potent biochemical correctors of delF508-CFTR and superior to VX-809.

Example 6: Ussing Chamber Measurements

Figure 34:
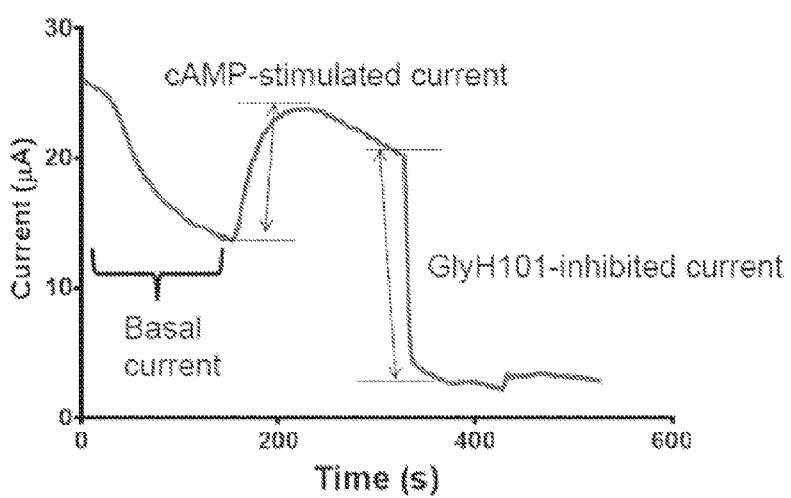
FIG. 34 is a schematic of an Ussing Chamber electrical data trace.

Ussing chamber electrophysiological assays were also performed to confirm that the corrected and active delF508-CFTR Cl-channels are functional in the apical membrane of a cystic fibrosis respiratory epithelium. In the assay, polarized CFBE cell monolayers are cultured over a 4-6 day period until they exceed 1,000 Ohms transepithelial resistance. The monolayers are then treated with the compounds described herein for 24 hours against DMSO vehicle controls. The short-circuit current is measured in the Ussing chamber under voltage-clamped conditions to gauge the level of CFTR function in the apical membrane via multiple measures. Three components can be determined from the Cl⁻ current trace and all components are valuable (see FIG. 34). The basal current section indicates whether the compounds can activate delF508-CFTR as well as correct its folding defect under basal conditions. The cAMP-stimulated current section indicates whether cyclic AMP mobilizing drugs stimulate delF508-CFTR channels further. Further, GlyH101 is a selective CFTR inhibitor that shows the amount of stimulated current that is sensitive to the inhibitor.

Figure 35:
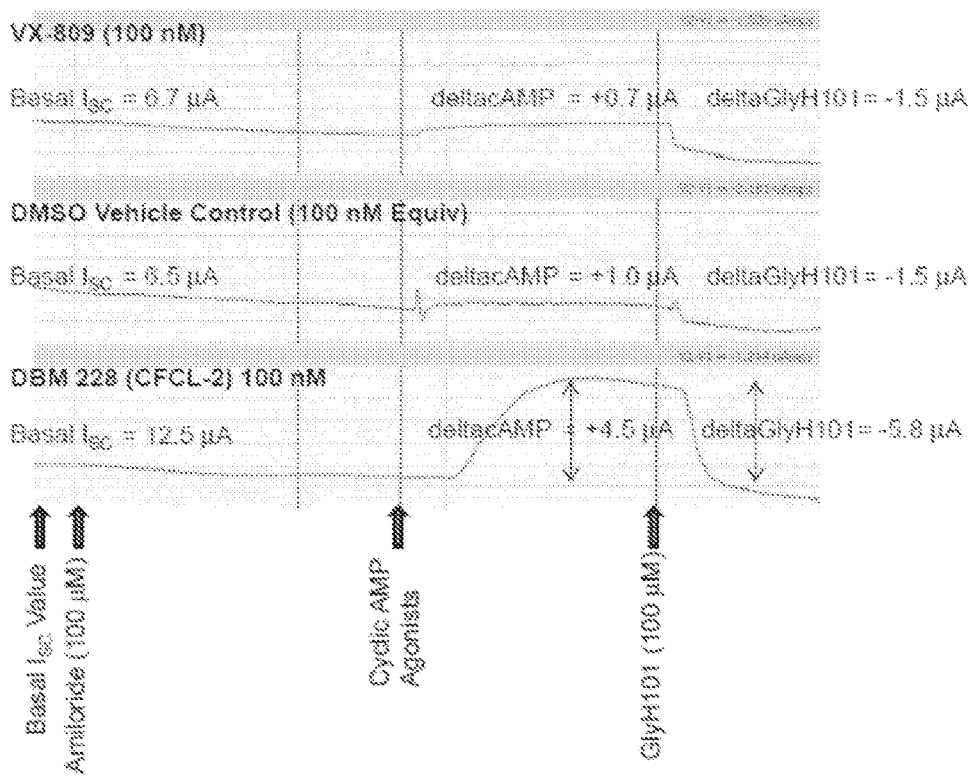
FIG. 35 is a schematic of an Ussing chamber-derived short-circuit current trace illustrating the correction of functional apical membrane-resident delF508-CFTR chloride ion channels in a high-resistance CF human airway epithelial cell monolayer with VX-809 at 100 nM (top plot), DMSO vehicle control (middle plot) and Compound DBM 228 at 100 nM (bottom plot).
Figure 36:
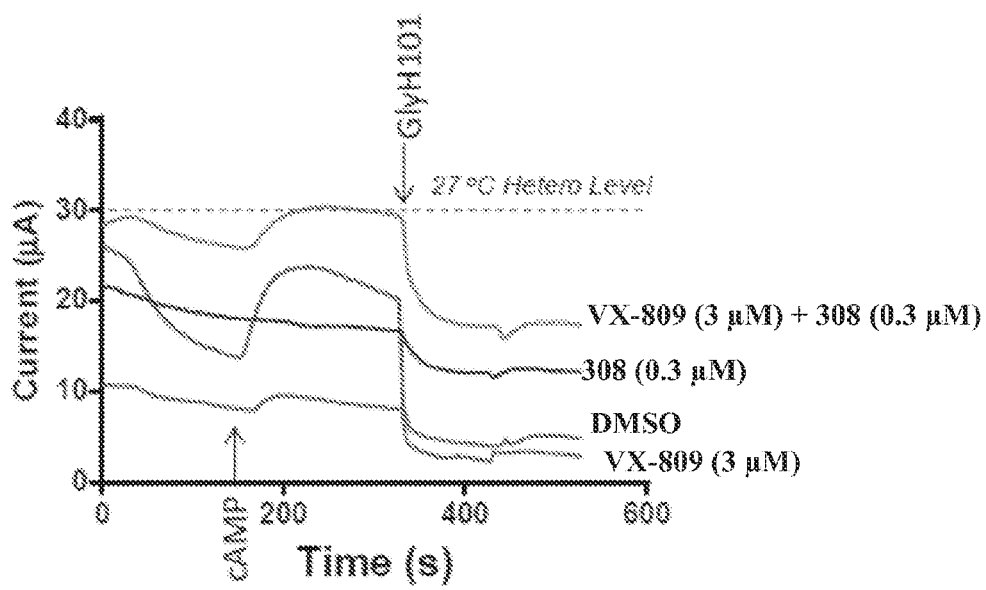
FIG. 36 is a schematic of an Ussing chamber-derived short-circuit current trace illustrating the correction of functional apical membrane-resident delF508-CFTR chloride ion channels in a high-resistance CF human airway epithelial cell monolayer with Compound DBM 308 at 0.3 μM, VX-809 at 3 μM, a combination of VX-809 at 3 μM and Compound DBM 308 at 0.3 μM, and a DMSO vehicle control.
Figure 37:
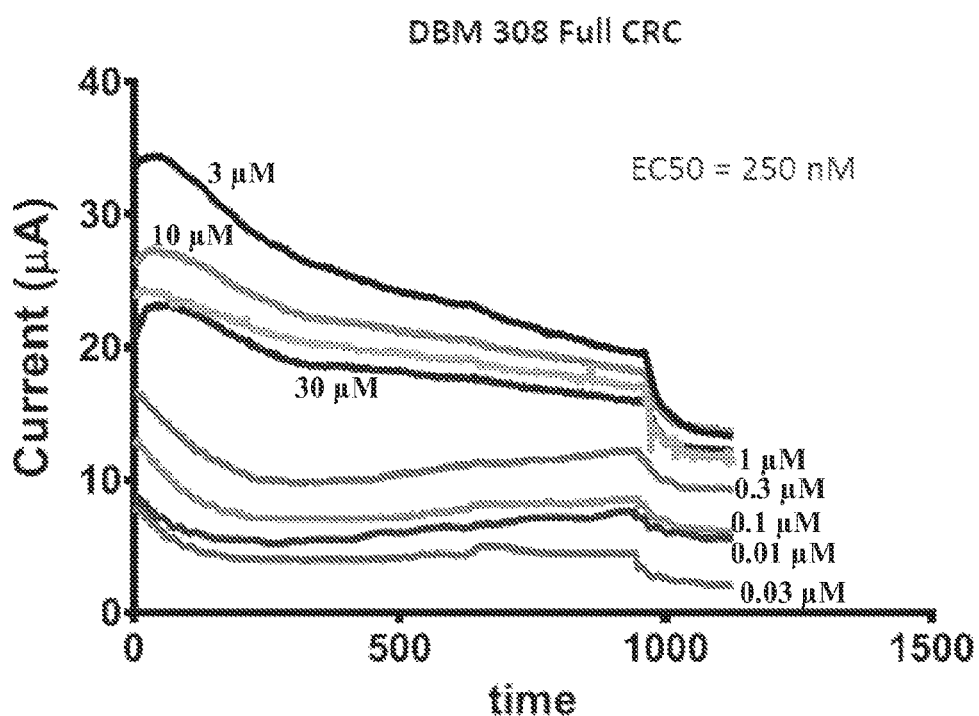
FIG. 37 shows a concentration-response curve plot for Compound DBM 308 in Ussing chambers.

Ussing chamber-derived short-circuit current data was obtained for Compounds DBM 228 (see FIG. 35) and DBM 308 (see FIG. 36). Compound DBM 228 showed robust correction of functional delF508-CFTR chloride ion channels under basal conditions and triggers cAMP-stimulated Cl⁻ current at nM concentrations. VX-809 had no effect at nM concentrations. Compound DBM 308, at 0.3 µM, increased basal Cl currents to levels equivalent or larger than VX-809 at 3 µM (which is the optimal concentration for VX-809's Ussing effects). There is little cAMP-stimulated Cl⁻ current and less GlyH101-sensitive Cl⁻ current with the compound as compared to VX 809. Together, these results show that the compounds described herein correct delF508-CFTR but also positively influence and up-regulate additional Cl⁻ channel populations. The combination of DBM 308 and VX-809 at 0.3 µM and 3 µM, respectively, stimulated overall Cl⁻ current to levels seen in 27° C. reduced temperature growth controls (i.e., the CF heterozygote). A concentration-response curve plot for DBM 308 is shown in FIG. 37.

Example 7: Epithelial Sodium Channel Inhibition

Figure 38:
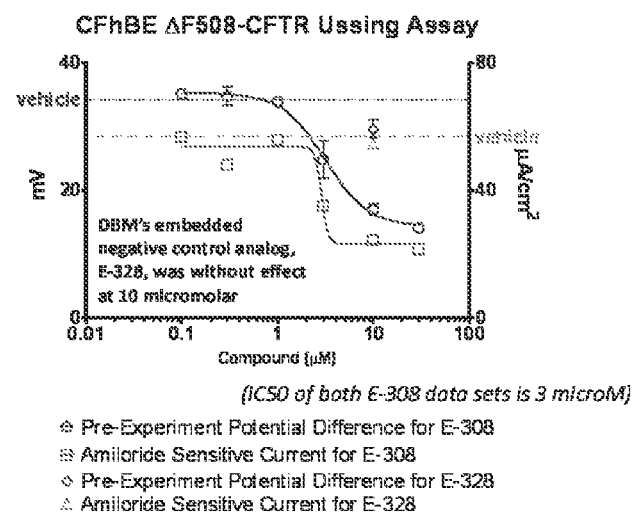
FIG. 38 shows a plot of an Ussing chamber derived trace illustrating the inhibition of amiloride sensitive epithelial sodium channel currents in primary CF human bronchial epithelial cell monolayers bearing the delF508-CFTR mutation with Compound DBM 308 and Compound DBM 328.

The concentration-dependent inhibition of epithelial sodium channel (ENaC) activity was studied using Ussing chamber electrical experiments and related confirmatory electrophysiology assays. Chronic overnight pre-treatment (12-18 hours prior to assay) yielded the CRC-based data shown in FIG. 38. Electrical measurements on vehicle-treated cells are also shown in the plot in FIG. 38. The inactive drug analog, Compound DBM 328, was without effect at 10 micromolar (data shown in the single diamond and triangle symbols above the 10 micromolar indicator on the X-axis). The electrophysiological assays profiled a panel of compounds, as described herein, at prescribed concentrations. Further evidence of correction and activation of delF508-CFTR under basal conditions was observed by the robust inhibition of amiloride-sensitive ENaC sodium current under basal conditions that displays a CRC relationship with an $IC_{50}$ of 3 micromolar. This effect was also displayed by the pre-experiment potential difference measurement.

Figure 39:
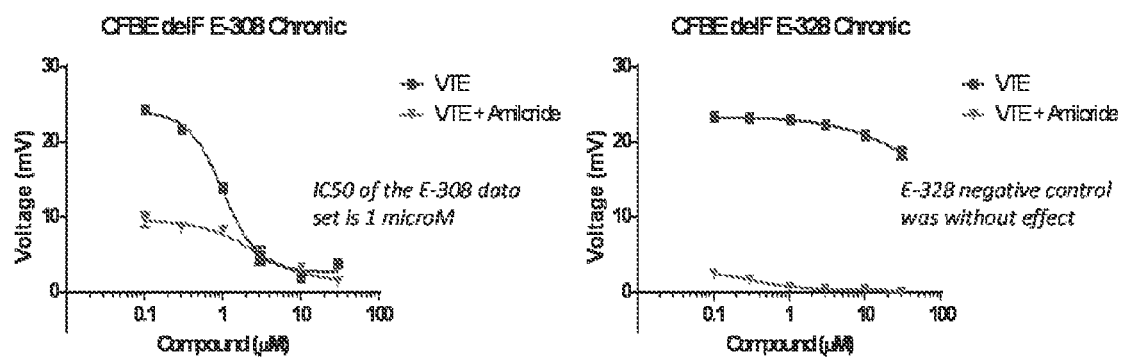
FIG. 39 shows plots of data generated from electrical experiments using CF bronchial epithelia cell monolayers bearing the delF508-CFTR mutation with chronic treatment of Compound DBM 308 (left plot) and Compound DBM 328 (right plot).

The results were confirmed in electrical experiments using the CFBE-delF508 cell monolayer platform (see FIG. 39). Chronic (i.e., overnight treatment with the drugs) and acute additions of Compound DBM 308 and of Compound DBM 328 were tested. The amiloride-sensitive transepithelial voltage (VTE) was inhibited in a dose-dependent manner by Compound DBM 308 but not by Compound DBM 328. Both sets of data show an $IC_{50}$ for chronic inhibition of ENaC at 1-3 micromolar. The concentration of Compound DBM 308 $EC_{50}$ on correction and activation of delF508-CFTR in multiple bioassays (fluorescence, biochemical, electrical) and under basal (unstimulated) conditions is 0.1-1 micromolar. Both the CFTR and ENaC effects require overnight treatments with drug. Acute addition is without effect on CFTR or ENaC. Acute addition of either compound was without effect on amiloride-sensitive transepithelial voltage (VTE). The delF508 correction at the level of the endoplasmic reticulum and corrected delF508-CFTR activation at the level of the apical plasma membrane, in turn, inhibits ENaC in the same membrane. All effects are desired for a CF therapeutics approach to form a triple therapeutic mode of action.

Example 8: Comprehensive, High Sensitivity Proteomics

A comprehensive, high sensitivity proteomics analysis was performed for Compound DBM 308-treated CFBE cells versus vehicle-treated and inactive analog (Compound DBM 328) controls. Greater than 99% of proteins were unaffected by this pattern of treatment (overnight 18-hour pretreatment).

In analysis of the short list of proteins that were changed in a statistically significant manner, no relationship or protein target affected explains the beneficial effects of Compound DBM 308 in CF. Not to be bound by theory, Compound DBM 308 may bind directly to the misfolded region of delF508-CFTR or a very closely associated regulator of delF508-CFTR protein processing, trafficking, and function.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A compound of the following formula:

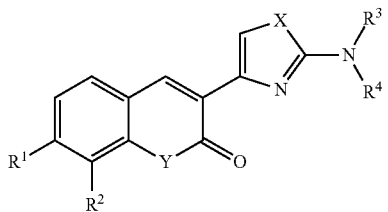

or a pharmaceutically acceptable salt or prodrug thereof, wherein:
- $R^1$ is hydrogen, halogen, hydroxyl, substituted or unsubstituted alkoxyl, substituted or unsubstituted amino, substituted or unsubstituted $C_{1-6}$ alkyl, or substituted or unsubstituted heterocycloalkyl;
- $R^2$ is halogen, hydroxyl, nitro, cyano, azido, thiocyanato, trifluoromethyl, substituted or unsubstituted amino, substituted or unsubstituted carbonyl, or substituted or unsubstituted $C_{1-6}$ alkyl;
- $R^3$ is hydrogen or substituted or unsubstituted $C_{1-6}$ alkyl;
- $R^4$ is substituted or unsubstituted $C_{1-6}$ alkyl, substituted or unsubstituted aryl, or substituted or unsubstituted heteroaryl;
- X is S or O; and
- Y is O, NH, or $NCH_3$.

2. The compound of claim 1, wherein the compound is selected from the group consisting of:

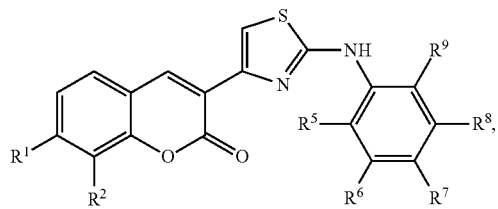

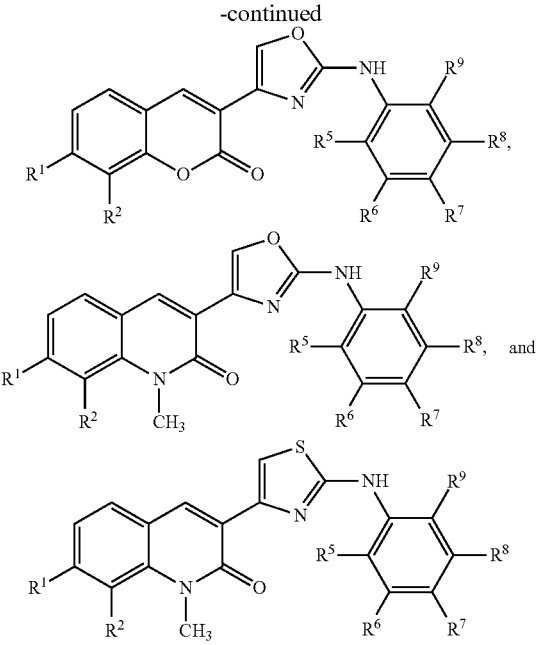

wherein $R^5$, $R^6$, $R^7$, $R^8$, and $R^9$ are each independently selected from hydrogen, halogen, hydroxyl, substituted or unsubstituted alkoxy, cyano, nitro, trifluoromethyl, substituted or unsubstituted carbonyl, substituted or unsubstituted amino, substituted or unsubstituted $C_{1-6}$ alkyl, substituted or unsubstituted $C_{2-6}$ alkenyl, substituted or unsubstituted aryl, substituted or unsubstituted sulfonamide, substituted or unsubstituted sulfonyl, or substituted or unsubstituted thio; and wherein optionally $R^1$ and $R^2$, $R^5$ and $R^6$, $R^6$ and $R^7$, $R^7$ and $R^8$, or $R^8$ and $R^9$ combine to form a substituted or unsubstituted aryl, substituted or unsubstituted cycloalkenyl, substituted or unsubstituted heteroaryl, or substituted or unsubstituted heterocycloalkyl.

3. A compound selected from the group consisting of:

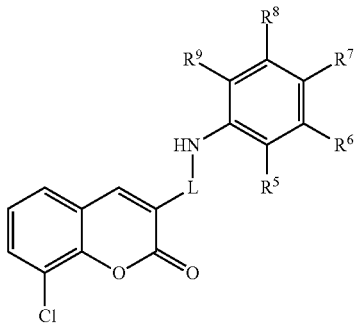

or a pharmaceutically acceptable salt or prodrug thereof, wherein:
- L is a heteroaryl; and
- $R^5$, $R^6$, $R^7$, $R^8$, and $R^9$ are each independently selected from hydrogen and methoxy.

4. A composition comprising one or more of the compounds of claim 1 and a pharmaceutically acceptable carrier.

5. A method for the treatment of a protein folding disorder in a subject, comprising:
administering to a subject an effective amount of a compound of claim 1.

6. The method of claim 5, wherein the protein folding disorder is cystic fibrosis.

7. The method of claim 5, wherein the protein folding disorder is a chronic obstructive pulmonary disease.

8. A method of rescuing halide efflux in a cell, comprising:
contacting a cell with a compound of claim 1, wherein the cell endogenously expresses a CFTR mutation.

9. The method of claim 8, wherein the CFTR mutation is delF508-CFTR.

10. The method of claim 8, wherein the halide efflux is chloride efflux.

11. A method of correcting a processing defect of a delF508-CFTR protein in a cell, comprising:
contacting a cell with a compound of claim 1, wherein the cell expresses a delF508-CFTR mutation.

12. The method of claim 8, wherein the cell is a CF human airway epithelial cell.

13. The method of claim 8, wherein the cell is a CF human lung.

14. A method of correcting functional delF508-CFTR chloride channels in a cell, comprising:
contacting a cell with a compound of claim 1, wherein the cell is a polarized epithelial cell.

15. The method of claim 8, wherein the method is performed in vitro.

16. The method of claim 8, wherein the method is performed in vivo.

17. The compound of claim 1, wherein the compound is

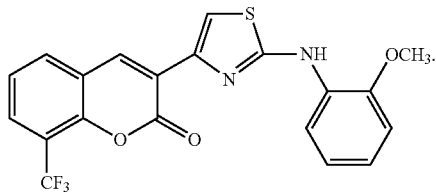 [SMILES: COc1ccccc1Nc1nc(-c2cc3cccc(C(F)(F)F)c3oc2=O)cs1]

18. The compound of claim 1, wherein $R^1$ is hydrogen, $R^2$ is trifluoromethyl, $R^4$ is substituted aryl, X is S, and Y is O.

19. The compound of claim 2, wherein the compound is

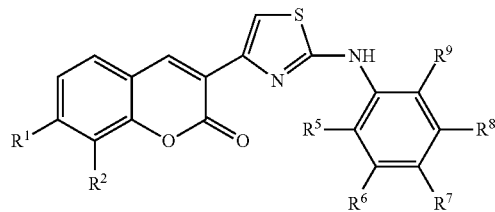

and
wherein $R^1$ is hydrogen, $R^2$ is trifluoromethyl, $R^5$ is substituted or unsubstituted alkoxy, $R^6$ is hydrogen, $R^7$ is hydrogen, $R^8$ is hydrogen, and $R^9$ is hydrogen.

20. A compound of the following formula:

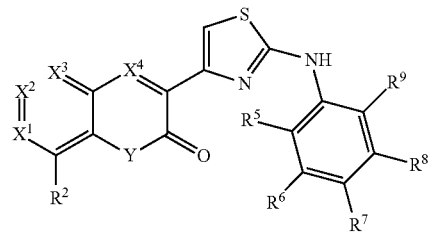

or a pharmaceutically acceptable salt or prodrug thereof, wherein:
$X^1$, $X^2$, $X^3$ and $X^4$ are each CH;
Y is O or NR, where R is hydrogen or methyl;
$R^2$ is $C_{1-6}$ alkyl, halogen, or trifluoroalkyl; and
$R^5$, $R^6$, $R^7$, $R^8$, and $R^9$ are each independently selected from hydrogen and methoxy.

21. A compound of the following formula:

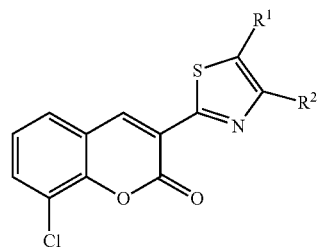

or a pharmaceutically acceptable salt or prodrug thereof, wherein:
$R^1$ and $R^2$ are each independently selected from hydrogen, substituted or unsubstituted amino, and substituted or unsubstituted carbonyl,
wherein at least one of $R^1$ or $R^2$ is substituted amino.

22. A compound of the following formula:

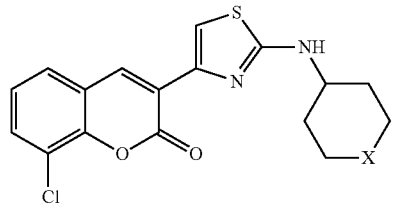

or a pharmaceutically acceptable salt or prodrug thereof, wherein:
X is $CH_2$, NH, or O.

* * * * *